United States Patent
Zhao et al.

(10) Patent No.: US 10,800,785 B2
(45) Date of Patent: Oct. 13, 2020

(54) SUBSTITUTED PYRROLO[2,3-D]PYRIDAZIN-4-ONES AND PYRAZOLO[3,4-D]PYRIDAZIN-4-ONES AS PROTEIN KINASE INHIBITORS

(71) Applicants: Shanghai Fochon Pharmaceutical Co., Ltd., Shanghai (CN); Fochon Pharmaceuticals, Ltd., Nanan District, Chongqing (CN)

(72) Inventors: Xingdong Zhao, Chongqing (CN); Weipeng Zhang, Chongqing (CN); Zhifang Chen, Chongqing (CN); Ling Chen, Chongqing (CN); Xianlong Wang, Chongqing (CN); Zhifu Li, Chongqing (CN); Rui Tan, Chongqing (CN); Lijun Yang, Chongqing (CN); Haohan Tan, Chongqing (CN); Bin Liu, Chongqing (CN); Kai Ran, Chongqing (CN); Zongyao Zou, Chongqing (CN); Min Lin, Chongqing (CN); Jing Sun, Chongqing (CN); Weibo Wang, Moraga, CA (US)

(73) Assignees: Shanghai Fochon Pharmaceutical Co., Ltd., Shanghai (CN); Fochon Pharmaceuticals, Ltd., Chongqing (CN)

( * ) Notice: Subject to any disclaimer, the term of this patent is extended or adjusted under 35 U.S.C. 154(b) by 0 days.

(21) Appl. No.: 16/312,063

(22) PCT Filed: Jun. 20, 2017

(86) PCT No.: PCT/CN2017/089123
§ 371 (c)(1),
(2) Date: Dec. 20, 2018

(87) PCT Pub. No.: WO2017/219955
PCT Pub. Date: Dec. 28, 2017

(65) Prior Publication Data
US 2019/0161489 A1 May 30, 2019

Related U.S. Application Data

(60) Provisional application No. 62/412,768, filed on Oct. 25, 2016, provisional application No. 62/353,535, filed on Jun. 22, 2016.

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC .................................................. C07D 487/04
See application file for complete search history.

(56) References Cited

U.S. PATENT DOCUMENTS

2017/0313683 A1* 11/2017 Wang .................. C07D 471/04

FOREIGN PATENT DOCUMENTS

| WO | 2014113932 A1 | 7/2014 |
| WO | 2014113942 A1 | 7/2014 |
| WO | 2016007185 A1 | 1/2016 |
| WO | 2016112637 A1 | 7/2016 |

OTHER PUBLICATIONS

The University of Maryland Medical Center. Myeloproliferative disorders: University of Maryland Medical Center. (2016).Web (http://umm.edu/health/medical/altmed/condition/myeloproliferative-disorders).*
MedicineNet.com (2004) Web (http://www.medterms.com).*
Campbell, Robert. J. Clin. Med. 2018, 7, 62.*
Int'l Search Report dated Sep. 21, 2017 in Int'l Patent No. PCT/CN2017/089123.
Extended European Search Report dated Oct. 9, 2019 in European Application No. 17814693.2.
Labels for IMBRUVICA, FDA, 33 pages (2016).
Vij et al., "Ibrutinib, Single Agent or in Combination with Dexamethasone, in Patients with Relapsed or Relapsed/Refractory Multiple Myeloma (MM): Preliminary Phase 2 Results," Blood, vol. 124, No. 21, 6 pages (2014).

* cited by examiner

*Primary Examiner* — Emily A Bernhardt
*Assistant Examiner* — Laura M Daniel
(74) *Attorney, Agent, or Firm* — Ice Miller LLP

(57) ABSTRACT

Provided are certain compounds or pharmaceutically acceptable salts thereof which can inhibit kinase activity of Bruton's tyrosine kinase (BTK) and may be useful for the treatment of diseases like cancer, immunological disease and inflammation.

18 Claims, No Drawings

SUBSTITUTED PYRROLO[2,3-D]PYRIDAZIN-4-ONES AND PYRAZOLO[3,4-D]PYRIDAZIN-4-ONES AS PROTEIN KINASE INHIBITORS

CROSS-REFERENCE TO RELATEED APPLICATION

This application is a Section 371 of International Application No. PCT/CN2017/089123, filed Jun. 20, 2017, which was published in the English language on Dec. 28, 2017 under International Publication No. WO 2017/219955 A1, which claims the benefit of U.S. provisional application No. 62/353,535, filed Jun. 22, 2016, and U.S. provisional application No. 62/412,768, filed Oct. 25, 2016, the disclosures of which are incorporated herein by reference in their entireties.

FIELD OF THE INVENTION

Provided are certain compounds or pharmaceutically acceptable salts thereof which can inhibit kinase activity of Bruton's tyrosine kinase (BTK) and may be useful for the treatment of diseases like cancer, immunological disease and inflammation.

BACKGROUND OF THE INVENTION

Hyper-proliferative diseases like cancer and inflammation are attracting the scientific community to provide therapeutic benefits. In this regard efforts have been made to identify and target specific mechanisms which play a role in proliferating the diseases.

Bruton's tyrosine kinase (BTK) is a member of Tec family of non-receptor tyrosine kinase expressed in B cells and myeloid cells, and it plays critical roles in B-cell receptor (BCR) signaling pathways, which is involved in early B-cell development, as well as mature B-cell activation, signaling and survival.

Functional mutations in human BTK are known to lead to X-linked agammaglobulinemia (XLA), an immunodeficiency disease related to a failure to generate mature B cells leading to reduced immunoglobulin in serum. In addition, regulation of BTK may affect BCR-induced production of pro-inflammatory cytokines and chemokines by B cells, indicating a broad potential for BTK in the treatment of autoimmune diseases. Evidence for a role for BTK in autoimmune and inflammatory diseases has also been provided by BTK-deficient mouse models. Thus, inhibition of BTK activity can be useful for the treatment of autoimmune and/or inflammatory diseases such as, rheumatoid arthritis, multiple vasculitides, myasthenia gravis, and asthma.

In addition, BTK has been reported to play an important role in apoptosis. In certain malignancies, BTK is overexpressed in B-cells, and it's associated with the increased proliferation and survival of tumor cells. Inhibition of BTK affects the B-cell signaling pathways, preventing activation of B-cells and inhibiting the growth of malignant B-cells.

Thus, inhibition of BTK activity can be useful for the treatment of cancer, as well as the treatment of B-cell lymphoma, leukemia, and other hematological malignancies. A number of clinical trials have shown that BTK inhibitors are effective against cancer. The first-in-class BTK inhibitor, ibrutinib (PCI-32765) was approved by US Food and Drug Administration for the treatment of patients with mantle cell lymphoma (MCL) or chronic lymphocytic leukemia (CLL). BTK inhibitor could also be used to treat other conditions such as immunological diseases and inflammations.

Therefore, a compound having an inhibitory activity on BTK will be useful for the prevention or treatment of diseases previously described. Although BTK inhibitors were disclosed in the arts, e.g., WO 2008039218 and WO 2008121742, many suffer from having short half-life or toxicity. Therefore, there is a need for new BTK inhibitors that have at least one advantageous property selected from potency, stability, selectivity, toxicity, pharmacodynamic and pharmacokinetic properties as an alternative for the treatment of hyper-proliferative diseases. In this regard, a novel class of BTK inhibitors is provided herein.

DISCLOSURE OF THE INVENTION

Disclosed herein are certain novel substituted pyrrolo[2,3-d]pyridazin-4-ones and pyrazolo[3,4-d]pyridazin-4-ones and pharmaceutical compositions thereof, and their use as pharmaceuticals.

In one aspect, disclosed herein is a compound of formula (II):

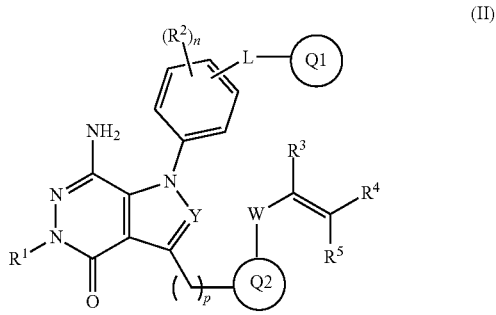

or a pharmaceutically acceptable salt thereof, wherein:

Ring Q1 is selected from aryl and heteroaryl, wherein aryl and heteroaryl are each unsubstituted or substituted with at least one substituent, such as one, two, three or four substituents, independently selected from $R^X$;

Ring Q2 is selected from $C_{3-10}$ cycloalkyl, heterocyclyl, aryl and heteroaryl, wherein cycloalkyl, heterocyclyl, aryl and heteroaryl are each unsubstituted or substituted with at least one substituent, such as one, two, three or four substituents, independently selected from $R^X$;

L is selected from a bond, $-(CR^{C1}R^{D1})_t-$, $-C(O)-$, $-O-$, $-(CR^{C1}R^{D1})_tO-$, $-O(CR^{C1}R^{D1})_t-$, $-S-$, $-S(O)_r-$, $-(CR^{C1}R^{D1})_tS-$, $-S(CR^{C1}R^{D1})_t-$, $-N(R^{A1})-$, $-N(R^{A1})C(O)-$, $-C(O)N(R^{A1})-$, $-N(R^{A1})C(O)O-$, $-OC(O)N(R^{A1})-$, $-N(R^{A1})C(O)N(R^{B1})-$, $-N(R^{A1})S(O)_2-$, $-S(O)_2N(R^{A1})-$ and $-N(R^{A1})S(O)_2N(R^{B1})-$;

W is selected from $-C(O)-$, $-OC(O)-$, $-NR^{A1}C(O)-$, $-C(=S)-$, $-S(O)_r-$, $-OS(O)_r-$ and $-N(R^{A1})S(O)_r-$;

Y is selected from N and $CR^6$;

$R^1$ is selected from hydrogen, $C_{1-10}$ alkyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, wherein alkyl, cycloalkyl, heterocyclyl, aryl and heteroaryl are each unsubstituted or substituted with at least one substituent, such as one, two, three or four substituents, independently selected from $R^X$;

each $R^2$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, NO$_2$, —NR$^{A2}$R$^{B2}$, —OR$^{A2}$, —C(O)R$^{A2}$, —C(=NR$^{E2}$)R$^{A2}$, —C(=N—OR$^{B2}$)R$^{A2}$, —C(O)OR$^{A2}$, —OC(O)R$^{A2}$, —C(O)NR$^{A2}$R$^{B2}$, —NR$^{A2}$C(O)R$^{B2}$, —C(=NR$^{E2}$)NR$^{A2}$R$^{B2}$, —NR$^{A2}$C(=NR$^{E2}$)R$^{B2}$, —OC(O)NR$^{A2}$R$^{B2}$, —NR$^{A2}$C(O)OR$^{B2}$, —NR$^{A2}$C(O)NR$^{A2}$R$^{B2}$, —NR$^{A2}$C(S)NR$^{A2}$R$^{B2}$, —NR$^{A2}$C(=NR$^{E2}$)NR$^{A2}$R$^{B2}$, —S(O)$_r$R$^{A2}$, —S(O)(=NR$^{E2}$)R$^{B2}$, —N=S(O)R$^{A2}$R$^{B2}$, —S(O)$_2$OR$^{A2}$, —OS(O)$_2$R$^{A2}$, —NR$^{A2}$S(O)$_r$R$^{B2}$, —NR$^{A2}$S(O)(=NR$^{E2}$)R$^{B2}$, —S(O)$_r$NR$^{A2}$R$^{B2}$, —S(O)(=NR$^{E2}$)NR$^{A2}$R$^{B2}$, —NR$^{A2}$S(O)$_2$NR$^{A2}$R$^{B2}$, —NR$^{A2}$S(O)(=NR$^{E2}$)NR$^{A2}$R$^{B2}$, —P(O)R$^{A2}$R$^{B2}$ and —P(O)(OR$^{A2}$)(OR$^{B2}$), wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

$R^3$ is selected from hydrogen, halogen, $C_{1-10}$ alkyl, $C_{3-10}$ cycloalkyl, $C_{3-10}$ cycloalkyl-$C_{1-4}$ alkyl, heterocyclyl and heterocyclyl-$C_{1-4}$ alkyl, wherein alkyl, cycloalkyl and heterocyclyl, are each unsubstituted or substituted with at least one substituent, such as one, two, three or four substituents, independently selected from $R^X$;

$R^5$ is selected from hydrogen, halogen, $C_{1-10}$ alkyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, cycloalkyl, heterocyclyl, aryl and heteroaryl are each unsubstituted or substituted with at least one substituent, such as one, two, three or four substituents, independently selected from $R^X$;

$R^4$ is selected from hydrogen, halogen, $C_{1-10}$ alkyl, $C_{3-10}$ cycloalkyl, $C_{3-10}$ cycloalkyl-$C_{1-4}$ alkyl, heterocyclyl and heterocyclyl-$C_{1-4}$ alkyl, wherein alkyl, cycloalkyl and heterocyclyl, are each unsubstituted or substituted with at least one substituent, such as one, two, three or four substituents, independently selected from $R^X$;

or $R^3$ and $R^4$ taken together form a bond;

$R^6$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, NO$_2$, —NR$^{A3}$R$^{B3}$, —OR$^{A3}$, —C(O)R$^{A3}$, —C(=NR$^{E3}$)R$^{A3}$, —C(=N—OR$^{B3}$)R$^{A3}$, —C(O)OR$^{A3}$, —OC(O)R$^{A3}$, —C(O)NR$^{A3}$R$^{B3}$, —NR$^{A3}$C(O)R$^{B3}$, —C(=NR$^{E3}$)NR$^{A3}$R$^{B3}$, —NR$^{A3}$C(=NR$^{E3}$)R$^{B3}$, —OC(O)NR$^{A3}$R$^{B3}$, —NR$^{A3}$C(O)OR$^{B3}$, —NR$^{A3}$C(O)NR$^{A3}$R$^{B3}$, —NR$^{A3}$C(S)NR$^{A3}$R$^{B3}$, —NR$^{A3}$C(=NR$^{E3}$)NR$^{A3}$R$^{B3}$, —S(O)$_r$R$^{A3}$, —S(O)(=NR$^{E3}$)R$^{B3}$, —N=S(O)R$^{A3}$R$^{B3}$, —S(O)$_2$OR$^{A3}$, —OS(O)$_2$R$^{A3}$, —NR$^{A3}$S(O)$_r$R$^{B3}$, —NR$^{A3}$S(O)(=NR$^{E3}$)R$^{B3}$, —S(O)$_r$NR$^{A3}$R$^{B3}$, —S(O)(=NR$^{E3}$)NR$^{A3}$R$^{B3}$, —NR$^{A3}$S(O)$_2$NR$^{A3}$R$^{B3}$, —NR$^{A3}$S(O)(=NR$^{E3}$)NR$^{A3}$R$^{B3}$, —P(O)R$^{A3}$R$^{B3}$ and —P(O)(OR$^{A3}$)(OR$^{B3}$), wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

each $R^{A1}$, $R^{A2}$, $R^{A3}$, $R^{B1}$, $R^{B2}$ and $R^{B3}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

or each "$R^{A1}$ and $R^{B1}$", "$R^{A2}$ and $R^{B2}$" or "$R^{A3}$ and $R^{B3}$" together with the atom(s) to which they are attached form a heterocyclic ring of 4 to 12 members containing 0, 1 or 2 additional heteroatoms independently selected from oxygen, sulfur and nitrogen, and optionally substituted with 1, 2 or 3 $R^X$ groups;

each $R^{C1}$ and $R^{D1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

or $R^{C1}$ and $R^{D1}$ together with the carbon atom(s) to which they are attached form a ring of 3 to 12 members containing 0, 1 or 2 heteroatoms independently selected from oxygen, sulfur and nitrogen and optionally substituted with 1 2 or 3 $R^X$ groups;

each $R^{E2}$ and $R^{E3}$ are independently selected from hydrogen, $C_{1-10}$ alkyl, CN, NO$_2$, —OR$^{a1}$, —SR$^{a1}$, —S(O)$_r$R$^{a1}$, —C(O)R$^{a1}$, —C(O)OR$^{a1}$, —C(O)NR$^{a1}$R$^{b1}$ and —S(O)$_r$NR$^{a1}$R$^{b1}$;

each $R^X$ is independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, NO$_2$, —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$C(O)R$^{a1}$, —(CR$^{c1}$R$^{d1}$)$_t$C(=NR$^{e1}$)R$^{a1}$, —(CR$^{c1}$R$^{d1}$)$_t$C(=N—OR$^{b1}$)R$^{a1}$, —(CR$^{c1}$R$^{d1}$)$_t$C(O)OR$^{b1}$, —(CR$^{c1}$R$^{d1}$)$_t$OC(O)R$^{b1}$, —(CR$^{c1}$R$^{d1}$)$_t$C(O)NR$^{a1}$R$^{b1}$, —(CR$^{c1}$R$^{d1}$)$_t$NR$^{a1}$C(O)R$^{b1}$, —(CR$^{c1}$R$^{d1}$)$_t$C(=NR$^{e1}$)NR$^{a1}$R$^{b1}$, —(CR$^{c1}$R$^{d1}$)$_t$NR$^{a1}$C(=NR$^{e1}$)R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)OR$^{b1}$, —(CR$^{c1}$R$^{d1}$)$_t$NR$^{a1}$C(O)NR$^{a1}$R$^{b1}$, —(CR$^{c1}$R$^{d1}$)$_t$NR$^{a1}$C(S)NR$^{a1}$R$^{b1}$, —(CR$^{c1}$R$^{d1}$)$_t$NR$^{a1}$C(=NR$^{e1}$)NR$^{a1}$R$^{b1}$, —(CR$^{c1}$R$^{d1}$)$_t$S(O)$_r$R$^{b1}$, —(CR$^{c1}$R$^{d1}$)$_t$S(O)(=NR$^{e1}$)R$^{b1}$, —(CR$^{c1}$R$^{d1}$)$_t$N=S(O)R$^{a1}$R$^{b1}$, —(CR$^{c1}$R$^{d1}$)$_t$S(O)$_2$OR$^{b1}$, —(CR$^{c1}$R$^{d1}$)$_t$OS(O)$_2$R$^{b1}$, —(CR$^{c1}$R$^{d1}$)$_t$NR$^{a1}$S(O)$_r$R$^{b1}$, —(CR$^{c1}$R$^{d1}$)$_t$NR$^{a1}$S(O)(=NR$^{e1}$)R$^{b1}$, —(CR$^{c1}$R$^{d1}$)$_t$S(O)$_r$NR$^{a1}$R$^{b1}$, —(CR$^{c1}$R$^{d1}$)$_t$S(O)(=NR$^{e1}$)NR$^{a1}$R$^{b1}$, —(CR$^{c1}$R$^{d1}$)$_t$NR$^{a1}$S(O)$_2$NR$^{a1}$R$^{b1}$, —(CR$^{c1}$R$^{d1}$)$_t$NR$^{a1}$S(O)(=NR$^{e1}$)NR$^{a1}$R$^{b1}$, —(CR$^{c1}$R$^{d1}$)$_t$P(O)R$^{a1}$R$^{b1}$ and —(CR$^{c1}$R$^{d1}$)$_t$P(O)(OR$^{a1}$)(OR$^{b1}$), wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

or $R^{a1}$ and $R^{b1}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1, 2 or 3 $R^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

or $R^{c1}$ and $R^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, CN, $NO_2$, $-OR^{a2}$, $-SR^{a2}$, $-S(O)_rR^{a2}$, $-C(O)R^{a2}$, $-C(O)OR^{a2}$, $-S(O)_rNR^{a2}R^{b2}$ and $-C(O)NR^{a2}R^{b2}$;

each $R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, $NO_2$, $-(CR^{c2}R^{d2})_tNR^{a2}R^{b2}$, $-(CR^{c2}R^{d2})_tOR^{b2}$, $-(CR^{c2}R^{d2})_tC(O)R^{a2}$, $-(CR^{c2}R^{d2})_tC(=NR^{e2})R^{a2}$, $-(CR^{c2}R^{d2})_tC(=N-OR^{b2})R^{a2}$, $-(CR^{c2}R^{d2})_tC(O)OR^{b2}$, $-(CR^{c2}R^{d2})_tOC(O)R^{b2}$, $-(CR^{c2}R^{d2})_tC(O)NR^{a2}R^{b2}$, $-(CR^{c2}R^{d2})_tNR^{a2}C(O)R^{b2}$, $-(CR^{c2}R^{d2})_tC(=NR^{e2})NR^{a2}R^{b2}$, $-(CR^{c2}R^{d2})_tNR^{a2}C(=NR^{e2})R^{b2}$, $-(CR^{c2}R^{d2})_tOC(O)NR^{a2}R^{b2}$, $-(CR^{c2}R^{d2})_tNR^{a2}C(O)OR^{b2}$, $-(CR^{c2}R^{d2})_tNR^{a2}C(O)NR^{a2}R^{b2}$, $-(CR^{c2}R^{d2})_tNR^{a2}C(S)NR^{a2}R^{b2}$, $-(CR^{c2}R^{d2})_tNR^{a2}C(=NR^{e2})NR^{a2}R^{b2}$, $-(CR^{c2}R^{d2})_tS(O)_rR^{b2}$, $-(CR^{c2}R^{d2})_tS(O)(=NR^{e2})R^{b2}$, $-(CR^{c2}R^{d2})_tN=S(O)R^{a2}R^{b2}$, $-(CR^{c2}R^{d2})_tS(O)_2OR^{b2}$, $-(CR^{c2}R^{d2})_tOS(O)_2R^{b2}$, $-(CR^{c2}R^{d2})_tNR^{a2}S(O)_rR^{b2}$, $-(CR^{c2}R^{d2})_tNR^{a2}S(O)(=NR^{e2})R^{b2}$, $-(CR^{c2}R^{d2})_tS(O)_tNR^{a2}R^{b2}$, $-(CR^{c2}R^{d2})_tS(O)(=NR^{e2})NR^{a2}R^{b2}$, $-(CR^{c2}R^{d2})_tNR^{a2}S(O)_2NR^{a2}R^{b2}$, $-(CR^{c2}R^{d2})_tNR^{a2}S(O)(=NR^{e2})NR^{a2}R^{b2}$, $-(CR^{c2}R^{d2})_tP(O)R^{a2}R^{b2}$ and $-(CR^{c2}R^{d2})_tP(O)(OR^{a2})(OR^{b2})$, wherein alkyl, alkenyl, alkynyl, cycloalkyl, heterocyclyl, aryl and heteroaryl are each unsubstituted or substituted with at least one substituent, such as one, two, three or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl) amino;

or $R^{c2}$ and $R^{d2}$ together with the carbon atom(s) to which they are attached form a ring of 3 to 12 members containing 0, 1 or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $-C(O)C_{1-4}$ alkyl, $-C(O)C_{3-10}$ cycloalkyl, $-C(O)OC_{1-4}$ alkyl, $-C(O)OC_{3-10}$ cycloalkyl, $-C(O)N(C_{1-4}$ alkyl$)_2$, $-C(O)N(C_{3-10}$ cycloalkyl$)_2$, $-S(O)_2C_{1-4}$ alkyl, $-S(O)_2C_{3-10}$ cycloalkyl, $-S(O)_2N(C_{1-4}$ alkyl$)_2$ and $-S(O)_2N(C_{3-10}$ cycloalkyl$)_2$;

n is selected from 0, 1, 2, 3 and 4;

p is selected from 0, 1 and 2;

each r is independently selected from 1 and 2;

each t is independently selected from 1, 2, 3 and 4.

In some embodiments, L is selected from $-O-$, $-S-$, and $-C(O)N(R^{A1})-$.

In some embodiments, L is $-O-$.

In some embodiments, L is $-C(O)N(R^{A1})-$.

In some embodiments, L is $-C(O)NH-$.

In some embodiments, Ring Q1 is aryl, wherein aryl is unsubstituted or substituted with at least one substituent independently selected from $R^X$.

In some embodiments, Ring Q1 is phenyl, wherein phenyl is unsubstituted or substituted with at least one substituent independently selected from $R^X$.

In some embodiments, Ring Q1 is phenyl, wherein phenyl is unsubstituted or substituted with at least one substituent independently selected from halogen.

In some embodiments, Ring Q1 is phenyl, wherein phenyl is unsubstituted or substituted with at least one fluorine.

In some embodiments, Ring Q1 is heteroaryl, wherein heteroaryl is unsubstituted or substituted with at least one substituent independently selected from $R^X$.

In some embodiments, Ring Q1 is pyridinyl, wherein pyridinyl is unsubstituted or substituted with at least one substituent independently selected from $R^X$.

In some embodiments, the substructure

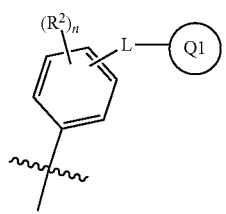

in Formula (II) is

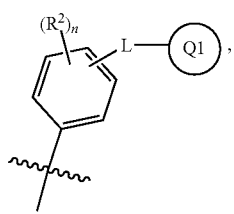

wherein the ⁓ symbol indicates the point of attachment to the rest of the molecule.

In some embodiments, $R^1$ is hydrogen.
In some embodiments, $R^2$ is hydrogen.
In some embodiments, p is 0.
In some embodiments, Ring Q2 is heterocyclyl, wherein heterocyclyl is unsubstituted or substituted with at least one substituent independently selected from $R^X$;
In some embodiments, Ring Q2 is selected from azetidinyl, pyrrolidinyl and piperidinyl, wherein azetidinyl, pyrrolidinyl and piperidinyl are each unsubstituted or substituted with at least one substituent independently selected from $R^X$;
In some embodiments, Ring Q2 is selected from azetidinyl, pyrrolidinyl and piperidinyl.
In some embodiments, W is —C(O)—.
In some embodiments, $R^3$, $R^4$ and $R^5$ are hydrogen.
In some embodiments, $R^3$ and $R^4$ taken together form a bond, and $R^5$ is $C_{1-10}$ alkyl.
In some embodiments, $R^3$ and $R^4$ taken together form a bond, and $R^5$ is methyl.
In some embodiments, Y is N.
In some embodiments, Y is $CR^6$.
In some embodiments, $R^6$ is hydrogen.
Also provided is a compound, selected from
3-(1-acryloylpyrrolidin-3-yl)-7-amino-1-(4-phenoxyphenyl)-1,5-dihydro-4H-pyrrolo[2,3-d]pyridazin-4-one,
7-amino-3-(1-(but-2-ynoyl)pyrrolidin-3-yl)-1-(4-phenoxyphenyl)-1,5-dihydro-4H-pyrrolo[2,3-d]pyridazin-4-one,
3-(1-acryloylpyrrolidin-3-yl)-7-amino-1-(4-(2,6-difluorophenoxy)phenyl)-1,5-dihydro-4H-pyrrolo[2,3-d]pyridazin-4-one,
7-amino-3-(1-(but-2-ynoyl)pyrrolidin-3-yl)-1-(4-(2,6-difluorophenoxy)phenyl)-1,5-dihydro-4H-pyrrolo[2,3-d]pyridazin-4-one,
3-(1-acryloylpyrrolidin-3-yl)-7-amino-1-(4-phenoxyphenyl)-1,5-dihydro-4H-pyrazolo[3,4-d]pyridazin-4-one,
7-amino-3-(1-(but-2-ynoyl)pyrrolidin-3-yl)-1-(4-phenoxyphenyl)-1,5-dihydro-4H-pyrazolo[3,4-d]pyridazin-4-one,
3-(1-acryloylpyrrolidin-3-yl)-7-amino-1-(4-(2,6-difluorophenoxy)phenyl)-1,5-dihydro-4H-pyrazolo[3,4-d]pyridazin-4-one,
7-amino-3-(1-(but-2-ynoyl)pyrrolidin-3-yl)-1-(4-(2,6-difluorophenoxy)phenyl)-1,5-dihydro-4H-pyrazolo[3,4-d]pyridazin-4-one,
(S)-3-(1-acryloylpyrrolidin-3-yl)-7-amino-1-(4-phenoxyphenyl)-1,5-dihydro-4H-pyrrolo[2,3-d]pyridazin-4-one,
(R)-3-(1-acryloylpyrrolidin-3-yl)-7-amino-1-(4-phenoxyphenyl)-1,5-dihydro-4H-pyrrolo[2,3-d]pyridazin-4-one,
(S)-3-(1-acryloylpiperidin-3-yl)-7-amino-1-(4-phenoxyphenyl)-1,5-dihydro-4H-pyrrolo[2,3-d]pyridazin-4-one,
(R)-3-(1-acryloylpiperidin-3-yl)-7-amino-1-(4-phenoxyphenyl)-1,5-dihydro-4H-pyrrolo[2,3-d]pyridazin-4-one,
(R)-3-(1-acryloylpyrrolidin-3-yl)-7-amino-1-(4-phenoxyphenyl)-1,5-dihydro-4H-pyrazolo[3,4-d]pyridazin-4-one,
(S)-3-(1-acryloylpyrrolidin-3-yl)-7-amino-1-(4-phenoxyphenyl)-1,5-dihydro-4H-pyrazolo[3,4-d]pyridazin-4-one,
(R)-3-(1-acryloylpiperidin-3-yl)-7-amino-1-(4-phenoxyphenyl)-1,5-dihydro-4H-pyrazolo[3,4-d]pyridazin-4-one,
(S)-3-(1-acryloylpiperidin-3-yl)-7-amino-1-(4-phenoxyphenyl)-1,5-dihydro-4H-pyrazolo[3,4-d]pyridazin-4-one,
(S)-3-(1-acryloylpyrrolidin-3-yl)-7-amino-1-(4-(2-fluorophenoxy)phenyl)-1,5-dihydro-4H-pyrrolo[2,3-d]pyridazin-4-one,
(S)-3-(1-acryloylpyrrolidin-3-yl)-7-amino-1-(4-(3-fluorophenoxy)phenyl)-1,5-dihydro-4H-pyrrolo[2,3-d]pyridazin-4-one,
(S)-3-(1-acryloylpyrrolidin-3-yl)-7-amino-1-(4-(4-fluorophenoxy)phenyl)-1,5-dihydro-4H-pyrrolo[2,3-d]pyridazin-4-one,
(S)-3-(1-acryloylpyrrolidin-3-yl)-7-amino-1-(4-(2,3-difluorophenoxy)phenyl)-1,5-dihydro-4H-pyrrolo[2,3-d]pyridazin-4-one,
(S)-3-(1-acryloylpyrrolidin-3-yl)-7-amino-1-(4-(2,6-difluorophenoxy)phenyl)-1,5-dihydro-4H-pyrrolo[2,3-d]pyridazin-4-one,
(S)-3-(1-acryloylpyrrolidin-3-yl)-7-amino-1-(4-(3,5-difluorophenoxy)phenyl)-1,5-dihydro-4H-pyrrolo[2,3-d]pyridazin-4-one,
(R)-3-(1-acryloylpyrrolidin-3-yl)-7-amino-1-(4-(2-fluorophenoxy)phenyl)-1,5-dihydro-4H-pyrrolo[2,3-d]pyridazin-4-one,
(R)-3-(1-acryloylpyrrolidin-3-yl)-7-amino-1-(4-(3-fluorophenoxy)phenyl)-1,5-dihydro-4H-pyrrolo[2,3-d]pyridazin-4-one,
(R)-3-(1-acryloylpyrrolidin-3-yl)-7-amino-1-(4-(4-fluorophenoxy)phenyl)-1,5-dihydro-4H-pyrrolo[2,3-d]pyridazin-4-one,
(R)-3-(1-acryloylpyrrolidin-3-yl)-7-amino-1-(4-(2,3-difluorophenoxy)phenyl)-1,5-dihydro-4H-pyrrolo[2,3-d]pyridazin-4-one,
(R)-3-(1-acryloylpyrrolidin-3-yl)-7-amino-1-(4-(2,6-difluorophenoxy)phenyl)-1,5-dihydro-4H-pyrrolo[2,3-d]pyridazin-4-one,
(R)-3-(1-acryloylpyrrolidin-3-yl)-7-amino-1-(4-(3,5-difluorophenoxy)phenyl)-1,5-dihydro-4H-pyrrolo[2,3-d]pyridazin-4-one, (S)-3-(1-acryloylpiperidin-3-yl)-7-amino-1-(4-(2-fluorophenoxy)phenyl)-1,5-dihydro-4H-pyrrolo[2,3-d]pyridazin-4-one,
(S)-3-(1-acryloylpiperidin-3-yl)-7-amino-1-(4-(3-fluorophenoxy)phenyl)-1,5-dihydro-4H-pyrrolo[2,3-d]pyridazin-4-one,
(S)-3-(1-acryloylpiperidin-3-yl)-7-amino-1-(4-(4-fluorophenoxy)phenyl)-1,5-dihydro-4H-pyrrolo[2,3-d]pyridazin-4-one,
(S)-3-(1-acryloylpiperidin-3-yl)-7-amino-1-(4-(2,3-difluorophenoxy)phenyl)-1,5-dihydro-4H-pyrrolo[2,3-d]pyridazin-4-one,
(S)-3-(1-acryloylpiperidin-3-yl)-7-amino-1-(4-(2,6-difluorophenoxy)phenyl)-1,5-dihydro-4H-pyrrolo[2,3-d]pyridazin-4-one,
(S)-3-(1-acryloylpiperidin-3-yl)-7-amino-1-(4-(3,5-difluorophenoxy)phenyl)-1,5-dihydro-4H-pyrrolo[2,3-d]pyridazin-4-one,
(R)-3-(1-acryloylpiperidin-3-yl)-7-amino-1-(4-(2-fluorophenoxy)phenyl)-1,5-dihydro-4H-pyrrolo[2,3-d]pyridazin-4-one,
(R)-3-(1-acryloylpiperidin-3-yl)-7-amino-1-(4-(3-fluorophenoxy)phenyl)-1,5-dihydro-4H-pyrrolo[2,3-d]pyridazin-4-one,
(R)-3-(1-acryloylpiperidin-3-yl)-7-amino-1-(4-(4-fluorophenoxy)phenyl)-1,5-dihydro-4H-pyrrolo[2,3-d]pyridazin-4-one,
(R)-3-(1-acryloylpiperidin-3-yl)-7-amino-1-(4-(2,3-difluorophenoxy)phenyl)-1,5-dihydro-4H-pyrrolo[2,3-d]pyridazin-4-one,
(R)-3-(1-acryloylpiperidin-3-yl)-7-amino-1-(4-(2,6-difluorophenoxy)phenyl)-1,5-dihydro-4H-pyrrolo[2,3-d]pyridazin-4-one,
(R)-3-(1-acryloylpiperidin-3-yl)-7-amino-1-(4-(3,5-difluorophenoxy)phenyl)-1,5-dihydro-4H-pyrrolo[2,3-d]pyridazin-4-one,
(R)-3-(1-acryloylpyrrolidin-3-yl)-7-amino-1-(4-(2-fluorophenoxy)phenyl)-1,5-dihydro-4H-pyrazolo[3,4-d]pyridazin-4-one,
(R)-3-(1-acryloylpyrrolidin-3-yl)-7-amino-1-(4-(3-fluorophenoxy)phenyl)-1,5-dihydro-4H-pyrazolo[3,4-d]pyridazin-4-one,
(R)-3-(1-acryloylpyrrolidin-3-yl)-7-amino-1-(4-(4-fluorophenoxy)phenyl)-1,5-dihydro-4H-pyrazolo[3,4-d]pyridazin-4-one,
(R)-3-(1-acryloylpyrrolidin-3-yl)-7-amino-1-(4-(2,3-difluorophenoxy)phenyl)-1,5-dihydro-4H-pyrazolo[3,4-d]pyridazin-4-one,
(R)-3-(1-acryloylpyrrolidin-3-yl)-7-amino-1-(4-(2,6-difluorophenoxy)phenyl)-1,5-dihydro-4H-pyrazolo[3,4-d]pyridazin-4-one,
(R)-3-(1-acryloylpyrrolidin-3-yl)-7-amino-1-(4-(3,5-difluorophenoxy)phenyl)-1,5-dihydro-4H-pyrazolo[3,4-d]pyridazin-4-one,
(S)-3-(1-acryloylpyrrolidin-3-yl)-7-amino-1-(4-(2-fluorophenoxy)phenyl)-1,5-dihydro-4H-pyrazolo[3,4-d]pyridazin-4-one,
(S)-3-(1-acryloylpyrrolidin-3-yl)-7-amino-1-(4-(3-fluorophenoxy)phenyl)-1,5-dihydro-4H-pyrazolo[3,4-d]pyridazin-4-one,
(S)-3-(1-acryloylpyrrolidin-3-yl)-7-amino-1-(4-(4-fluorophenoxy)phenyl)-1,5-dihydro-4H-pyrazolo[3,4-d]pyridazin-4-one,
(S)-3-(1-acryloylpyrrolidin-3-yl)-7-amino-1-(4-(2,3-difluorophenoxy)phenyl)-1,5-dihydro-4H-pyrazolo[3,4-d]pyridazin-4-one,
(S)-3-(1-acryloylpyrrolidin-3-yl)-7-amino-1-(4-(2,6-difluorophenoxy)phenyl)-1,5-dihydro-4H-pyrazolo[3,4-d]pyridazin-4-one,
(S)-3-(1-acryloylpyrrolidin-3-yl)-7-amino-1-(4-(3,5-difluorophenoxy)phenyl)-1,5-dihydro-4H-pyrazolo[3,4-d]pyridazin-4-one,
(R)-3-(1-acryloylpiperidin-3-yl)-7-amino-1-(4-(2-fluorophenoxy)phenyl)-1,5-dihydro-4H-pyrazolo[3,4-d]pyridazin-4-one,
(R)-3-(1-acryloylpiperidin-3-yl)-7-amino-1-(4-(3-fluorophenoxy)phenyl)-1,5-dihydro-4H-pyrazolo[3,4-d]pyridazin-4-one,
(R)-3-(1-acryloylpiperidin-3-yl)-7-amino-1-(4-(4-fluorophenoxy)phenyl)-1,5-dihydro-4H-pyrazolo[3,4-d]pyridazin-4-one,
(R)-3-(1-acryloylpiperidin-3-yl)-7-amino-1-(4-(2,3-difluorophenoxy)phenyl)-1,5-dihydro-4H-pyrazolo[3,4-d]pyridazin-4-one,
(R)-3-(1-acryloylpiperidin-3-yl)-7-amino-1-(4-(2,6-difluorophenoxy)phenyl)-1,5-dihydro-4H-pyrazolo[3,4-d]pyridazin-4-one,
(R)-3-(1-acryloylpiperidin-3-yl)-7-amino-1-(4-(3,5-difluorophenoxy)phenyl)-1,5-dihydro-4H-pyrazolo[3,4-d]pyridazin-4-one,
(S)-3-(1-acryloylpiperidin-3-yl)-7-amino-1-(4-(2-fluorophenoxy)phenyl)-1,5-dihydro-4H-pyrazolo[3,4-d]pyridazin-4-one,
(S)-3-(1-acryloylpiperidin-3-yl)-7-amino-1-(4-(3-fluorophenoxy)phenyl)-1,5-dihydro-4H-pyrazolo[3,4-d]pyridazin-4-one,
(S)-3-(1-acryloylpiperidin-3-yl)-7-amino-1-(4-(4-fluorophenoxy)phenyl)-1,5-dihydro-4H-pyrazolo[3,4-d]pyridazin-4-one,
(S)-3-(1-acryloylpiperidin-3-yl)-7-amino-1-(4-(2,3-difluorophenoxy)phenyl)-1,5-dihydro-4H-pyrazolo[3,4-d]pyridazin-4-one,
(S)-3-(1-acryloylpiperidin-3-yl)-7-amino-1-(4-(2,6-difluorophenoxy)phenyl)-1,5-dihydro-4H-pyrazolo[3,4-d]pyridazin-4-one,
(S)-3-(1-acryloylpiperidin-3-yl)-7-amino-1-(4-(3,5-difluorophenoxy)phenyl)-1,5-dihydro-4H-pyrazolo[3,4-d]pyridazin-4-one,
(R)-7-amino-3-(1-(but-2-ynoyl)pyrrolidin-3-yl)-1-(4-phenoxyphenyl)-1,5-dihydro-4H-pyrazolo[3,4-d]pyridazin-4-one,
(S)-7-amino-3-(1-(but-2-ynoyl)pyrrolidin-3-yl)-1-(4-phenoxyphenyl)-1,5-dihydro-4H-pyrazolo[3,4-d]pyridazin-4-one,
(S)-7-amino-3-(1-(but-2-ynoyl)pyrrolidin-3-yl)-1-(4-phenoxyphenyl)-1,5-dihydro-4H-pyrrolo[2,3-d]pyridazin-4-one,
(R)-7-amino-3-(1-(but-2-ynoyl)pyrrolidin-3-yl)-1-(4-phenoxyphenyl)-1,5-dihydro-4H-pyrrolo[2,3-d]pyridazin-4-one,
(R)-7-amino-3-(1-(but-2-ynoyl)piperidin-3-yl)-1-(4-phenoxyphenyl)-1,5-dihydro-4H-pyrazolo[3,4-d]pyridazin-4-one,
(S)-7-amino-3-(1-(but-2-ynoyl)piperidin-3-yl)-1-(4-phenoxyphenyl)-1,5-dihydro-4H-pyrazolo[3,4-d]pyridazin-4-one,
(S)-7-amino-3-(1-(but-2-ynoyl)piperidin-3-yl)-1-(4-phenoxyphenyl)-1,5-dihydro-4H-pyrrolo[2,3-d]pyridazin-4-one,
(R)-7-amino-3-(1-(but-2-ynoyl)piperidin-3-yl)-1-(4-phenoxyphenyl)-1,5-dihydro-4H-pyrrolo[2,3-d]pyridazin-4-one, (R)-7-amino-3-(1-(but-2-ynoyl)pyrrolidin-3-yl)-1-(4-(2-fluorophenoxy)phenyl)-1,5-dihydro-4H-pyrazolo[3,4-d]pyridazin-4-one,
(S)-7-amino-3-(1-(but-2-ynoyl)pyrrolidin-3-yl)-1-(4-(2-fluorophenoxy)phenyl)-1,5-dihydro-4H-pyrazolo[3,4-d]pyridazin-4-one,
(S)-7-amino-3-(1-(but-2-ynoyl)pyrrolidin-3-yl)-1-(4-(2-fluorophenoxy)phenyl)-1,5-dihydro-4H-pyrrolo[2,3-d]pyridazin-4-one,
(R)-7-amino-3-(1-(but-2-ynoyl)pyrrolidin-3-yl)-1-(4-(2-fluorophenoxy)phenyl)-1,5-dihydro-4H-pyrrolo[2,3-d]pyridazin-4-one,
(R)-7-amino-3-(1-(but-2-ynoyl)piperidin-3-yl)-1-(4-(2-fluorophenoxy)phenyl)-1,5-dihydro-4H-pyrazolo[3,4-d]pyridazin-4-one,
(S)-7-amino-3-(1-(but-2-ynoyl)piperidin-3-yl)-1-(4-(2-fluorophenoxy)phenyl)-1,5-dihydro-4H-pyrazolo[3,4-d]pyridazin-4-one,
(S)-7-amino-3-(1-(but-2-ynoyl)piperidin-3-yl)-1-(4-(2-fluorophenoxy)phenyl)-1,5-dihydro-4H-pyrrolo[2,3-d]pyridazin-4-one,
(R)-7-amino-3-(1-(but-2-ynoyl)piperidin-3-yl)-1-(4-(2-fluorophenoxy)phenyl)-1,5-dihydro-4H-pyrrolo[2,3-d]pyridazin-4-one,
(R)-7-amino-3-(1-(but-2-ynoyl)pyrrolidin-3-yl)-1-(4-(2,6-difluorophenoxy)phenyl)-1,5-dihydro-4H-pyrazolo[3,4-d]pyridazin-4-one,
(S)-7-amino-3-(1-(but-2-ynoyl)pyrrolidin-3-yl)-1-(4-(2,6-difluorophenoxy)phenyl)-1,5-dihydro-4H-pyrazolo[3,4-d]pyridazin-4-one,
(S)-7-amino-3-(1-(but-2-ynoyl)pyrrolidin-3-yl)-1-(4-(2,6-difluorophenoxy)phenyl)-1,5-dihydro-4H-pyrrolo[2,3-d]pyridazin-4-one,
(R)-7-amino-3-(1-(but-2-ynoyl)pyrrolidin-3-yl)-1-(4-(2,6-difluorophenoxy)phenyl)-1,5-dihydro-4H-pyrrolo[2,3-d]pyridazin-4-one,
(R)-7-amino-3-(1-(but-2-ynoyl)piperidin-3-yl)-1-(4-(2,6-difluorophenoxy)phenyl)-1,5-dihydro-4H-pyrazolo[3,4-d]pyridazin-4-one,
(S)-7-amino-3-(1-(but-2-ynoyl)piperidin-3-yl)-1-(4-(2,6-difluorophenoxy)phenyl)-1,5-dihydro-4H-pyrazolo[3,4-d]pyridazin-4-one,
(S)-7-amino-3-(1-(but-2-ynoyl)piperidin-3-yl)-1-(4-(2,6-difluorophenoxy)phenyl)-1,5-dihydro-4H-pyrrolo[2,3-d]pyridazin-4-one,
(R)-7-amino-3-(1-(but-2-ynoyl)piperidin-3-yl)-1-(4-(2,6-difluorophenoxy)phenyl)-1,5-dihydro-4H-pyrrolo[2,3-d]pyridazin-4-one,
(R)-4-(7-amino-3-(1-(but-2-ynoyl)pyrrolidin-3-yl)-4-oxo-4,5-dihydro-1H-pyrazolo[3,4-d]pyridazin-1-yl)-N-(pyridin-2-yl)benzamide,
(R)-4-(3-(1-acryloylpyrrolidin-3-yl)-7-amino-4-oxo-4,5-dihydro-1H-pyrazolo[3,4-d]pyridazin-1-yl)-N-(pyridin-2-yl)benzamide,
(S,E)-7-amino-3-(1-(4-methoxybut-2-enoyl)pyrrolidin-3-yl)-1-(4-phenoxyphenyl)-1,5-dihydro-4H-pyrrolo[2,3-d]pyridazin-4-one,
(S,E)-7-amino-1-(4-(2-fluorophenoxy)phenyl)-3-(1-(4-methoxybut-2-enoyl)pyrrolidin-3-yl)-1,5-dihydro-4H-pyrrolo[2,3-d]pyridazin-4-one,
(S,E)-7-amino-3-(1-(4-(dimethylamino)but-2-enoyl)pyrrolidin-3-yl)-1-(4-phenoxyphenyl)-1,5-dihydro-4H-pyrrolo[2,3-d]pyridazin-4-one,
(S,E)-7-amino-3-(1-(4-(dimethylamino)but-2-enoyl)pyrrolidin-3-yl)-1-(4-(2-fluorophenoxy)phenyl)-1,5-dihydro-4H-pyrrolo[2,3-d]pyridazin-4-one,
7-amino-3-((S)-1-((E)-3-((R)-azetidin-2-yl)acryloyl)pyrrolidin-3-yl)-1-(4-phenoxyphenyl)-1,5-dihydro-4H-pyrrolo[2,3-d]pyridazin-4-one,
7-amino-3-((S)-1-((E)-3-((R)-azetidin-2-yl)acryloyl)pyrrolidin-3-yl)-1-(4-(2-fluorophenoxy)phenyl)-1,5-dihydro-4H-pyrrolo[2,3-d]pyridazin-4-one,
7-amino-3-((S)-1-((E)-3-((R)-azetidin-2-yl)acryloyl)pyrrolidin-3-yl)-1-(4-phenoxyphenyl)-1,5-dihydro-4H-pyrrolo[2,3-d]pyridazin-4-one,
7-amino-1-(4-(2-fluorophenoxy)phenyl)-3-((S)-1-((E)-3-((R)-1-methylazetidin-2-yl)acryloyl)pyrrolidin-3-yl)-1,5-dihydro-4H-pyrrolo[2,3-d]pyridazin-4-one,
7-amino-3-((S)-1-((E)-3-((R)-1-ethylazetidin-2-yl)acryloyl)pyrrolidin-3-yl)-1-(4-phenoxyphenyl)-1,5-dihydro-4H-pyrrolo[2,3-d]pyridazin-4-one,
7-amino-3-((S)-1-((E)-3-((R)-1-ethylazetidin-2-yl)acryloyl)pyrrolidin-3-yl)-1-(4-(2-fluorophenoxy)phenyl)-1,5-dihydro-4H-pyrrolo[2,3-d]pyridazin-4-one,
(S,E)-7-amino-3-(1-(4-methoxybut-2-enoyl)piperidin-3-yl)-1-(4-phenoxyphenyl)-1,5-dihydro-4H-pyrrolo[2,3-d]pyridazin-4-one,
(S,E)-7-amino-1-(4-(2-fluorophenoxy)phenyl)-3-(1-(4-methoxybut-2-enoyl)piperidin-3-yl)-1,5-dihydro-4H-pyrrolo[2,3-d]pyridazin-4-one,
(S,E)-7-amino-3-(1-(4-(dimethylamino)but-2-enoyl)piperidin-3-yl)-1-(4-phenoxyphenyl)-1,5-dihydro-4H-pyrrolo[2,3-d]pyridazin-4-one,
(S,E)-7-amino-3-(1-(4-(dimethylamino)but-2-enoyl)piperidin-3-yl)-1-(4-(2-fluorophenoxy)phenyl)-1,5-dihydro-4H-pyrrolo[2,3-d]pyridazin-4-one,
7-amino-3-((S)-1-((E)-3-((R)-azetidin-2-yl)acryloyl)piperidin-3-yl)-1-(4-phenoxyphenyl)-1,5-dihydro-4H-pyrrolo[2,3-d]pyridazin-4-one,
7-amino-3-((S)-1-((E)-3-((R)-azetidin-2-yl)acryloyl)piperidin-3-yl)-1-(4-(2-fluorophenoxy)phenyl)-1,5-dihydro-4H-pyrrolo[2,3-d]pyridazin-4-one,
7-amino-3-((S)-1-((E)-3-((R)-1-methylazetidin-2-yl)acryloyl)piperidin-3-yl)-1-(4-phenoxyphenyl)-1,5-dihydro-4H-pyrrolo[2,3-d]pyridazin-4-one,
7-amino-1-(4-(2-fluorophenoxy)phenyl)-3-((S)-1-((E)-3-((R)-1-methylazetidin-2-yl)acryloyl)piperidin-3-yl)-1,5-dihydro-4H-pyrrolo[2,3-d]pyridazin-4-one,
7-amino-3-((S)-1-((E)-3-((R)-1-ethylazetidin-2-yl)acryloyl)piperidin-3-yl)-1-(4-phenoxyphenyl)-1,5-dihydro-4H-pyrrolo[2,3-d]pyridazin-4-one,
7-amino-3-((S)-1-((E)-3-((R)-1-ethylazetidin-2-yl)acryloyl)piperidin-3-yl)-1-(4-(2-fluorophenoxy)phenyl)-1,5-dihydro-4H-pyrrolo[2,3-d]pyridazin-4-one,
3-(1-acryloylazetidin-3-yl)-7-amino-1-(4-(2-fluorophenoxy)phenyl)-1,5-dihydro-4H-pyrrolo[2,3-d]pyridazin-4-one,
3-(1-acryloylpiperidin-4-yl)-7-amino-1-(4-phenoxyphenyl)-1,5-dihydro-4H-pyrrolo[2,3-d]pyridazin-4-one,
3-(1-acryloylpiperidin-4-yl)-7-amino-1-(4-(2-fluorophenoxy)phenyl)-1,5-dihydro-4H-pyrrolo[2,3-d]pyridazin-4-one,
3-(1-acryloylazetidin-3-yl)-7-amino-1-(4-phenoxyphenyl)-1,5-dihydro-4H-pyrrolo[2,3-d]pyridazin-4-one,
(S)-3-(1-acryloylpyrrolidin-3-yl)-7-amino-1-(4-(2,5-difluorophenoxy)phenyl)-1,5-dihydro-4H-pyrrolo[2,3-d]pyridazin-4-one,
(S)-3-(1-acryloylpyrrolidin-3-yl)-7-amino-1-(4-(2-fluorophenoxy-3-d)phenyl)-1,5-dihydro-4H-pyrrolo[2,3-d]pyridazin-4-one,
(S)-7-amino-3-(1-(but-2-ynoyl)pyrrolidin-3-yl)-1-(4-(2-fluorophenoxy-3-d)phenyl)-1,5-dihydro-4H-pyrrolo[2,3-d]pyridazin-4-one, or a pharmaceutically acceptable salt thereof.

In yet another aspect, the present disclosure provides pharmaceutical compositions comprising a compound of formula (II) or at least one pharmaceutically acceptable salt thereof and a pharmaceutically acceptable excipient.

In yet another aspect, the disclosure provides methods for modulating BTK, comprising administering to a system or a subject in need thereof, a therapeutically effective amount of a compound of formula (II) or a pharmaceutically acceptable salt thereof or pharmaceutical compositions thereof, thereby modulating said BTK.

In yet another aspect, disclosed is a method to treat, ameliorate or prevent a condition which responds to inhibition of BTK comprising administering to a system or subject in need of such treatment an effective amount of a compound of formula (II) or a pharmaceutically acceptable salt thereof or pharmaceutical compositions thereof, and optionally in combination with a second therapeutic agent, thereby treating said condition.

Alternatively, the present disclosure provides the use of a compound of formula (II) or a pharmaceutically acceptable salt thereof in the manufacture of a medicament for treating a condition mediated by BTK. In particular embodiments, the compounds of the disclosure may be used alone or in combination with a second therapeutic agent to treat a condition mediated by BTK.

Alternatively, disclosed is a compound of formula (II) or a pharmaceutical acceptable salt thereof for treating a condition mediated by BTK.

Specifically, the condition herein includes but not limited to, is an autoimmune disease, a heteroimmune disease, an allergic disease, an inflammatory disease or a cell proliferative disorder.

Furthermore, the disclosure provides methods for treating a condition mediated by BTK, comprising administering to a system or subject in need of such treatment an effective amount of a compound of formula (II) or a pharmaceutically acceptable salt thereof or pharmaceutical compositions thereof, and optionally in combination with a second therapeutic agent, thereby treating said condition.

Alternatively, the present disclosure provides the use of a compound of formula (II) or a pharmaceutically acceptable salt thereof in the manufacture of a medicament for treating a condition mediated by BTK. In particular examples, the compounds of the disclosure may be used alone or in combination with a chemotherapeutic agent to treat said condition.

Specifically, the condition herein includes but not limited to, is an autoimmune disease, a heteroimmune disease, an allergic disease, an inflammatory disease or a cell proliferative disorder.

In certain embodiments, the condition is cell proliferative disorder. In one embodiment, the cell proliferative disorder is B-cell proliferative disorder, which includes but not limited to, B-cell chronic lymphocytic lymphoma, chronic lymphocytic leukemia, B-cell prolymphocytic leukemia, lymphoplasmacytic lymphoma, multiple sclerosis, small lymphocytic lymphoma, mantle cell lymphoma, B-cell non-Hodgkin's lymphoma, activated B-cell like diffuse large B-cell lymphoma, multiple myeloma, diffuse large B-cell lymphoma, follicular lymphoma, primary effusion lymphoma, burkitt lymphoma/leukemia, lymphomatoid granulomatosis, and plasmacytoma.

In certain embodiments, the condition is autoimmune disease, which includes but not limited to, rheumatoid arthritis, psoriatic arthritis, psoriasis, osteoarthritis, juvenile arthritis, inflammatory bowel disease, Crohn's disease, ulcerative colitis, myasthenia gravis, Hashimoto's thyroiditis, multiple sclerosis, acute disseminated encephalomyelitis, Addison's disease, ankylosing spondylitis, antiphospholipid antibody syndrome, aplastic anemia, autoimmune hepatitis, coeliac disease, Goodpasture's syndrome, idiopathic thrombocytopenic purpura, scleroderma, primary biliary cirrhosis, Reiter's syndrome, psoriasis, dysautonomia, neuromyotonia, interstitial cystitis, lupus, systemic lupus erythematosus, and lupus nephritis.

In certain embodiments, the condition is heteroimmune disease, which includes but not limited to, graft versus host disease, transplantation, transfusion, anaphylaxis, allergy, type I hypersensitivity, allergic conjunctivitis, allergic rhinitis, and atopic dermatitis.

In certain embodiments, the condition is inflammatory disease, which includes but not limited to, athma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritic, phlebitis, pneumonitis, pneumonia, proctitis, prostatitis, pyelonephritis, rhinitis, salpingitis, sinusitis, stomatitis, synovitis, endonitis, tonsillitis, uveitis, vaginitis, vasculitis, and vulvitis.

In the above methods for using the compounds of the disclosure, a compound of formula (I) or a pharmaceutically acceptable salt thereof may be administered to a system comprising cells or tissues, or to a subject including a mammalian subject such as a human or animal subject.

Certain Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

The term "substituted" means that a hydrogen atom is removed and replaced by a substituent. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-10}$, $C_{3-10}$, and the like.

The term "hydrogen" refers to $^1H$, $^2H$ and $^3H$.

The term "alkyl", employed alone or in combination with other terms, refers to both branched and straight-chain saturated aliphatic hydrocarbon groups having the specified number of carbon atoms. Unless otherwise specified, "alkyl" refers to $C_{1-10}$ alkyl. For example, $C_{1-6}$, as in "$C_{1-6}$ alkyl" is defined to include groups having 1, 2, 3, 4, 5, or 6 carbons in a linear or branched arrangement. For example, "$C_{1-8}$ alkyl" includes but is not limited to methyl, ethyl, n-propyl, i-propyl, n-butyl, t-butyl, i-butyl, pentyl, hexyl, heptyl, and octyl.

The term "cycloalkyl", employed alone or in combination with other terms, refers to a monocyclic or bridged hydrocarbon ring system. The monocyclic cycloalkyl is a carbocyclic ring system containing three to ten carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.03,7]nonane, and tricyclo[3.3.1.13,7]decane (adamantane). The monocyclic and bridged cycloalkyl can be attached to the parent molecular moiety through any substitutable atom contained within the ring system.

The term "alkenyl", employed alone or in combination with other terms, refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl", employed alone or in combination with other terms, refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "halogen" (or "halo") refers to fluorine, chlorine, bromine and iodine.

The term "alkoxy", employed alone or in combination with other terms, refers to an alkyl radical that is single bonded to an oxygen atom. The attachment point of an alkoxy radical to a molecule is through the oxygen atom. An alkoxy radical may be depicted as —O-alkyl. The term "$C_{1-10}$ alkoxy" refers to an alkoxy radical containing from one to ten carbon atoms, having straight or branched moieties. Alkoxy groups, includes but is not limited to, methoxy, ethoxy, propoxy, isopropoxy, butoxy, pentyloxy, hexyloxy, and the like.

The term "cycloalkoxy", employed alone or in combination with other terms, refers to cycloalkyl radical that is single bonded to an oxygen atom. The attachment point of a cycloalkoxy radical to a molecule is through the oxygen atom. A cycloalkoxy radical may be depicted as —O-cycloalkyl. "$C_{3-10}$ cycloalkoxy" refers to a cycloalkoxy radical containing from three to ten carbon atoms. Cycloalkoxy groups, includes but is not limited to, cyclopropoxy, cyclobutoxy, cyclopentyloxy, cyclohexyloxy, and the like.

The term "alkylthio", employed alone or in combination with other terms, refers to an alkyl radical that is single bonded to a sulfur atom. The attachment point of an alkylthio radical to a molecule is through the sulfur atom. An alkylthio radical may be depicted as —S-alkyl. The term "$C_{1-10}$ alkylthio" refers to an alkylthio radical containing from one to ten carbon atoms, having straight or branched moieties. Alkylthio groups, includes but is not limited to, methylthio, ethylthio, propylthio, isopropylthio, butylthio, hexylthio, and the like.

The term "cycloalkylthio", employed alone or in combination with other terms, refers to cycloalkyl radical that is single bonded to a sulfur atom. The attachment point of a cycloalkylthio radical to a molecule is through the sulfur atom. A cycloalkylthio radical may be depicted as —S-cycloalkyl. "$C_{3-10}$ cycloalkylthio" refers to a cycloalkylthio radical containing from three to ten carbon atoms. Cycloalkylthio groups, includes but is not limited to, cyclopropylthio, cyclobutylthio, cyclohexylthio, and the like.

The term "alkylamino", employed alone or in combination with other terms, refers to an alkyl radical that is single bonded to a nitrogen atom. The attachment point of an alkylamino radical to a molecule is through the nitrogen atom. An alkylamino radical may be depicted as —NH(alkyl). The term "$C_{1-10}$ alkylamino" refers to an alkylamino radical containing from one to ten carbon atoms, having straight or branched moieties. Alkylamino groups, includes but is not limited to, methylamino, ethylamino, propylamino, isopropylamino, butylamino, hexylamoino, and the like.

The term "cycloalkylamino", employed alone or in combination with other terms, refers to cycloalkyl radical that is single bonded to a nitrogen atom. The attachment point of a cycloalkylamino radical to a molecule is through the nitrogen atom. A cycloalkylamino radical may be depicted as —NH(cycloalkyl). "$C_{3-10}$ cycloalkylamino" refers to a cycloalkylamino radical containing from three to ten carbon atoms. Cycloalkylamino groups, includes but is not limited to, cyclopropylamino, cyclobutylamino, cyclohexylamino, and the like.

The term "di(alkyl)amino", employed alone or in combination with other terms, refers to two alkyl radicals that are single bonded to a nitrogen atom. The attachment point of an di(alkyl)amino radical to a molecule is through the nitrogen atom. A di(alkyl)amino radical may be depicted as —N(alkyl)$_2$. The term "di($C_{1-10}$ alkyl)amino" refers to a di($C_{1-10}$ alkyl)amino radical wherein the alkyl radicals each independently contains from one to ten carbon atoms, having straight or branched moieties.

The term "aryl", employed alone or in combination with other terms, encompasses: 5- and 6-membered carbocyclic aromatic rings, for example, benzene; bicyclic ring systems wherein at least one ring is carbocyclic and aromatic, for example, naphthalene, indane, and 1, 2, 3, 4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "heteroaryl", employed alone or in combination with other terms, refers to
- 5- to 8-membered aromatic, monocyclic rings containing one or more, for example, from 1 to 4, or, in some embodiments, from 1 to 3, heteroatoms selected from N, O, and S, with the remaining ring atoms being carbon;
- 8- to 12-membered bicyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring; and
- 11- to 14-membered tricyclic rings containing one or more, for example, from 1 to 4, or in some embodiments, from 1 to 3, heteroatoms selected from N, O, and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Further heteroaryl groups include but are not limited to pyrrolyl, isothiazolyl, triazinyl, pyrazinyl, pyridazinyl, indolyl, benzotriazolyl, quinoxalinyl, and isoquinolinyl,. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle", employed alone or in combination with other terms, (and variations thereof such as "heterocyclic", or "heterocyclyl") broadly refers to a single aliphatic ring, usually with 3 to 12 ring atoms, containing at least 2 carbon atoms in addition to one or more, preferably one to three heteroatoms independently selected from oxygen, sulfur, nitrogen and phosphorus, as well as combinations comprising at least one of the foregoing heteroatoms. Alternatively, a heterocycle as defined above may be a multicyclic ring system (e.g. bicyclic) in which two or more rings may be fused or bridged or spiro together, wherein at least one such ring contains one or more heteroatoms independently selected from oxygen, sulfur, nitrogen and phosphorus. "Heterocycle" also refers to 5- to 7-membered heterocyclic ring containing one or more heteroatoms selected from oxygen, sulfur, nitrogen and phosphorus fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl. 1,4-piperazinyl, and 2,3-pyridazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl. Bicyclic heterocycles include, for example:

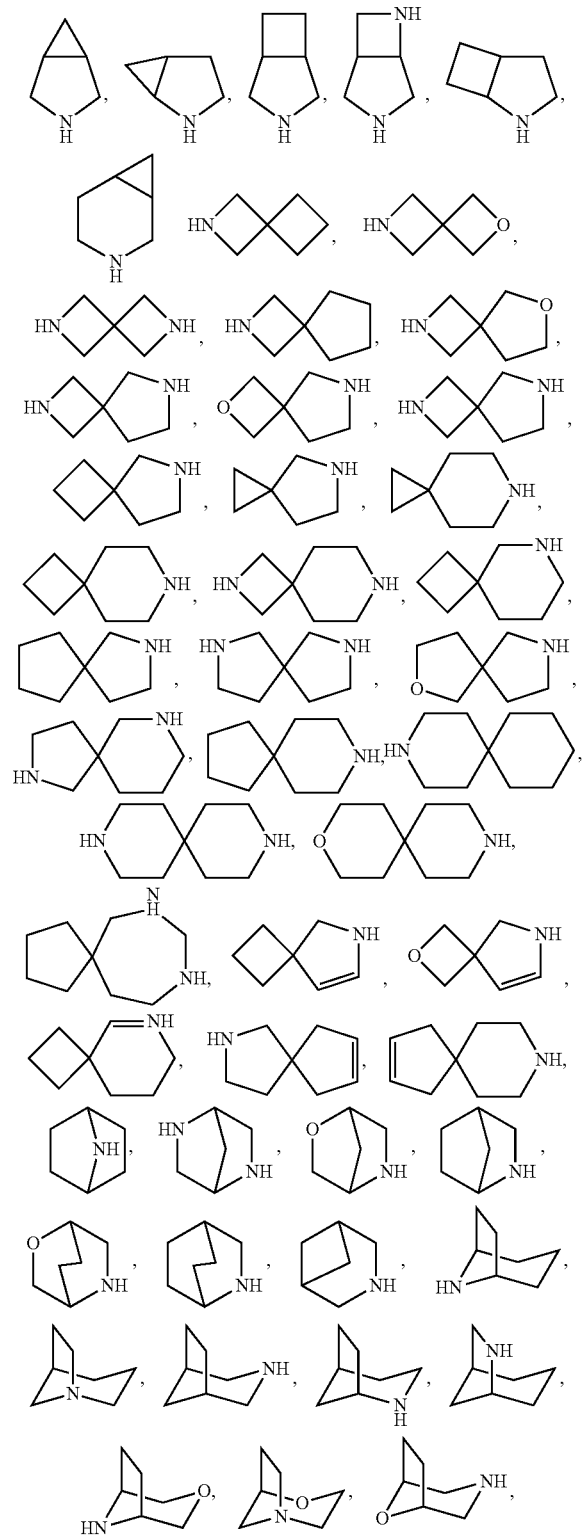

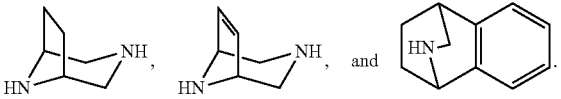

As used herein, "aryl-alkyl" refers to an alkyl moiety substituted by an aryl group. Example aryl-alkyl groups include benzyl, phenethyl, and naphthylmethyl groups. In some embodiments, aryl-alkyl groups have from 7 to 20 or 7 to 11 carbon atoms. When used in the phrase "aryl-$C_{1-4}$ alkyl", the term "$C_{1-4}$" refers to the alkyl portion of the moiety and does not describe the number of atoms in the aryl portion of the moiety.

As used herein, "heterocyclyl-alkyl" refers to alkyl substituted by heterocyclyl. When used in the phrase "heterocyclyl-$C_{1-4}$ alkyl", the term "$C_{1-4}$" refers to the alkyl portion of the moiety and does not describe the number of atoms in the heterocyclyl portion of the moiety.

As used herein, "cycloalkyl-alkyl" refers to alkyl substituted by cycloalkyl. When used in the phrase "$C_{3-10}$ cycloalkyl-$C_{1-4}$ alkyl", the term "$C_{3-10}$" refers to the cycloalkyl portion of the moiety and does not describe the number of atoms in the alkyl portion of the moiety, and the term "$C_{1-4}$" refers to the alkyl portion of the moiety and does not describe the number of atoms in the cycloalkyl portion of the moiety.

As used herein, "heteroaryl-alkyl" refers to alkyl substituted by heteroaryl. When used in the phrase "heteroaryl-$C_{1-4}$ alkyl", the term "$C_{1-4}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl, and/or heteroaryl refers to substitution of each of those groups individually as well as to substitutions of combinations of those groups. That is, if $R^1$ is aryl-$C_{1-4}$ alkyl, the aryl portion may be unsubstituted or substituted with at least one substituent, such as one, two, three, or four substituents, independently selected from $R^X$ and the alkyl portion may also be unsubstituted or substituted with at least one substituent, such as one, two, three, or four substituents, independently selected from $R^X$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The terms "administration of" and or "administering" a compound or a pharmaceutically acceptable salt should be understood to mean providing a compound or a pharmaceutically acceptable salt thereof to the individual in recognized need of treatment.

The term "effective amount" means the amount of the a compound or a pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

The term "subject" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. "Prophylaxis" refers to preventing additional symptoms and preventing the underlying metabolic causes of symptoms, and includes achieving a prophylactic benefit. For prophylactic benefit, the compositions may be administered to a patient at risk of developing a particular disease, or to a patient reporting one or more of the physiological symptoms of a disease, even though a diagnosis of this disease may not have been made.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl) ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The term "NH protecting group" as used herein includes, but not limited to, trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyloxycarbonyl, 4-(phenylazo)-benzyloxycarbonyl, 2-furfuryloxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthylmethylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclo-hexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group" as used herein includes, but not limited to, methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl) methyl, acetylmethyl, benzoylmethyl, para-nitrobenzoylmethyl, para-bromobenzoylmethyl, para-methanesulfonylb enzoylmethyl, 2-tetrahydropyranyl, 2-tetrahydrofuranyl, 2,2,2-trichloro-ethyl, 2-(trimethylsilyl) ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group" as used herein includes, but not limited to, benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethyl silylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 1998, 63, 2758-2760.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85-90%, more preferably an excess of about 95-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, nitrogen, phosphorous, sulfur, fluorine, chlorine, and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuterated acid such as $D_2SO_4/D_2O$. In addition to the above, relevant procedures and intermediates are disclosed, for instance, in Lizondo, J et al, Drugs Fut, 21(11), 1116 (1996); Brickner, S J et al., J Med Chem, 39(3), 673 (1996); Mallesham, B et al, Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of BTK inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al, J. Labelled Comp. Radiopharmaceut., 36(10):927-932 (1995); Kushner et al., Can. J. Physiol. Pharmacol, 77, 79-88 (1999).

In addition, non-radioactive isotope containing drugs, such as deuterated drugs called "heavy drugs" can be used for the treatment of diseases and conditions related to BTK activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

In an Embodiment (1), this invention provides a compound of formula (II)

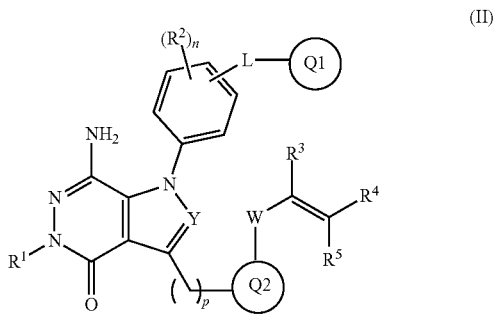

or a pharmaceutically acceptable salt thereof, wherein:

Ring Q1 is selected from aryl and heteroaryl, wherein aryl and heteroaryl are each unsubstituted or substituted with at least one substituent, such as one, two, three or four substituents, independently selected from $R^X$;

Ring Q2 is selected from $C_{3-10}$ cycloalkyl, heterocyclyl, aryl and heteroaryl, wherein cycloalkyl, heterocyclyl, aryl and heteroaryl are each unsubstituted or substituted with at least one substituent, such as one, two, three or four substituents, independently selected from $R^X$;

L is selected from a bond, —$(CR^{C1}R^{D1})_t$—, —C(O)—, —O—, —$(CR^{C1}R^{D1})_tO$—, —$O(CR^{C1}R^{D1})_t$—, —S—, —$S(O)_r$—, —$(CR^{C1}R^{D1})_tS$—, —$S(CR^{C1}R^{D1})_t$—, —$N(R^{A1})$—, —$N(R^{A1})C(O)$—, —$C(O)N(R^{A1})$—, —$N(R^{A1})C(O)O$—, —$OC(O)N(R^{A1})$—, —$N(R^{A1})C(O)N(R^{B1})$—, —$N(R^{A1})S(O)_2$—, —$S(O)_2N(R^{A1})$— and —$N(R^{A1})S(O)_2N(R^{B1})$—;

W is selected from —C(O)—, —OC(O)—, —$NR^{A1}C(O)$—, —C(=S)—, —$S(O)_r$—, —$OS(O)_r$—, and —$N(R^{A1})S(O)_r$—;

Y is selected from N and $CR^6$;

$R^1$ is selected from hydrogen, $C_{1-10}$ alkyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, wherein alkyl, cycloalkyl, heterocyclyl, aryl and heteroaryl are each unsubstituted or substituted with at least one substituent, such as one, two, three or four substituents, independently selected from $R^X$;

each $R^2$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, —$NR^{A2}R^{B2}$, —$OR^{A2}$, —$C(O)R^{A2}$, —$C(=NR^{E2})R^{A2}$, —$C(=N-OR^{B2})R^{A2}$, —$C(O)OR^{A2}$, —$OC(O)R^{A2}$, —$C(O)NR^{A2}R^{B2}$, —$NR^{A2}C(O)R^{B2}$, —$C(=NR^{E2})NR^{A2}R^{B2}$, —$NR^{A2}C(=NR^{E2})R^{B2}$, —$OC(O)NR^{A2}R^{B2}$, —$NR^{A2}C(O)OR^{B2}$, —$NR^{A2}C(O)NR^{A2}R^{B2}$, —$NR^{A2}C(S)NR^{A2}R^{B2}$, —$NR^{A2}C(=NR^{E2})NR^{A2}R^{B2}$, —$S(O)_rR^{A2}$, —$S(O)(=NR^{E2})R^{B2}$, —N=S(O)$R^{A2}R^{B2}$, —$S(O)_2OR^{A2}$, —$OS(O)_2R^{A2}$, —$NR^{A2}S(O)_rR^{B2}$, —$NR^{A2}S(O)(=NR^{E2})R^{B2}$, —$S(O)_rNR^{A2}R^{B2}$, —$S(O)(=NR^{E2})NR^{A2}R^{B2}$, —$NR^{A2}S(O)_2NR^{A2}R^{B2}$, —$NR^{A2}S(O)(=NR^{E2})NR^{A2}R^{B2}$, —$P(O)R^{A2}R^{B2}$ and —$P(O)(OR^{A2})(OR^{B2})$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

$R^3$ is selected from hydrogen, halogen, $C_{1-10}$ alkyl, $C_{3-10}$ cycloalkyl, $C_{3-10}$ cycloalkyl-$C_{1-4}$ alkyl, heterocyclyl and heterocyclyl-$C_{1-4}$ alkyl, wherein alkyl, cycloalkyl and heterocyclyl, are each unsubstituted or substituted with at least one substituent, such as one, two, three or four substituents, independently selected from $R^X$;

$R^5$ is selected from hydrogen, halogen, $C_{1-10}$ alkyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, cycloalkyl, heterocyclyl, aryl and heteroaryl are each unsubstituted or substituted with at least one substituent, such as one, two, three or four substituents, independently selected from $R^X$;

$R^4$ is selected from hydrogen, halogen, $C_{1-10}$ alkyl, $C_{3-10}$ cycloalkyl, $C_{3-10}$ cycloalkyl-$C_{1-4}$ alkyl, heterocyclyl and heterocyclyl-$C_{1-4}$ alkyl, wherein alkyl, cycloalkyl and heterocyclyl, are each unsubstituted or substituted with at least one substituent, such as one, two, three or four substituents, independently selected from $R^X$;

or $R^3$ and $R^4$ taken together form a bond;

$R^6$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, —$NR^{A3}R^{B3}$, —$OR^{A3}$, —$C(O)R^{A3}$, —$C(=NR^{E3})R^{A3}$, —$C(=N-OR^{B3})R^{A3}$, —$C(O)OR^{A3}$, —$OC(O)R^{A3}$, —$C(O)NR^{A3}R^{B3}$, —$NR^{A3}C(O)R^{B3}$, —$C(=NR^{E3})NR^{A3}R^{B3}$, —$NR^{A3}C(=NR^{E3})R^{B3}$, —$OC(O)NR^{A3}R^{B3}$, —$NR^{A3}C(O)OR^{B3}$, —$NR^{A3}C(O)NR^{A3}R^{B3}$, —$NR^{A3}C(S)NR^{A3}R^{B3}$, —$NR^{A3}C(=NR^{E3})NR^{A3}R^{B3}$, —$S(O)_rR^{A3}$, —$S(O)(=NR^{E3})R^{B3}$, —N=S(O)$R^{A3}R^{B3}$, —$S(O)_2OR^{A3}$, —$OS(O)_2R^{A3}$, —$NR^{A3}S(O)_rR^{B3}$, —$NR^{A3}S(O)(=NR^{E3})R^{B3}$, —$S(O)_rNR^{A3}R^{B3}$, —$S(O)(=NR^{E3})NR^{A3}R^{B3}$, —$NR^{A3}S(O)_2NR^{A3}R^{B3}$, —$NR^{A3}S(O)(=NR^{E3})NR^{A3}R^{B3}$, —$P(O)R^{A3}R^{B3}$ and —$P(O)(OR^{A3})(OR^{B3})$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

each $R^{A1}$, $R^{A2}$, $R^{A3}$, $R^{B1}$, $R^{B2}$ and $R^{B3}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl- $C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

or each "$R^{A1}$ and $R^{B1}$", "$R^{A2}$ and $R^{B2}$" or "$R^{A3}$ and $R^{B3}$" together with the atom(s) to which they are attached form a heterocyclic ring of 4 to 12 members containing 0, 1, or 2 additional heteroatoms independently selected from oxygen, sulfur and nitrogen, and optionally substituted with 1 2 or 3 $R^X$ groups;

each $R^{C1}$ and $R^{D1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

or $R^{C1}$ and $R^{D1}$ together with the carbon atom(s) to which they are attached form a ring of 3 to 12 members containing 0, 1 or 2 heteroatoms independently selected from oxygen, sulfur and nitrogen, and optionally substituted with 1 2 or 3 $R^X$ groups;

each $R^{E2}$ and $R^{E3}$ are independently selected from hydrogen, $C_{1-10}$ alkyl, CN, $NO_2$, —$OR^{a1}$, —$SR^{a1}$, —$S(O)_r R^{a1}$, —$C(O)R^{a1}$, —$C(O)OR^{a1}$, —$C(O)NR^{a1}R^{b1}$ and —$S(O)_r NR^{a1}R^{b1}$;

each $R^X$ is independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, $NO_2$, —$(CR^{c1}R^{d1})_t NR^{a1}R^{b1}$, —$(CR^{c1}R^{d1})_t OR^{b1}$, —$(CR^{c1}R^{d1})_t C(O)R^{a1}$, —$(CR^{c1}R^{d1})_t C(=NR^{e1})R^{a1}$, —$(CR^{c1}R^{d1})_t C(=N—OR^{b1})R^{a1}$, —$(CR^{c1}R^{d1})_t C(O)OR^{b1}$, —$(CR^{c1}R^{d1})_t OC(O)R^{b1}$, —$(CR^{c1}R^{d1})_t C(O)NR^{a1}R^{b1}$, —$(CR^{c1}R^{d1})_t NR^{a1}C(O)R^{b1}$, —$(CR^{c1}R^{d1})_t C(=NR^{e1})NR^{a1}R^{b1}$, —$(CR^{c1}R^{d1})_t NR^{a1}C(=NR^{e1})R^{b1}$, —$(CR^{c1}R^{d1})_t OC(O)NR^{a1}R^{b1}$, —$(CR^{c1}R^{d1})_t NR^{a1}C(O)OR^{b1}$, —$(CR^{c1}R^{d1})_t NR^{a1}C(O)NR^{a1}R^{b1}$, —$(CR^{c1}R^{d1})_t NR^{a1}C(S)NR^{a1}R^{b1}$, —$(CR^{c1}R^{d1})_t NR^{a1}C(=NR^{e1})NR^{a1}R^{b1}$, —$(CR^{c1}R^{d1})_t S(O)_r R^{b1}$, —$(CR^{c1}R^{d1})_t S(O)(=NR^{e1})R^{b1}$, —$(CR^{c1}R^{d1})_t N=S(O)R^{a1}R^{b1}$, —$(CR^{c1}R^{d1})_t S(O)_2 OR^{b1}$, —$(CR^{c1}R^{d1})_t OS(O)_2 R^{b1}$, —$(CR^{c1}R^{d1})_t NR^{a1}S(O)_r R^{b1}$, —$(CR^{c1}R^{d1})_t NR^{a1}S(O)(=NR^{e1})R^{b1}$, —$(CR^{c1}R^{d1})_t S(O)_r NR^{a1}R^{b1}$, —$(CR^{c1}R^{d1})_t S(O)(=NR^{e1})NR^{a1}R^{b1}$, —$(CR^{c1}R^{d1})_t NR^{a1} S(O)_2 NR^{a1}R^{b1}$, —$(CR^{c1}R^{d1})_t NR^{a1}S(O)(=NR^{e1})NR^{a1}R^{b1}$, —$(CR^{c1}R^{d1})_t P(O)R^{a1}R^{b1}$ and —$(CR^{c1}R^{d1})_t P(O)(OR^{a1})(OR^{b1})$, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

or $R^{a1}$ and $R^{b1}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1, 2 or 3 $R^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

or $R^{c1}$ and $R^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, CN, $NO_2$, —$OR^{a2}$, —$SR^{a2}$, —$S(O)_r R^{a2}$, —$C(O)R^{a2}$, —$C(O)OR^{a2}$, —$S(O)_r NR^{a2}R^{b2}$ and —$C(O)NR^{a2}R^{b2}$;

each $R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, $NO_2$, —$(CR^{c2}R^{d2})_t NR^{a2}R^{b2}$, —$(CR^{c2}R^{d2})_t OR^{b2}$, —$(CR^{c2}R^{d2})_t C(O)R^{a2}$, —$(CR^{c2}R^{d2})_t C(=NR^{e2})R^{a2}$, —$(CR^{c2}R^{d2})_t C(=N—OR^{b2})R^{a2}$, —$(CR^{c2}R^{d2})_t C(O)OR^{b2}$, —$(CR^{c2}R^{d2})_t OC(O)R^{b2}$, —$(CR^{c2}R^{d2})_t C(O)NR^{a2}R^{b2}$, —$(CR^{c2}R^{d2})_t NR^{a2}C(O)R^{b2}$, —$(CR^{c2}R^{d2})_t C(=NR^{e2})NR^{a2}R^{b2}$, —$(CR^{c2}R^{d2})_t NR^{a2}C(=NR^{e2})R^{b2}$, —$(CR^{c2}R^{d2})_t OC(O)NR^{a2}R^{b2}$, —$(CR^{c2}R^{d2})_t NR^{a2}C(O)OR^{b2}$, —$(CR^{c2}R^{d2})_t NR^{a2}C(O)NR^{a2}R^{b2}$, —$(CR^{c2}R^{d2})_t NR^{a2}C(S)NR^{a2}R^{b2}$, —$(CR^{c2}R^{d2})_t NR^{a2}C(=NR^{e2})NR^{a2}R^{b2}$, —$(CR^{c2}R^{d2})_t S(O)_r R^{b2}$, —$(CR^{c2}R^{d2})_t S(O)(=NR^{e2})R^{b2}$, —$(CR^{c2}R^{d2})_t N=S(O)R^{a2}R^{b2}$, —$(CR^{c2}R^{d2})_t S(O)_2 OR^{b2}$, —$(CR^{c2}R^{d2})_t OS(O)_2 R^{b2}$, —$(CR^{c2}R^{d2})_t NR^{a2}S(O)_r R^{b2}$, —$(CR^{c2}R^{d2})_t NR^{a2}S(O)(=NR^{e2})R^{b2}$, —$(CR^{c2}R^{d2})_t S(O)_r NR^{a2}R^{b2}$, —$(CR^{c2}R^{d2})_t S(O)(=NR^{e2})NR^{a2}R^{b2}$, —$(CR^{c2}R^{d2})_t NR^{a2} S(O)_2 NR^{a2}R^{b2}$, —$(CR^{c2}R^{d2})_t NR^{a2}S(O)(=NR^{e2})NR^{a2}R^{b2}$, —$(CR^{c2}R^{d2})_t P(O)R^{a2}R^{b2}$ and —$(CR^{c2}R^{d2})_t P(O)(OR^{a2})(OR^{b2})$, wherein alkyl, alkenyl, alkynyl, cycloalkyl, heterocyclyl, aryl and heteroaryl are each unsubstituted or substituted with at least one substituent, such as one, two, three or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl) amino;

or $R^{a2}$ and $R^{b2}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl) amino;

or $R^{c2}$ and $R^{d2}$ together with the carbon atom(s) to which they are attached form a ring of 3 to 12 members containing 0, 1 or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)O$C_{1-4}$ alkyl, —C(O)O$C_{3-10}$ cycloalkyl, —C(O)N($C_{1-4}$ alkyl)$_2$, —C(O)N($C_{3-10}$ cycloalkyl)$_2$, —S(O)$_2C_{1-4}$ alkyl, —S(O)$_2C_{3-10}$ cycloalkyl, —S(O)$_2$N($C_{1-4}$ alkyl)$_2$ and —S(O)$_2$N($C_{3-10}$ cycloalkyl)$_2$;

n is selected from 0, 1, 2, 3 and 4;
p is selected from 0, 1 and 2;
each r is independently selected from 1 and 2;
each t is independently selected from 1, 2, 3 and 4.

In another Embodiment (2), the invention provides a compound of Embodiment (1) or a pharmaceutically acceptable salt thereof, wherein Y is N.

In another Embodiment (3), the invention provides a compound of Embodiment (1) or a pharmaceutically acceptable salt thereof, wherein Y is $CR^6$.

In another Embodiment (4), the invention provides a compound of Embodiment (3) or a pharmaceutically acceptable salt thereof, wherein Y is CH.

In another Embodiment (5), the invention provides a compound of any one of Embodiments (1)-(4) or a pharmaceutically acceptable salt thereof, wherein L is selected from —O—, —S—, and —C(O)N($R^{A1}$)—.

In another Embodiment (6), the invention provides a compound of Embodiment (5) or a pharmaceutically acceptable salt thereof, wherein L is selected from —O— and —C(O)NH—.

In another Embodiment (7), the invention provides a compound of Embodiment (6) or a pharmaceutically acceptable salt thereof, wherein L is —O—.

In another Embodiment (8), the invention provides a compound of any one of Embodiments (1)-(7) or a pharmaceutically acceptable salt thereof, wherein Ring Q1 is selected from aryl and heteroaryl, wherein aryl and heteroaryl are independently unsubstituted or substituted with at least one substituent independently selected from $R^X$.

In another Embodiment (9), the invention provides a compound of Embodiment (8) or a pharmaceutically acceptable salt thereof, wherein Ring Q1 is selected from phenyl and pyridinyl, wherein phenyl and pyridinyl are independently unsubstituted or substituted with at least one substituent independently selected from $R^X$.

In another Embodiment (10), the invention provides a compound of Embodiment (9) or a pharmaceutically acceptable salt thereof, wherein Ring Q1 is selected from phenyl and pyridinyl, wherein phenyl and pyridinyl are independently unsubstituted or substituted with at least one substituent independently selected from halogen.

In another Embodiment (11), the invention provides a compound of any one of Embodiments (1)-(10) or a pharmaceutically acceptable salt thereof, wherein the substructure of

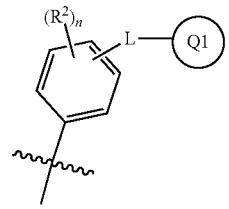

in Formula (II) is

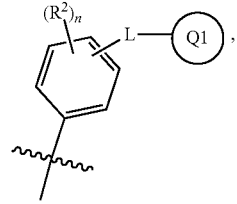

wherein the ～ symbol indicates the point of attachment to the rest of the molecule.

In another Embodiment (12), the invention provides a compound of any one of Embodiments (1)-(11) or a pharmaceutically acceptable salt thereof, wherein $R^1$ is hydrogen.

In another Embodiment (13), the invention provides a compound of any one of Embodiments (1)-(12) or a pharmaceutically acceptable salt thereof, wherein $R^2$ is hydrogen.

In another Embodiment (14), the invention provides a compound of any one of Embodiments (1)-(13) or a pharmaceutically acceptable salt thereof, wherein p is 0.

In another Embodiment (15), the invention provides a compound of any one of Embodiments (1)-(14) or a pharmaceutically acceptable salt thereof, wherein Ring Q2 is heterocyclyl, wherein heterocyclyl is unsubstituted or substituted with at least one substituent independently selected from $R^X$.

In another Embodiment (16), the invention provides a compound of Embodiment (15) or a pharmaceutically acceptable salt thereof, wherein Ring Q2 is selected from azetidinyl, pyrrolidinyl and piperidinyl, wherein azetidinyl, pyrrolidinyl and piperidinyl are each independently unsubstituted or substituted with at least one substituent independently selected from $R^X$.

In another Embodiment (17), the invention provides a compound of any one of Embodiments (1)-(16) or a pharmaceutically acceptable salt thereof, wherein W is —C(O)—.

In another Embodiment (18), the invention provides a compound of any one of Embodiments (15)-(16) or a pharmaceutically acceptable salt thereof, wherein W is —C(O)— and the attachment of W to Q2 is through N.

In another Embodiment (19), the invention provides a compound of any one of Embodiments (1)-(18) or a pharmaceutically acceptable salt thereof, wherein $R^3$ and $R^4$ are hydrogen.

In another Embodiment (20), the invention provides a compound of Embodiment (19) or a pharmaceutically acceptable salt thereof, wherein $R^4$ is selected from hydrogen, $C_{1-10}$ alkyl, and heterocyclyl, wherein alkyl and heterocyclyl are each unsubstituted or substituted with at least one substituent independently selected from $R^X$.

In another Embodiment (21), the invention provides a compound of Embodiment (20) or a pharmaceutically acceptable salt thereof, wherein $R^4$ is selected from hydrogen, methoxymethyl, dimethylaminomethyl and azetidinyl, wherein azetidinyl is unsubstituted or substituted with at least one substituent independently selected from $R^X$.

In another Embodiment (22), the invention provides a compound of Embodiment (21) or a pharmaceutically acceptable salt thereof, wherein $R^X$ is selected from methyl and ethyl.

In another Embodiment (23), the invention provides a compound of any one of Embodiments (1)-(18) or a pharmaceutically acceptable salt thereof, wherein $R^3$ and $R^4$ taken together form a bond, and $R^5$ is $C_{1-10}$ alkyl.

In another Embodiment (23), the invention provides a compound of Embodiment (23) or a pharmaceutically acceptable salt thereof, wherein $R^4$ is methyl.

In another Embodiment (24), the invention provides a compound selected from
3-(1-acryloylpyrrolidin-3-yl)-7-amino-1-(4-phenoxyphenyl)-1,5-dihydro-4H-pyrrolo[2,3-d]pyridazin-4-one,
7-amino-3-(1-(but-2-ynoyl)pyrrolidin-3-yl)-1-(4-phenoxyphenyl)-1,5-dihydro-4H-pyrrolo[2,3-d]pyridazin-4-one,
3-(1-acryloylpyrrolidin-3-yl)-7-amino-1-(4-(2,6-difluorophenoxy)phenyl)-1,5-dihydro-4H-pyrrolo[2,3-d]pyridazin-4-one,
7-amino-3-(1-(but-2-ynoyl)pyrrolidin-3-yl)-1-(4-(2,6-difluorophenoxy)phenyl)-1,5-dihydro-4H-pyrrolo[2,3-d]pyridazin-4-one,
3-(1-acryloylpyrrolidin-3-yl)-7-amino-1-(4-phenoxyphenyl)-1,5-dihydro-4H-pyrazolo[3,4-d]pyridazin-4-one,
7-amino-3-(1-(but-2-ynoyl)pyrrolidin-3-yl)-1-(4-phenoxyphenyl)-1,5-dihydro-4H-pyrazolo[3,4-d]pyridazin-4-one,
3-(1-acryloylpyrrolidin-3-yl)-7-amino-1-(4-(2,6-difluorophenoxy)phenyl)-1,5-dihydro-4H-pyrazolo[3,4-d]pyridazin-4-one,
7-amino-3-(1-(but-2-ynoyl)pyrrolidin-3-yl)-1-(4-(2,6-difluorophenoxy)phenyl)-1,5-dihydro-4H-pyrazolo[3,4-d]pyridazin-4-one,
(S)-3-(1-acryloylpyrrolidin-3-yl)-7-amino-1-(4-phenoxyphenyl)-1,5-dihydro-4H-pyrrolo[2,3-d]pyridazin-4-one,
(R)-3-(1-acryloylpyrrolidin-3-yl)-7-amino-1-(4-phenoxyphenyl)-1,5-dihydro-4H-pyrrolo[2,3-d]pyridazin-4-one,
(S)-3-(1-acryloylpiperidin-3-yl)-7-amino-1-(4-phenoxyphenyl)-1,5-dihydro-4H-pyrrolo[2,3-d]pyridazin-4-one,
(R)-3-(1-acryloylpiperidin-3-yl)-7-amino-1-(4-phenoxyphenyl)-1,5-dihydro-4H-pyrrolo[2,3-d]pyridazin-4-one,
(R)-3-(1-acryloylpyrrolidin-3-yl)-7-amino-1-(4-phenoxyphenyl)-1,5-dihydro-4H-pyrazolo[3,4-d]pyridazin-4-one,
(S)-3-(1-acryloylpyrrolidin-3-yl)-7-amino-1-(4-phenoxyphenyl)-1,5-dihydro-4H-pyrazolo[3,4-d]pyridazin-4-one,
(R)-3-(1-acryloylpiperidin-3-yl)-7-amino-1-(4-phenoxyphenyl)-1,5-dihydro-4H-pyrazolo[3,4-d]pyridazin-4-one,
(S)-3-(1-acryloylpiperidin-3-yl)-7-amino-1-(4-phenoxyphenyl)-1,5-dihydro-4H-pyrazolo[3,4-d]pyridazin-4-one,
(S)-3-(1-acryloylpyrrolidin-3-yl)-7-amino-1-(4-(2-fluorophenoxy)phenyl)-1,5-dihydro-4H-pyrrolo[2,3-d]pyridazin-4-one,
(S)-3-(1-acryloylpyrrolidin-3-yl)-7-amino-1-(4-(3-fluorophenoxy)phenyl)-1,5-dihydro-4H-pyrrolo[2,3-d]pyridazin-4-one,
(S)-3-(1-acryloylpyrrolidin-3-yl)-7-amino-1-(4-(4-fluorophenoxy)phenyl)-1,5-dihydro-4H-pyrrolo[2,3-d]pyridazin-4-one,
(S)-3-(1-acryloylpyrrolidin-3-yl)-7-amino-1-(4-(2,3-difluorophenoxy)phenyl)-1,5-dihydro-4H-pyrrolo[2,3-d]pyridazin-4-one,
(S)-3-(1-acryloylpyrrolidin-3-yl)-7-amino-1-(4-(2,6-difluorophenoxy)phenyl)-1,5-dihydro-4H-pyrrolo[2,3-d]pyridazin-4-one,
(S)-3-(1-acryloylpyrrolidin-3-yl)-7-amino-1-(4-(3,5-difluorophenoxy)phenyl)-1,5-dihydro-4H-pyrrolo[2,3-d]pyridazin-4-one,
(R)-3-(1-acryloylpyrrolidin-3-yl)-7-amino-1-(4-(2-fluorophenoxy)phenyl)-1,5-dihydro-4H-pyrrolo[2,3-d]pyridazin-4-one,
(R)-3-(1-acryloylpyrrolidin-3-yl)-7-amino-1-(4-(3-fluorophenoxy)phenyl)-1,5-dihydro-4H-pyrrolo[2,3-d]pyridazin-4-one,
(R)-3-(1-acryloylpyrrolidin-3-yl)-7-amino-1-(4-(4-fluorophenoxy)phenyl)-1,5-dihydro-4H-pyrrolo[2,3-d]pyridazin-4-one,
(R)-3-(1-acryloylpyrrolidin-3-yl)-7-amino-1-(4-(2,3-difluorophenoxy)phenyl)-1,5-dihydro-4H-pyrrolo[2,3-d]pyridazin-4-one,
(R)-3-(1-acryloylpyrrolidin-3-yl)-7-amino-1-(4-(2,6-difluorophenoxy)phenyl)-1,5-dihydro-4H-pyrrolo[2,3-d]pyridazin-4-one,
(R)-3-(1-acryloylpyrrolidin-3-yl)-7-amino-1-(4-(3,5-difluorophenoxy)phenyl)-1,5-dihydro-4H-pyrrolo[2,3-d]pyridazin-4-one,
(S)-3-(1-acryloylpiperidin-3-yl)-7-amino-1-(4-(2-fluorophenoxy)phenyl)-1,5-dihydro-4H-pyrrolo[2,3-d]pyridazin-4-one,
(S)-3-(1-acryloylpiperidin-3-yl)-7-amino-1-(4-(3-fluorophenoxy)phenyl)-1,5-dihydro-4H-pyrrolo[2,3-d]pyridazin-4-one,
(S)-3-(1-acryloylpiperidin-3-yl)-7-amino-1-(4-(4-fluorophenoxy)phenyl)-1,5-dihydro-4H-pyrrolo[2,3-d]pyridazin-4-one,
(S)-3-(1-acryloylpiperidin-3-yl)-7-amino-1-(4-(2,3-difluorophenoxy)phenyl)-1,5-dihydro-4H-pyrrolo[2,3-d]pyridazin-4-one, (S)-3-(1-acryloylpiperidin-3-yl)-7-amino-1-(4-(2,6-difluorophenoxy)phenyl)-1,5-dihydro-4H-pyrrolo[2,3-d]pyridazin-4-one,
(S)-3-(1-acryloylpiperidin-3-yl)-7-amino-1-(4-(3,5-difluorophenoxy)phenyl)-1,5-dihydro-4H-pyrrolo[2,3-d]pyridazin-4-one,
(R)-3-(1-acryloylpiperidin-3-yl)-7-amino-1-(4-(2-fluorophenoxy)phenyl)-1,5-dihydro-4H-pyrrolo[2,3-d]pyridazin-4-one,
(R)-3-(1-acryloylpiperidin-3-yl)-7-amino-1-(4-(3-fluorophenoxy)phenyl)-1,5-dihydro-4H-pyrrolo[2,3-d]pyridazin-4-one,
(R)-3-(1-acryloylpiperidin-3-yl)-7-amino-1-(4-(4-fluorophenoxy)phenyl)-1,5-dihydro-4H-pyrrolo[2,3-d]pyridazin-4-one,
(R)-3-(1-acryloylpiperidin-3-yl)-7-amino-1-(4-(2,3-difluorophenoxy)phenyl)-1,5-dihydro-4H-pyrrolo[2,3-d]pyridazin-4-one,
(R)-3-(1-acryloylpiperidin-3-yl)-7-amino-1-(4-(2,6-difluorophenoxy)phenyl)-1,5-dihydro-4H-pyrrolo[2,3-d]pyridazin-4-one,
(R)-3-(1-acryloylpiperidin-3-yl)-7-amino-1-(4-(3,5-difluorophenoxy)phenyl)-1,5-dihydro-4H-pyrrolo[2,3-d]pyridazin-4-one,
(R)-3-(1-acryloylpyrrolidin-3-yl)-7-amino-1-(4-(2-fluorophenoxy)phenyl)-1,5-dihydro-4H-pyrazolo[3,4-d]pyridazin-4-one,
(R)-3-(1-acryloylpyrrolidin-3-yl)-7-amino-1-(4-(3-fluorophenoxy)phenyl)-1,5-dihydro-4H-pyrazolo[3,4-d]pyridazin-4-one,
(R)-3-(1-acryloylpyrrolidin-3-yl)-7-amino-1-(4-(4-fluorophenoxy)phenyl)-1,5-dihydro-4H-pyrazolo[3,4-d]pyridazin-4-one,
(R)-3-(1-acryloylpyrrolidin-3-yl)-7-amino-1-(4-(2,3-difluorophenoxy)phenyl)-1,5-dihydro-4H-pyrazolo[3,4-d]pyridazin-4-one,
(R)-3-(1-acryloylpyrrolidin-3-yl)-7-amino-1-(4-(2,6-difluorophenoxy)phenyl)-1,5-dihydro-4H-pyrazolo[3,4-d]pyridazin-4-one,
(R)-3-(1-acryloylpyrrolidin-3-yl)-7-amino-1-(4-(3,5-difluorophenoxy)phenyl)-1,5-dihydro-4H-pyrazolo[3,4-d]pyridazin-4-one,
(S)-3-(1-acryloylpyrrolidin-3-yl)-7-amino-1-(4-(2-fluorophenoxy)phenyl)-1,5-dihydro-4H-pyrazolo[3,4-d]pyridazin-4-one,
(S)-3-(1-acryloylpyrrolidin-3-yl)-7-amino-1-(4-(3-fluorophenoxy)phenyl)-1,5-dihydro-4H-pyrazolo[3,4-d]pyridazin-4-one,
(S)-3-(1-acryloylpyrrolidin-3-yl)-7-amino-1-(4-(4-fluorophenoxy)phenyl)-1,5-dihydro-4H-pyrazolo[3,4-d]pyridazin-4-one,
(S)-3-(1-acryloylpyrrolidin-3-yl)-7-amino-1-(4-(2,3-difluorophenoxy)phenyl)-1,5-dihydro-4H-pyrazolo[3,4-d]pyridazin-4-one,
(S)-3-(1-acryloylpyrrolidin-3-yl)-7-amino-1-(4-(2,6-difluorophenoxy)phenyl)-1,5-dihydro-4H-pyrazolo[3,4-d]pyridazin-4-one,
(S)-3-(1-acryloylpyrrolidin-3-yl)-7-amino-1-(4-(3,5-difluorophenoxy)phenyl)-1,5-dihydro-4H-pyrazolo[3,4-d]pyridazin-4-one,
(R)-3-(1-acryloylpiperidin-3-yl)-7-amino-1-(4-(2-fluorophenoxy)phenyl)-1,5-dihydro-4H-pyrazolo[3,4-d]pyridazin-4-one,
(R)-3-(1-acryloylpiperidin-3-yl)-7-amino-1-(4-(3-fluorophenoxy)phenyl)-1,5-dihydro-4H-pyrazolo[3,4-d]pyridazin-4-one,
(R)-3-(1-acryloylpiperidin-3-yl)-7-amino-1-(4-(4-fluorophenoxy)phenyl)-1,5-dihydro-4H-pyrazolo[3,4-d]pyridazin-4-one,
(R)-3-(1-acryloylpiperidin-3-yl)-7-amino-1-(4-(2,3-difluorophenoxy)phenyl)-1,5-dihydro-4H-pyrazolo[3,4-d]pyridazin-4-one,
(R)-3-(1-acryloylpiperidin-3-yl)-7-amino-1-(4-(2,6-difluorophenoxy)phenyl)-1,5-dihydro-4H-pyrazolo[3,4-d]pyridazin-4-one,
(R)-3-(1-acryloylpiperidin-3-yl)-7-amino-1-(4-(3,5-difluorophenoxy)phenyl)-1,5-dihydro-4H-pyrazolo[3,4-d]pyridazin-4-one,
(S)-3-(1-acryloylpiperidin-3-yl)-7-amino-1-(4-(2-fluorophenoxy)phenyl)-1,5-dihydro-4H-pyrazolo[3,4-d]pyridazin-4-one,
(S)-3-(1-acryloylpiperidin-3-yl)-7-amino-1-(4-(3-fluorophenoxy)phenyl)-1,5-dihydro-4H-pyrazolo[3,4-d]pyridazin-4-one,
(S)-3-(1-acryloylpiperidin-3-yl)-7-amino-1-(4-(4-fluorophenoxy)phenyl)-1,5-dihydro-4H-pyrazolo[3,4-d]pyridazin-4-one,
(S)-3-(1-acryloylpiperidin-3-yl)-7-amino-1-(4-(2,3-difluorophenoxy)phenyl)-1,5-dihydro-4H-pyrazolo[3,4-d]pyridazin-4-one,
(S)-3-(1-acryloylpiperidin-3-yl)-7-amino-1-(4-(2,6-difluorophenoxy)phenyl)-1,5-dihydro-4H-pyrazolo[3,4-d]pyridazin-4-one,
(S)-3-(1-acryloylpiperidin-3-yl)-7-amino-1-(4-(3,5-difluorophenoxy)phenyl)-1,5-dihydro-4H-pyrazolo[3,4-d]pyridazin-4-one,
(R)-7-amino-3-(1-(but-2-ynoyl)pyrrolidin-3-yl)-1-(4-phenoxyphenyl)-1,5-dihydro-4H-pyrazolo[3,4-d]pyridazin-4-one,
(S)-7-amino-3-(1-(but-2-ynoyl)pyrrolidin-3-yl)-1-(4-phenoxyphenyl)-1,5-dihydro-4H-pyrazolo[3,4-d]pyridazin-4-one,
(S)-7-amino-3-(1-(but-2-ynoyl)pyrrolidin-3-yl)-1-(4-phenoxyphenyl)-1,5-dihydro-4H-pyrrolo[2,3-d]pyridazin-4-one,
(R)-7-amino-3-(1-(but-2-ynoyl)pyrrolidin-3-yl)-1-(4-phenoxyphenyl)-1,5-dihydro-4H-pyrrolo[2,3-d]pyridazin-4-one,
(R)-7-amino-3-(1-(but-2-ynoyl)piperidin-3-yl)-1-(4-phenoxyphenyl)-1,5-dihydro-4H-pyrazolo[3,4-d]pyridazin-4-one,
(S)-7-amino-3-(1-(but-2-ynoyl)piperidin-3-yl)-1-(4-phenoxyphenyl)-1,5-dihydro-4H-pyrazolo[3,4-d]pyridazin-4-one,
(S)-7-amino-3-(1-(but-2-ynoyl)piperidin-3-yl)-1-(4-phenoxyphenyl)-1,5-dihydro-4H-pyrrolo[2,3-d]pyridazin-4-one,
(R)-7-amino-3-(1-(but-2-ynoyl)piperidin-3-yl)-1-(4-phenoxyphenyl)-1,5-dihydro-4H-pyrrolo[2,3-d]pyridazin-4-one,
(R)-7-amino-3-(1-(but-2-ynoyl)pyrrolidin-3-yl)-1-(4-(2-fluorophenoxy)phenyl)-1,5-dihydro-4H-pyrazolo[3,4-d]pyridazin-4-one,
(S)-7-amino-3-(1-(but-2-ynoyl)pyrrolidin-3-yl)-1-(4-(2-fluorophenoxy)phenyl)-1,5-dihydro-4H-pyrazolo[3,4-d]pyridazin-4-one,
(S)-7-amino-3-(1-(but-2-ynoyl)pyrrolidin-3-yl)-1-(4-(2-fluorophenoxy)phenyl)-1,5-dihydro-4H-pyrrolo[2,3-d]pyridazin-4-one,
(R)-7-amino-3-(1-(but-2-ynoyl)pyrrolidin-3-yl)-1-(4-(2-fluorophenoxy)phenyl)-1,5-dihydro-4H-pyrrolo[2,3-d]pyridazin-4-one, (R)-7-amino-3-(1-(but-2-ynoyl)piperidin-3-yl)-1-(4-(2-fluorophenoxy)phenyl)-1,5-dihydro-4H-pyrazolo[3,4-d]pyridazin-4-one,
(S)-7-amino-3-(1-(but-2-ynoyl)piperidin-3-yl)-1-(4-(2-fluorophenoxy)phenyl)-1,5-dihydro-4H-pyrazolo[3,4-d]pyridazin-4-one,
(S)-7-amino-3-(1-(but-2-ynoyl)piperidin-3-yl)-1-(4-(2-fluorophenoxy)phenyl)-1,5-dihydro-4H-pyrrolo[2,3-d]pyridazin-4-one,
(R)-7-amino-3-(1-(but-2-ynoyl)piperidin-3-yl)-1-(4-(2-fluorophenoxy)phenyl)-1,5-dihydro-4H-pyrrolo[2,3-d]pyridazin-4-one,
(R)-7-amino-3-(1-(but-2-ynoyl)pyrrolidin-3-yl)-1-(4-(2,6-difluorophenoxy)phenyl)-1,5-dihydro-4H-pyrazolo[3,4-d]pyridazin-4-one,
(S)-7-amino-3-(1-(but-2-ynoyl)pyrrolidin-3-yl)-1-(4-(2,6-difluorophenoxy)phenyl)-1,5-dihydro-4H-pyrazolo[3,4-d]pyridazin-4-one,
(S)-7-amino-3-(1-(but-2-ynoyl)pyrrolidin-3-yl)-1-(4-(2,6-difluorophenoxy)phenyl)-1,5-dihydro-4H-pyrrolo[2,3-d]pyridazin-4-one,
(R)-7-amino-3-(1-(but-2-ynoyl)pyrrolidin-3-yl)-1-(4-(2,6-difluorophenoxy)phenyl)-1,5-dihydro-4H-pyrrolo[2,3-d]pyridazin-4-one,
(R)-7-amino-3-(1-(but-2-ynoyl)piperidin-3-yl)-1-(4-(2,6-difluorophenoxy)phenyl)-1,5-dihydro-4H-pyrazolo[3,4-d]pyridazin-4-one,
(S)-7-amino-3-(1-(but-2-ynoyl)piperidin-3-yl)-1-(4-(2,6-difluorophenoxy)phenyl)-1,5-dihydro-4H-pyrazolo[3,4-d]pyridazin-4-one,
(S)-7-amino-3-(1-(but-2-ynoyl)piperidin-3-yl)-1-(4-(2,6-difluorophenoxy)phenyl)-1,5-dihydro-4H-pyrrolo[2,3-d]pyridazin-4-one,
(R)-7-amino-3-(1-(but-2-ynoyl)piperidin-3-yl)-1-(4-(2,6-difluorophenoxy)phenyl)-1,5-dihydro-4H-pyrrolo[2,3-d]pyridazin-4-one,
(R)-4-(7-amino-3-(1-(but-2-ynoyl)pyrrolidin-3-yl)-4-oxo-4,5-dihydro-1H-pyrazolo[3,4-d]pyridazin-1-yl)-N-(pyridin-2-yl)benzamide,
(R)-4-(3-(1-acryloylpyrrolidin-3-yl)-7-amino-4-oxo-4,5-dihydro-1H-pyrazolo[3,4-d]pyridazin-1-yl)-N-(pyridin-2-yl)benzamide,
(S,E)-7-amino-3-(1-(4-methoxybut-2-enoyl)pyrrolidin-3-yl)-1-(4-phenoxyphenyl)-1,5-dihydro-4H-pyrrolo[2,3-d]pyridazin-4-one,
(S,E)-7-amino-1-(4-(2-fluorophenoxy)phenyl)-3-(1-(4-methoxybut-2-enoyl)pyrrolidin-3-yl)-1,5-dihydro-4H-pyrrolo[2,3-d]pyridazin-4-one,
(S,E)-7-amino-3-(1-(4-(dimethylamino)but-2-enoyl)pyrrolidin-3-yl)-1-(4-phenoxyphenyl)-1,5-dihydro-4H-pyrrolo[2,3-d]pyridazin-4-one,
(S,E)-7-amino-3-(1-(4-(dimethylamino)but-2-enoyl)pyrrolidin-3-yl)-1-(4-(2-fluorophenoxy)phenyl)-1,5-dihydro-4H-pyrrolo[2,3-d]pyridazin-4-one,
7-amino-3-((S)-1-((E)-3-((R)-azetidin-2-yl)acryloyl)pyrrolidin-3-yl)-1-(4-phenoxyphenyl)-1,5-dihydro-4H-pyrrolo[2,3-d]pyridazin-4-one,
7-amino-3-((S)-1-((E)-3-((R)-azetidin-2-yl)acryloyl)pyrrolidin-3-yl)-1-(4-(2-fluorophenoxy)phenyl)-1,5-dihydro-4H-pyrrolo[2,3-d]pyridazin-4-one,
7-amino-3-((S)-1-((E)-3-((R)-azetidin-2-yl)acryloyl)pyrrolidin-3-yl)-1-(4-phenoxyphenyl)-1,5-dihydro-4H-pyrrolo[2,3-d]pyridazin-4-one,
7-amino-1-(4-(2-fluorophenoxy)phenyl)-3-((S)-1-((E)-3-((R)-1-methylazetidin-2-yl)acryloyl)pyrrolidin-3-yl)-1,5-dihydro-4H-pyrrolo[2,3-d]pyridazin-4-one,
7-amino-3-((S)-1-((E)-3-((R)-1-ethylazetidin-2-yl)acryloyl)pyrrolidin-3-yl)-1-(4-phenoxyphenyl)-1,5-dihydro-4H-pyrrolo[2,3-d]pyridazin-4-one,
7-amino-3-((S)-1-((E)-3-((R)-1-ethylazetidin-2-yl)acryloyl)pyrrolidin-3-yl)-1-(4-(2-fluorophenoxy)phenyl)-1,5-dihydro-4H-pyrrolo[2,3-d]pyridazin-4-one,
(S,E)-7-amino-3-(1-(4-methoxybut-2-enoyl)piperidin-3-yl)-1-(4-phenoxyphenyl)-1,5-dihydro-4H-pyrrolo[2,3-d]pyridazin-4-one,
(S,E)-7-amino-1-(4-(2-fluorophenoxy)phenyl)-3-(1-(4-methoxybut-2-enoyl)piperidin-3-yl)-1,5-dihydro-4H-pyrrolo[2,3-d]pyridazin-4-one,
(S,E)-7-amino-3-(1-(4-(dimethylamino)but-2-enoyl)piperidin-3-yl)-1-(4-phenoxyphenyl)-1,5-dihydro-4H-pyrrolo[2,3-d]pyridazin-4-one,
(S,E)-7-amino-3-(1-(4-(dimethylamino)but-2-enoyl)piperidin-3-yl)-1-(4-(2-fluorophenoxy)phenyl)-1,5-dihydro-4H-pyrrolo[2,3-d]pyridazin-4-one,
7-amino-3-((S)-1-((E)-3-((R)-azetidin-2-yl)acryloyl)piperidin-3-yl)-1-(4-phenoxyphenyl)-1,5-dihydro-4H-pyrrolo[2,3-d]pyridazin-4-one,
7-amino-3-((S)-1-((E)-3-((R)-azetidin-2-yl)acryloyl)piperidin-3-yl)-1-(4-(2-fluorophenoxy)phenyl)-1,5-dihydro-4H-pyrrolo[2,3-d]pyridazin-4-one,
7-amino-3-((S)-1-((E)-3-((R)-1-methylazetidin-2-yl)acryloyl)piperidin-3-yl)-1-(4-phenoxyphenyl)-1,5-dihydro-4H-pyrrolo[2,3-d]pyridazin-4-one,
7-amino-1-(4-(2-fluorophenoxy)phenyl)-3-((S)-1-((E)-3-((R)-1-methylazetidin-2-yl)acryloyl)piperidin-3-yl)-1,5-dihydro-4H-pyrrolo[2,3-d]pyridazin-4-one,
7-amino-3-((S)-1-((E)-3-((R)-1-ethylazetidin-2-yl)acryloyl)piperidin-3-yl)-1-(4-phenoxyphenyl)-1,5-dihydro-4H-pyrrolo[2,3-d]pyridazin-4-one,
7-amino-3-((S)-1-((E)-3-((R)-1-ethylazetidin-2-yl)acryloyl)piperidin-3-yl)-1-(4-(2-fluorophenoxy)phenyl)-1,5-dihydro-4H-pyrrolo[2,3-d]pyridazin-4-one,
3-(1-acryloylazetidin-3-yl)-7-amino-1-(4-(2-fluorophenoxy)phenyl)-1,5-dihydro-4H-pyrrolo[2,3-d]pyridazin-4-one,
3-(1-acryloylpiperidin-4-yl)-7-amino-1-(4-phenoxyphenyl)-1,5-dihydro-4H-pyrrolo[2,3-d]pyridazin-4-one,
3-(1-acryloylpiperidin-4-yl)-7-amino-1-(4-(2-fluorophenoxy)phenyl)-1,5-dihydro-4H-pyrrolo[2,3-d]pyridazin-4-one,
3-(1-acryloylazetidin-3-yl)-7-amino-1-(4-phenoxyphenyl)-1,5-dihydro-4H-pyrrolo[2,3-d]pyridazin-4-one,
(S)-3-(1-acryloylpyrrolidin-3-yl)-7-amino-1-(4-(2,5-difluorophenoxy)phenyl)-1,5-dihydro-4H-pyrrolo[2,3-d]pyridazin-4-one,
(S)-3-(1-acryloylpyrrolidin-3-yl)-7-amino-1-(4-(2-fluorophenoxy-3-d)phenyl)-1,5-dihydro-4H-pyrrolo[2,3-d]pyridazin-4-one,
(S)-7-amino-3-(1-(but-2-ynoyl)pyrrolidin-3-yl)-1-(4-(2-fluorophenoxy-3-d)phenyl)-1,5-dihydro-4H-pyrrolo[2,3-d]pyridazin-4-one,
and pharmaceutically acceptable salts thereof.

In another Embodiment (25), the invention provides a pharmaceutical composition comprising a compound of any one of Embodiments (1) to (25) or a pharmaceutically acceptable salts thereof and at least one pharmaceutically acceptable carrier.

In another Embodiment (26), the invention provides a method of treating, ameliorating or preventing a condition, which responds to inhibition of BTK, comprising administering to a subject in need of such treatment an effective amount of a compound of any one of Embodiments (1) to (25), or a pharmaceutically acceptable salt thereof, or of at least one pharmaceutical composition thereof, and optionally in combination with a second therapeutic agent.

In another Embodiment (27), the invention provides use of a compound of any one of Embodiments (1) to (25) or a pharmaceutically acceptable salt thereof in the preparation of a medicament for treating a cell-proliferative disorder.

In yet another of its aspects, there is provided a kit comprising a compound disclosed herein, or a pharmaceutically acceptable salts thereof; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound disclosed herein, or a pharmaceutically acceptable salts thereof; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound disclosed herein, or a pharmaceutically acceptable salts thereof.

In another of its aspects, there is provided a method of inhibiting a BTK kinase comprising contacting the BTK with a compound disclosed herein, or a pharmaceutically acceptable salts thereof.

In yet another of its aspects, there is provided a method of inhibiting a BTK comprising causing a compound disclosed herein, or a pharmaceutically acceptable salts thereof to be present in a subject in order to inhibit the BTK in vivo.

In a further of its aspects, there is provided a method of inhibiting BTK comprising administering a first compound to a subject that is converted in vivo to a second compound wherein the second compound inhibits the BTK in vivo, the second compound being a compound according to any one of the above embodiments and variations.

In another of its aspects, there is provided a method of treating a disease state for which a BTK possesses activity that contributes to the pathology and/or symptomology of the disease state, the method comprising causing a compound disclosed herein, or a pharmaceutically acceptable salts thereof to be present in a subject in a therapeutically effective amount for the disease state.

In a further of its aspects, there is provided a method of treating a disease state for which a BTK possesses activity that contributes to the pathology and/or symptomology of the disease state, the method comprising administering a first compound to a subject that is converted in vivo to a second compound wherein the second compound inhibits the BTK in vivo. It is noted that the compounds of the present invention may be the first or second compounds.

In one variation of each of the above methods the disease state is selected from the group consisting of cancerous hyperproliferative disorders (e.g., brain, lung, squamous cell, bladder, gastric, pancreatic, breast, head, neck, renal, kidney, ovarian, prostate, colorectal, epidermoid, esophageal, testicular, gynecological or thyroid cancer); non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, exzema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer); asthma; neutrophil chemotaxis (e.g., reperfusion injury in myocardial infarction and stroke and inflammatory arthritis); septic shock; T-cell mediated diseases where immune suppression would be of value (e.g., the prevention of organ transplant rejection, graft versus host disease, lupus erythematosus, multiple sclerosis, and rheumatoid arthritis); atherosclerosis; inhibition of keratinocyte responses to growth factor cocktails; chronic obstructive pulmonary disease (COPD) and other diseases.

In another of its aspects, there is provided a method of treating a disease state for which a mutation in the BTK gene contributes to the pathology and/or symptomology of the disease state including, for example, melanomas, lung cancer, colon cancer and other tumor types.

In still another of its aspects, the present invention relates to the use of a compound of any of the above embodiments and variations as a medicament. In yet another of its aspects, the present invention relates to the use of a compound according to any one of the above embodiments and variations in the manufacture of a medicament for inhibiting a BTK.

In a further of its aspects, the present invention relates to the use of a compound according to any one of the above embodiments and variations in the manufacture of a medicament for treating a disease state for which a BTK possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 1000 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof, glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

Combination Therapies

The compounds or pharmaceutical acceptable salts of the disclosure may be administered as the sole therapy, or together with other therapeutic agent or agents.

For example, the therapeutic effectiveness of one of the compounds described herein may be enhanced by administration of an adjuvant (i.e. by itself the adjuvant may only have minimal therapeutic benefit, but in combination with another therapeutic agent, the overall therapeutic benefit to the individual is enhanced). Or, by way of example only, the benefit experienced by an individual may be increased by administering one of the compounds described herein with another therapeutic agent that also has therapeutic benefit. By way of example only, in a treatment for gout involving administration of one of the compounds described herein, increased therapeutic benefit may result by also providing the individual with another therapeutic agent for gout. Or, by way of example only, if one of the side effects experienced by an individual upon receiving one of the compounds described herein is nausea, then it may be appropriate to administer an anti-nausea agent in combination with the compound. Or, the additional therapy or therapies include, but are not limited to physiotherapy, psychotherapy, radiation therapy, application of compresses to a diseased area, rest, altered diet, and the like. Regardless of the disease, disorder or condition being treated, the overall benefit experienced by the individual may be additive of the two therapies or the individual may experience a synergistic benefit.

In the instances where the compounds described herein are administered in combination with other therapeutic agents, the compounds described herein may be administered in the same pharmaceutical composition as other therapeutic agents, or because of different physical and chemical characteristics, be administered by a different route. For example, the compounds described herein may be administered orally to generate and maintain good blood levels thereof, while the other therapeutic agent may be administered intravenously. Thus the compounds described herein may be administered concurrently, sequentially or dosed separately to other therapeutic agents.

Compounds having Formula (II) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

EXAMPLES

Various methods may be developed for synthesizing a compound of formula (II) or a pharmaceutically acceptable salt thereof. Representative methods for synthesizing a compound of formula (II) or a pharmaceutically acceptable salt thereof are provided in the Examples. It is noted, however, that a compound of formula (II) or a pharmaceutically acceptable salt thereof may also be synthesized by other synthetic routes that others may devise.

It will be readily recognized that certain compounds of formula (II) have atoms with linkages to other atoms that confer a particular stereochemistry to the compound (e.g., chiral centers). It is recognized that synthesis of a compound of formula (II) or a pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

A compound of formula (II) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (II) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (II) are set forth in the definitions section of this Application. Alternatively, the salt forms of the compounds of formula (II) can be prepared using salts of the starting materials or intermediates.

The free acid or free base forms of the compounds of formula (II) can be prepared from the corresponding base addition salt or acid addition salt form. For example, a compound of formula (II) in an acid addition salt form can be converted to the corresponding free base thereof by treating with a suitable base (e.g., ammonium hydroxide solution, sodium hydroxide, and the like). A compound of formula (II) in a base addition salt form can be converted to the corresponding free acid thereof by, for example, treating with a suitable acid (e.g., hydrochloric acid, etc).

The N-oxides of the a compound of formula (II) or a pharmaceutically acceptable salt thereof can be prepared by methods known to those of ordinary skill in the art. For example, N-oxides can be prepared by treating an unoxidized form of the compound of formula (II) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (II) can be prepared from the N-oxide of an appropriate starting material.

Compounds of formula (II) in an unoxidized form can be prepared from N-oxides of compounds of formula (II) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (II) can be made by methods known to those of ordinary skill in the art. A detailed description of the techniques applicable to the creation of protecting groups and their removal can be found in T.W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); μL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); m-CPBA (meta-chloroperbenzoic acid).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm Superchemgroup silica gel plates (60F-254), visualized with UV light, 5% ethanolic phosphomolybdic acid, ninhydrin, or p-anisaldehyde solution. Flash column chromatography was performed on silica gel (200-300 mesh, Branch of Qingdao Haiyang Chemical Co., Ltd).

Synthetic Schemes

At least one compound of formula I and/or at least one pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T.W. Greene and P. G. M. Wuts in "Protective Groups in Organic Chemistry" John Wiley and Sons, 1991.

Synthetic methods for preparing the compounds of the present invention are illustrated in the following Schemes and Examples. Starting materials are commercially available or may be made according to procedures known in the art or as illustrated herein.

The intermediates shown in the following schemes are either known in the literature or may be prepared by a variety of methods familiar to those skilled in the art.

As an illustration of the synthesis of compounds of formula I of the present disclosure, one of the synthetic approaches of the compound of formula Ia is outlined in Scheme 1. Starting from cyano compound IA-a which is either commercially available or can be prepared according to procedures known in the literature, beta cyano aldehyde IA-b can be readily prepared by condensation of IA-a with formyl ester in the presence of a base such as LiHMDS. Further reaction of IA-b with analines of formula IA-c provides intermediate IA-d which is converted to amino pyrrole IA-e via intramolecular cyclization reaction effected by a base such as t-BuONa. Ester IA-g can be prepared from amino pyrrole IA-e via a sequence of diazotization and carbomonoxylation reactions. Reaction of ester IA-g with hydrazines of formula IA-h provides amino pyridazone IA-i. Replacement of the protecting group in IA-i with appropriate functional groups through multi-steps reactions known in the literature leads to IA.

As a further illustration of the preparation compounds of formula I of the present disclosure, one of the synthetic approaches of the compound of formula IB is outlined in Scheme 2. Reaction of beta cyano aldehyde IA-b with diazo compounds of formula IB-a provides hydrazine IB-b. Alkylation of hydrazine IB-b with halo acetonitrile IB-c followed by in situ intramolecular cyclization in the presence of a base such as t-BuONa leads to amino pyrazole IB-d. IB can be prepared from amino pyrazole IB-d following essentially the same procedures as described for the transformation of IA-e to IA shown in Scheme 1.

Scheme 1

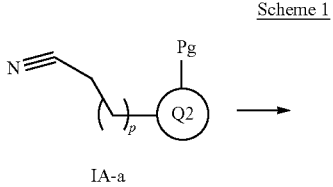

IA-a

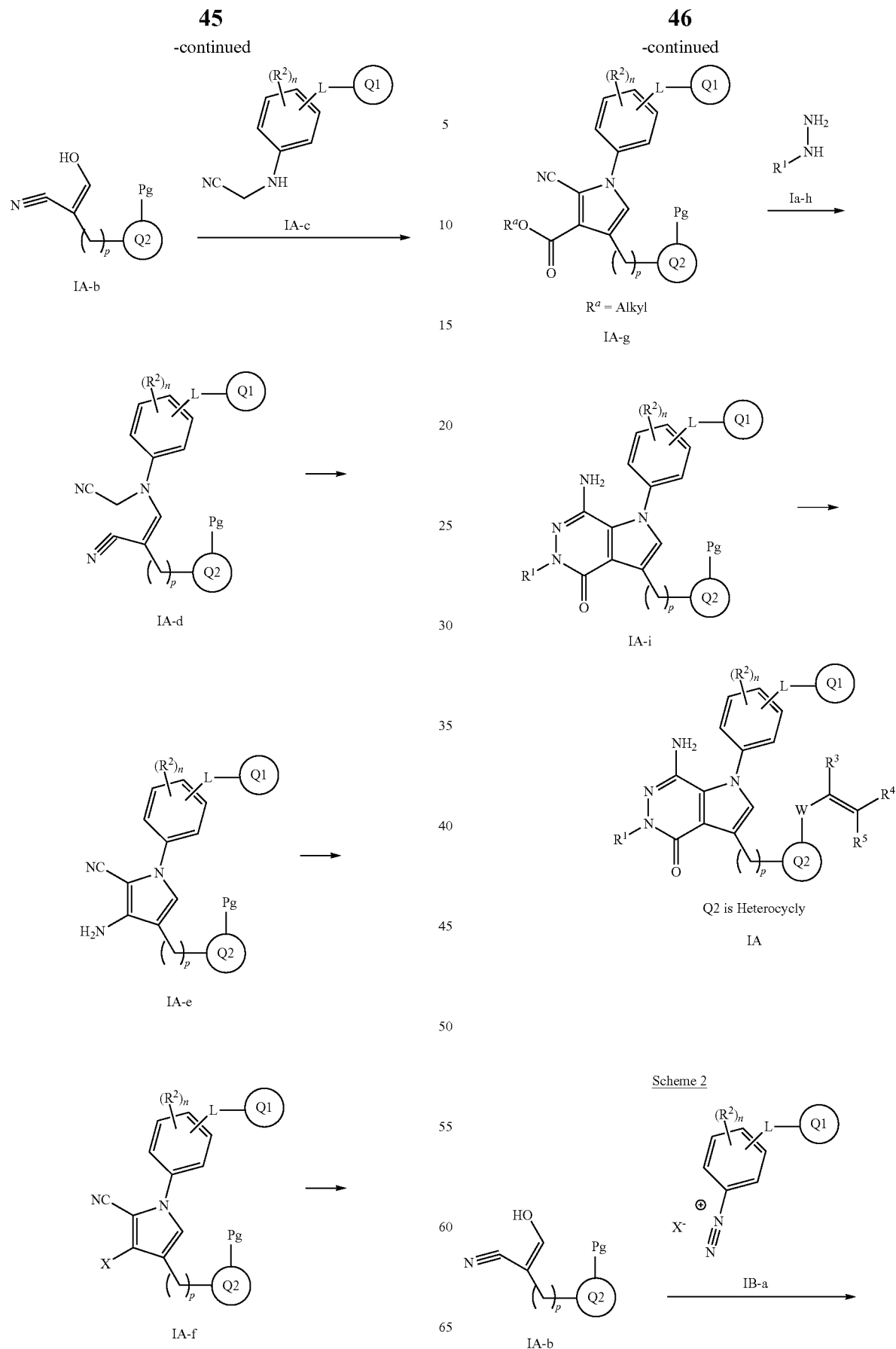

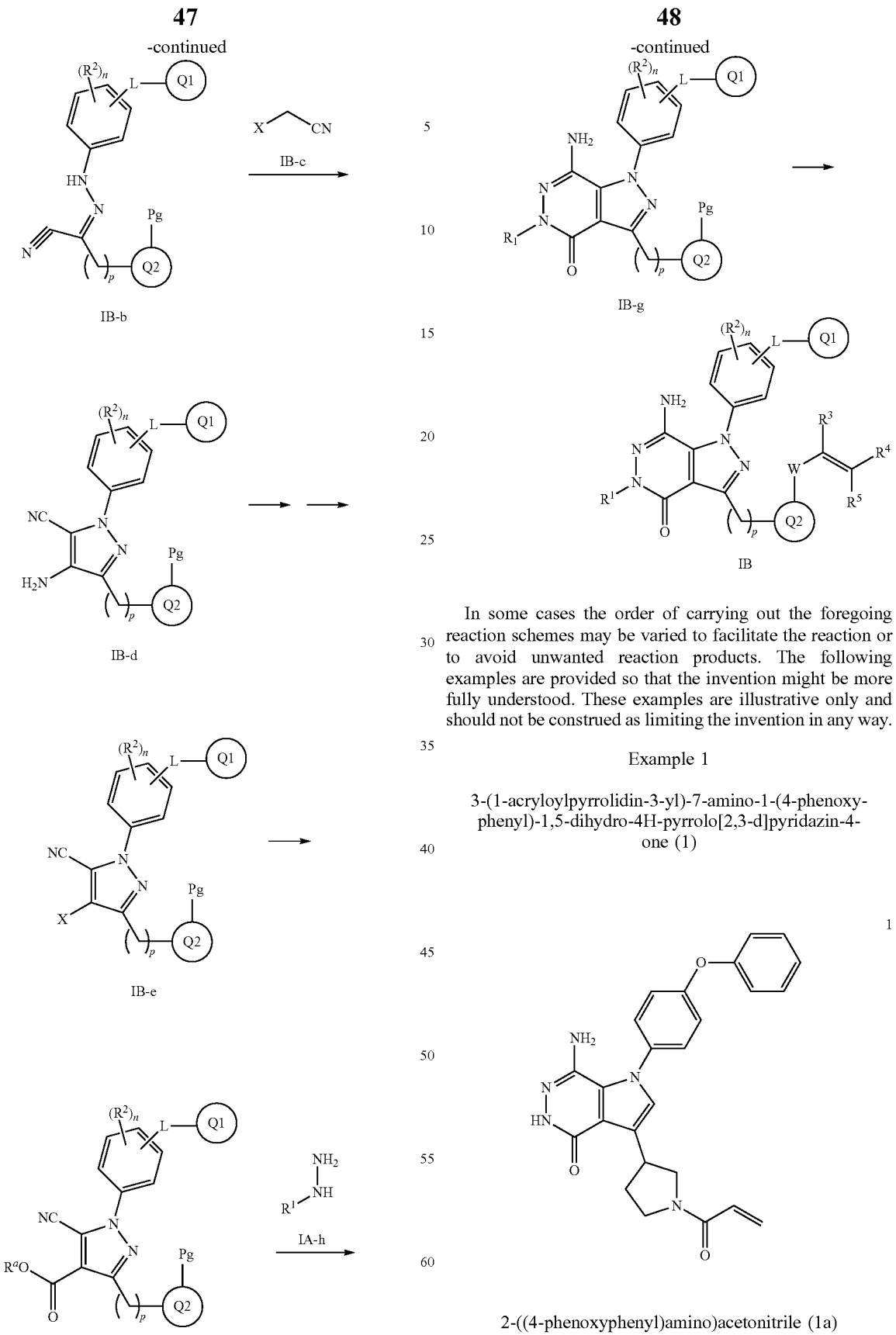

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Example 1

3-(1-acryloylpyrrolidin-3-yl)-7-amino-1-(4-phenoxyphenyl)-1,5-dihydro-4H-pyrrolo[2,3-d]pyridazin-4-one (1)

2-((4-phenoxyphenyl)amino)acetonitrile (1a)

The title compound 2-((4-phenoxyphenyl)amino)acetonitrile (1a) was prepared according to the method described in US 2015/0005277.

tert-butyl (E)-3-(cyanomethylene)pyrrolidine-1-carboxylate (1b)

To a mixture of tert-butyl 3-oxopyrrolidine-1-carboxylate (0.20 g, 1.08 mmol) and 2-cyanoacetic acid (0.18 g, 2.16 mmol) in pyridine (2 mL) at 25° C. was added piperidine (28 mg, 0.32 mmol). After stirring at reflux for 12 h, the mixture was diluted with water (20 mL), and then extracted with EtOAc (2×30 mL), washed with brine, dried and concentrated. The residue was purified by flash column chromatography on silica gel eluting with PE/EtOAc (6:1-5:1) to give the title compound tert-butyl (E)-3-(cyanomethylene) pyrrolidine-1-carboxylate (1b). MS-ESI (m/z): 209 [M+1-15]$^+$.

tert-butyl 3-(cyanomethyl)pyrrolidine-1-carboxylate (1c)

The mixture of tert-butyl (E)-3-(cyanomethylene)pyrrolidine-1-carboxylate (1b) (0.10 g, 0.48 mmol) and Pd/C (20 mg) in EtOH (2 mL) was stirred at ambient temperature for 3 h at the atmosphere of $H_2$ (1 atm). Then the mixture was filtered, and the filtrate was concentrated to give the title compound tert-butyl 3-(cyanomethyl)pyrrolidine-1-carboxylate (1c). MS-ESI(m/z): 211 [M+1]$^+$.

tert-butyl 3-(1-cyano-2-oxoethyl)pyrrolidine-1-carboxylate (1d)

To a solution of tert-butyl 3-(cyanomethyl)pyrrolidine-1-carboxylate (1c) (190 mg, 0.90 mmol) in THF (5 mL) at −78° C. under $N_2$ was added LiHMDS (1.0 M, 4.5 mL, 4.5 mmol) and the resulting mixture was stirred at −78° C. for 1 h. Then ethyl formate (0.73 mL, 9.0 mmol) was added dropwise to the mixture at −78° C. and the resulting mixture was stirred at −78° C. for 30 min. The reaction was quenched with $NH_4Cl$ (10 mL). The mixture was adjusted to pH=2, extracted with EtOAc (2×30 mL), washed with brine, dried and concentrated. The residue was purified by flash column chromatography on silica gel eluting with PE/EtOAc (10:1) to give the title compound tert-butyl 3-(1-cyano-2-oxoethyl)pyrrolidine-1-carboxylate (1d). MS-ESI (m/z): 224 [M+1-15]$^+$.

tert-butyl (Z)-3-(1-cyano-2-((cyanomethyl)(4-phenoxyphenyl)amino)vinyl)-pyrrolidine-1-carboxylate (1e)

To a mixture of tert-butyl 3-(1-cyano-2-oxoethyl)pyrrolidine-1-carboxylate (1d) (39 g, 0.11 mmol) and 2-((4-phenoxyphenyl)amino)acetonitrile (1a) (24 mg, 0.11 mmol) in toluene (1.5 mL) was added p-TsOH (1.5 mg, 0.01 mmol). The mixture was stirred at reflux for 12 h. After cooling down to ambient temperature, the mixture was concentrated. The residue was purified by column chromatography on silica gel eluting with PE/EtOAc (10:1~2:1) to give the title compound tert-butyl (Z)-3-(1-cyano-2-((cyanomethyl)(4-phenoxyphenyl)amino)vinyl)-pyrrolidine-1-carboxylate (1e). MS-ESI (m/z): 430 [M+1-15]$^+$.

tert-butyl 3-(4-amino-5-cyano-1-(4-phenoxyphenyl)-1H-pyrrol-3-yl)pyrrolidine-1-carboxylate (1f)

To a solution of tert-butyl (Z)-3-(1-cyano-2-((cyanomethyl)(4-phenoxyphenyl)amino)vinyl)pyrrolidine-1-carboxylate (1e) (120 mg, 0.27 mmol) in t-BuOH (50 mL) was added t-BuOK (45 mg, 0.4 mmol) at 25° C. Then the reaction mixture was warmed to 70° C., and stirred for 1 h. The mixture was then diluted with DCM (50 mL), washed sequentially with water (2×30 mL) and brine (50 mL), dried over $Na_2SO_4$, and evaporated to give title compound tert-butyl 3-(4-amino-5-cyano-1-(4-phenoxyphenyl)-1H-pyrrol-3-yl)pyrrolidine-1-carboxylate (1f). MS-ESI (m/z): 445 [M+1]$^+$.

tert-butyl 3-(4-bromo-5-cyano-1-(4-phenoxyphenyl)-1H-pyrrol-3-yl)pyrrolidine-1-carboxylate (1g)

To a solution of tert-butyl 3-(4-amino-5-cyano-1-(4-phenoxyphenyl)-1H-pyrrol-3-yl)pyrrolidine-1-carboxylate (1f) (122 mg, 0.27 mmol) in $HCBr_3$ (1.5 mL) was added dropwise tert-butyl nitrite (65 μL, 0.55 mmol) at 0° C. Then the reaction mixture was warmed to 70° C. and stirred for 1 h. The mixture was diluted with DCM (20 mL), washed sequentially with water (2×20 mL) and brine (20 mL), dried over $Na_2SO_4$ and evaporated. The residue was purified by column chromatography on silica gel eluting with PE/EtOAc (2:1) to give title compound tert-butyl 3-(4-bromo-5-cyano-1-(4-phenoxyphenyl)-1H-pyrrol-3-yl)pyrrolidine-1-carboxylate (1g). MS-ESI (m/z): 508 [M+1]$^+$.

tert-butyl 3-(4-bromo-5-cyano-1-(4-phenoxyphenyl) 1H-pyrrol-3-yl)pyrrolidine-1-carboxylate (1h)

A mixture of 3-(4-bromo-5-cyano-1-(4-phenoxyphenyl)-1H-pyrrol-3-yl)pyrrolidine-1-carboxylate (1g) (0.11 g, 0.22 mmol), TEA (94 μL, 0.65 mmol) and Pd(dppf)$_2$Cl$_2$ (50 mg, 0.065 mmol) in n-BuOH (5 mL) was stirred at 115° C. for 12 h at the atmosphere of CO. The mixture was cooled to r.t. and concentrated. The residue was purified by column chromatography on silica gel eluting with PE/EtOAc (8:1) to give the title compound butyl 4-(1-(tert-butoxycarbonyl)pyrrolidin-3-yl)-2-cyano-1-(4-phenoxyphenyl)-1H-pyrrole-3-carboxylate (1h). MS-ESI (m/z): 530 [M+1]$^+$.

tert-butyl 3-(7-amino-4-oxo-1-(4-phenoxyphenyl)-4,5-dihydro-1H-pyrrolo[2,3-d]pyridazin-3-yl)pyrrolidine-1-carboxylate (1i)

A mixture of butyl 4-(1-(tert-butoxycarbonyl)pyrrolidin-3-yl)-2-cyano-1-(4-phenoxyphenyl)-1H-pyrrole-3-carboxylate (1h) (0.1 g, 1.9 mmol) and hydrazine hydrate (7 mL) in EtOH (15 mL) was stirred at 110° C. for 8 h in seal tube. The mixture was diluted with water (50 mL), and extracted with DCM (2×50 mL). The organic phase was washed sequentially with water (20 mL) and brine (20 mL), dried and concentrated. The residue was purified by column chromatography on silica gel eluting with PE/EtOAc (2:1) to give the title compound tert-butyl 3-(7-amino-4-oxo-1-(4-phenoxyphenyl)-4,5-dihydro-1H-pyrrolo[2,3-d]pyridazin-3-yl) pyrrolidine-1-carboxylate (1i). MS-ESI (m/z): 488 [M+1]$^+$.

7-amino-1-(4-phenoxyphenyl)-3-(pyrrolidin-3-yl)-1,5-dihydro-4H-pyrrolo[2,3-d]pyridazin-4-one (1j)

A mixture of tert-butyl 3-(7-amino-4-oxo-1-(4-phenoxyphenyl)-4,5-dihydro-1H-pyrrolo[2,3-d]pyridazin-3-yl)pyrrolidine-1-carboxylate (1i) (20 mg, 0.041 mmol) in HCl/EA (7 M 2.5 mL) was stirred at 25° C. for 1 h. The mixture was concentrated to give the title compound 7-amino-1-(4-phenoxyphenyl)-3-(pyrrolidin-3-yl)-1,5-dihydro-4H-pyrrolo[2,3-d]pyridazin-4-one (1j). MS-ESI (m/z): 388 [M+1]+.

3-(1-acryloylpyrrolidin-3-yl)-7-amino-1-(4-phenoxy-phenyl)-1,5-dihydro-4H-pyrrolo[2,3-d]pyridazin-4-one (1)

To a solution of 7-amino-1-(4-phenoxyphenyl)-3-(pyrrolidin-3-yl)-1,5-dihydro-4H-pyrrolo[2,3-d]pyridazin-4-one (1j) (9.4 mg, 0.022 mmol) and TEA (13 µL, 0.088 mmol) in DCM (2 mL) was added acryloyl chloride (2.0 mg, 0.022 mmol). The mixture was stirred at r.t. for 0.5 h. The mixture was washed sequentially with saturated NaHCO₃ aqueous solution (10 mL), and brine (10 mL), dried over Na₂SO₄ and evaporated. The residue was purified by column chromatography on silica gel eluting with DCM/MeOH (15:1) to give title compound 3-(1-acryloylpyrrolidin-3-yl)-7-amino-1-(4-phenoxyphenyl)-1,5-dihydro-4H-pyrrolo[2,3-d]pyridazin-4-one (1). MS-ESI (m/z): 442 [M+1]⁺.

Example 2

7-amino-3-(1-(but-2-ynoyl)pyrrolidin-3-yl)-1-(4-phenoxyphenyl)-1,5-dihydro-4H-pyrrolo[2,3-d]pyridazin-4-one (2)

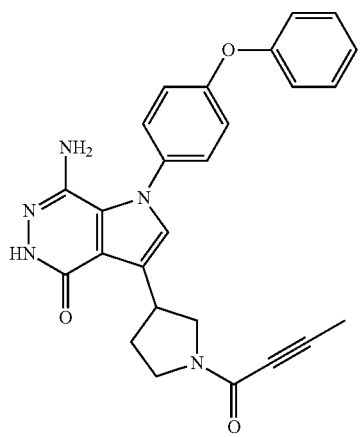

A mixture 7-amino-1-(4-phenoxyphenyl)-3-(pyrrolidin-3-yl)-1,5-dihydro-4H-pyrrolo[2,3-d]pyridazin-4-one (1j) (9.4 mg, 0.022 mmol), but-2-ynoic acid (1.9 mg, 0.024 mmol), EDCI (8.4 mg, 0.044 mmol), HOBT (6.0 mg, 0.044 mmol) and TEA (13 uL, 0.088 mmol) in DMF (1 mL) was stirred at r.t. for 12 h, diluted with water (10 mL), and extracted with EA (2×10 mL). The organic phase was washed sequentially with water (10 mL) and brine (10 mL), dried, and evaporated. The residue was purified by column chromatography on silica gel eluting with DCM/MeOH (15:1) to give title compound 7-amino-3-(1-(but-2-ynoyl)pyrrolidin-3-yl)-1-(4-phenoxyphenyl)-1,5-dihydro-4H-pyrrolo[2,3-d]pyridazin-4-one (2). MS-ESI (m/z): 454 [M+1]⁺.

Example 3

3-(1-acryloylpyrrolidin-3-yl)-7-amino-1-(4-(2,6-difluorophenoxy)phenyl)-1,5-dihydro-4H-pyrrolo[2,3-d]pyridazin-4-one (3)

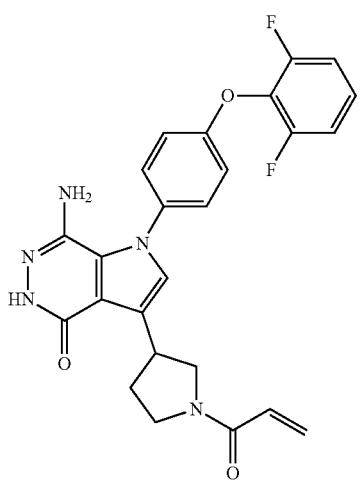

4-(2,6-difluorophenoxy)aniline (3a)

The title compound 4-(2,6-difluorophenoxy)aniline (3a) was prepared according to the method described in WO2012/158795.

3-(1-acryloylpyrrolidin-3-yl)-7-amino-1-(4-(2,6-difluorophenoxy)phenyl)-1,5-dihydro-4H-pyrrolo[2,3-d]pyridazin-4-one (3)

The title compound 3-(1-acryloylpyrrolidin-3-yl)-7-amino-1-(4-(2,6-difluorophenoxy)phenyl)-1,5-dihydro-4H-pyrrolo[2,3-d]pyridazin-4-one (3) was prepared according to the synthetic method of 1 by replacing 4-phenoxyaniline with 4-(2,6-difluorophenoxy)aniline (3a). MS-ESI (m/z): 478 [M+1]⁺.

Example 4

7-amino-3-(1-(but-2-ynoyl)pyrrolidin-3-yl)-1-(4-(2,6-difluorophenoxy)phenyl)-1,5-dihydro-4H-pyrrolo[2,3-d]pyridazin-4-one (4)

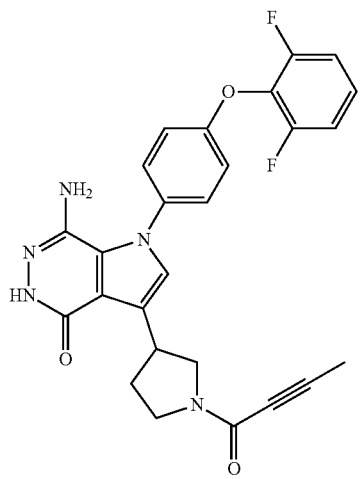

The title compound 7-amino-3-(1-(but-2-ynoyl)pyrrolidin-3-yl)-1-(4-(2,6-difluorophenoxy)phenyl)-1,5-dihydro-4H-pyrrolo[2,3-d]pyridazin-4-one (4) was prepared according to the synthetic method of 2 by replacing 4-phenoxyaniline with 4-(2,6-difluorophenoxy)aniline (3a). MS-ESI (m/z): 490 [M+1]$^+$.

Example 5

3-(1-acryloylpyrrolidin-3-yl)-7-amino-1-(4-phenoxyphenyl)-1,5-dihydro-4H-pyrazolo[3,4-d]pyridazin-4-one (5)

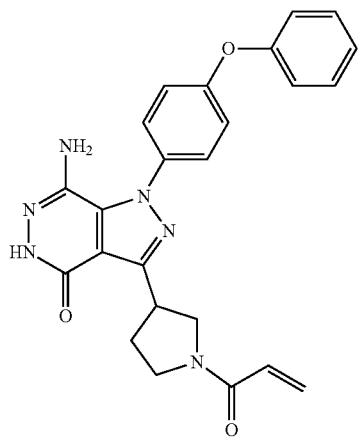

tert-butyl (Z)-3-(1-cyano-2-ethoxy-2-oxoethylidene)pyrrolidine-1-carboxylate (5a)

A mixture of tert-butyl 3-oxopyrrolidine-1-carboxylate (1.0 g, 5.3 mmol), ethyl 2-cyanoacetate (0.61 g, 5.3 mmol), NH$_4$OAc (62 mg, 0.80 mmol) and HOAc (95 mg, 1.6 mmol) in toluene (20 mL) was stirred at 110° C. for 12 h. The mixture was concentrated. The residue was purified by column chromatography on silica gel eluting with PE/EtOAc (10:1-5:1) to give the title compound tert-butyl (Z)-3-(1-cyano-2-ethoxy-2-oxoethylidene)pyrrolidine-1-carboxylate (5a). MS-ESI (m/z): 281 [M+1]$^+$.

tert-butyl 3-(1-cyano-2-ethoxy-2-oxoethyl)pyrrolidine-1-carboxylate (5b)

The mixture of tert-butyl (Z)-3-(1-cyano-2-ethoxy-2-oxoethylidene)pyrrolidine-1-carboxylate (5a) (1.1 g, 3.9 mmol) and Pd/C (220 mg) in MeOH (20 mL) was stirred at ambient temperature for 2 h at the atmosphere of H$_2$ (1 atm). Then the mixture was filtered, and the filtrate was concentrated to give the title compound tert-butyl 3-(1-cyano-2-ethoxy-2-oxoethyl)-pyrrolidine-1-carboxylate (5b). MS-ESI(m/z): 283 [M+1]$^+$.

4-phenoxybenzenediazonium (5c)

To a solution of 4-phenoxyaniline (1.0 g, 5.4 mmol) in HCl (40 mL) was added NaNO$_2$ (746 mg, 10.8 mmol) (in 2 mL H$_2$O). The mixture was stirred at –10° C. for 1 h to give the crude product of title compound 4-phenoxybenzenediazonium (5c), which was used in the next step without further purification. MS-ESI (m/z): 197 [M]$^+$.

tert-butyl (E)-3-(1-cyano-2-ethoxy-2-oxo-1-((4-phenoxyphenyl)diazenyl)ethyl)-pyrrolidine-1-carboxylate (5d)

To a solution of tert-butyl 3-(1-cyano-2-ethoxy-2-oxoethyl)pyrrolidine-1-carboxylate (5b) (1.0 g, 3.5 mmol) in H$_2$O (100 mL) and EtOH (10 mL) was added 4-phenoxybenzenediazonium (5c) (746 mg, 10.8 mmol) (in 40 mL HCl) at 0° C. The pH was maintained at 6-7 by added NaOAc in portions. The reaction was quenched by NH$_4$Cl (10 mL), and extracted with EA (2×50 mL). The organic phase was washed sequentially with water (50 mL) and brine (50 mL), dried, and evaporated. The residue was purified by column chromatography on silica gel eluting with PE/EtOAc (10:1-5:1-3:1) to give title compound tert-butyl (E)-3-(1-cyano-2-ethoxy-2-oxo-1-((4-phenoxyphenyl)diazenyl)ethyl)pyrrolidine-1-carboxylate (5d). MS-ESI (m/z): 423 [M+1–56]$^+$.

tert-butyl (Z)-3-(cyano(2-(4-phenoxyphenyl)hydrazono)methyl)pyrrolidine-1-carboxylate (5e)

To a solution of tert-butyl (E)-3-(1-cyano-2-ethoxy-2-oxo-1-((4-phenoxyphenyl)diazenyl)ethyl)pyrrolidine-1-carboxylate (5d) (400 mg, 0.836 mmol) in THF (20 mL) was added NaOH (10 N) (2.0 mg, 0.022 mmol). The mixture was stirred at r.t. for 1.5 h. The reaction was quenched by NH$_4$Cl (10 mL), and extracted with EA (2×50 mL). The organic phase was washed sequentially with water (50 mL) and brine (50 mL), dried, and evaporated to give title compound tert-butyl (Z)-3-(cyano(2-(4-phenoxyphenyl)hydrazono)methyl)pyrrolidine-1-carboxylate (5e). MS-ESI (m/z): 407 [M+1]$^+$.

tert-butyl 3-(4-amino-5-cyano-1-(4-phenoxyphenyl)-1H-pyrazol-3-yl)pyrrolidine-1-carboxylate (5f)

To a solution of tert-butyl (Z)-3-(cyano(2-(4-phenoxyphenyl)hydrazono)methyl)-pyrrolidine-1-carboxylate (5e) (374 mg, 0.92 mmol) and 2-bromoacetonitrile (96 μL, 1.38 mmol) in t-BuOH (8 mL) was added t-BuONa (265 mg, 2.76 mmol). The mixture was stirred at r.t. for 1.5 h. The reaction was quenched by NH₄Cl (10 mL), and extracted with EA (2×50 mL). The organic phase was washed sequentially with water (50 mL) and brine (50 mL), dried, and evaporated to give title compound tert-butyl 3-(4-amino-5-cyano-1-(4-phenoxyphenyl)-1H-pyrazol-3-yl)pyrrolidine-1-carboxylate (5f). MS-ESI (m/z): 446 [M+1×56]⁺.

3-(1-acryloylpyrrolidin-3-yl)-7-amino-1-(4-phenoxyphenyl)-1,5-dihydro-4H-pyrazolo[3,4-d]pyridazin-4-one (5)

The title compound 3-(1-acryloylpyrrolidin-3-yl)-7-amino-1-(4-phenoxyphenyl)-1,5-dihydro-4H-pyrazolo[3,4-d]pyridazin-4-one (5) was prepared according to the synthetic method of 1 by replacing tert-butyl 3-(4-amino-5-cyano-1-(4-phenoxyphenyl)-1H-pyrrol-3-yl)pyrrolidine-1-carboxylate (1f) with tert-butyl 3-(4-amino-5-cyano-1-(4-phenoxyphenyl)-1H-pyrazol-3-yl)pyrrolidine-1-carboxylate (5f). MS-ESI (m/z): 443 [M+1]⁺.

Example 6

7-amino-3-(1-(but-2-ynoyl)pyrrolidin-3-yl)-1-(4-phenoxyphenyl)-1,5-dihydro-4H-pyrazolo[3,4-d]pyridazin-4-one (6)

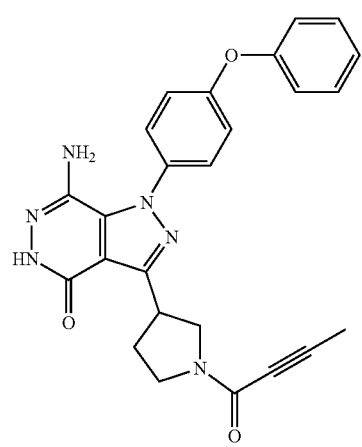

6

The title compound 7-amino-3-(1-(but-2-ynoyl)pyrrolidin-3-yl)-1-(4-phenoxyphenyl)-1,5-dihydro-4H-pyrazolo[3,4-d]pyridazin-4-one (6) was prepared according to the synthetic method of 2 by replacing tert-butyl 3-(4-amino-5-cyano-1-(4-phenoxyphenyl)-1H-pyrrol-3-yl)pyrrolidine-1-carboxylate (1f) with tert-butyl 3-(4-amino-5-cyano-1-(4-phenoxyphenyl)-1H-pyrazol-3-yl)pyrrolidine-1-carboxylate (5f). MS-ESI (m/z): 455 [M+1]⁺.

Example 7

3-(1-acryloylpyrrolidin-3-yl)-7-amino-1-(4-(2,6-difluorophenoxy)phenyl)-1,5-dihydro-4H-pyrazolo[3,4-d]pyridazin-4-one (7)

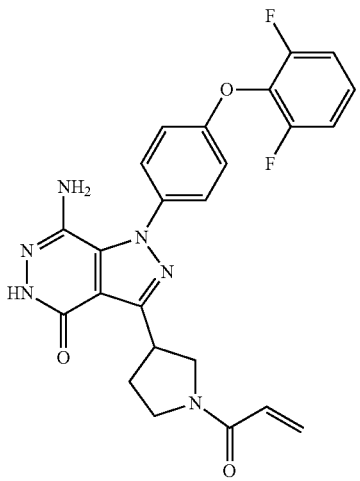

7

The title compound 3-(1-acryloylpyrrolidin-3-yl)-7-amino-1-(4-(2,6-difluorophenoxy)phenyl)-1,5-dihydro-4H-pyrazolo[3,4-d]pyridazin-4-one (7) was prepared according to the synthetic method of 5 by replacing 4-phenoxyaniline with 4-(2,6-difluorophenoxy)aniline (3a). MS-ESI (m/z): 479 [M+1]⁺.

Example 8

7-amino-3-(1-(but-2-ynoyl)pyrrolidin-3-yl)-1-(4-(2,6-difluorophenoxy)phenyl)-1,5-dihydro-4H-pyrazolo[3,4-d]pyridazin-4-one (8)

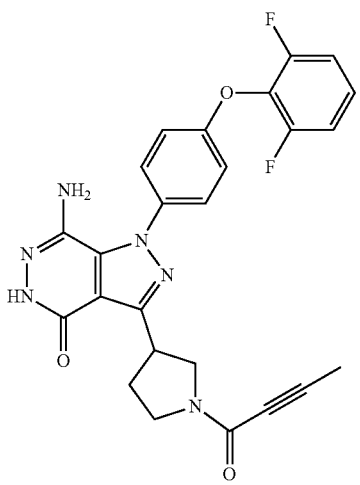

8

The title compound 7-amino-3-(1-(but-2-ynoyl)pyrrolidin-3-yl)-1-(4-phenoxyphenyl)-1,5-dihydro-4H-pyrazolo[3,4-d]pyridazin-4-one (8) was prepared according to the synthetic method of 6 by replacing 4-phenoxyaniline with 4-(2,6-difluorophenoxy)aniline (3a). MS-ESI (m/z): 491 [M+1]⁺.

Example 9

(S)-3-(1-acryloylpyrrolidin-3-yl)-7-amino-1-(4-phenoxyphenyl)-1,5-dihydro-4H-pyrrolo[2,3-d]pyridazin-4-one (9)

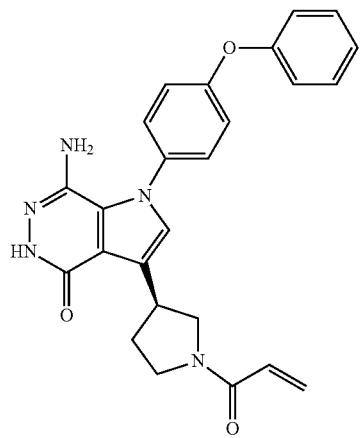

tert-butyl (S)-3-(cyanomethyl)pyrrolidine-1-carboxylate (9a)

The title compound tert-butyl (S)-3-(cyanomethyl)pyrrolidine-1-carboxylate (9a) was prepared according to the method described in WO2014/71368.

tert-butyl (S)-3-((R)-1-cyano-2-oxoethyl)pyrrolidine-1-carboxylate (9b)

To a solution of tert-butyl (S)-3-(cyanomethyl)pyrrolidine-1-carboxylate (9a) (330 mg, 1.6 mmol) in THF (6.6 mL) was added LiHMDS (1.0 M, 4.7 mL, 4.7 mmol) at −78° C. under $N_2$ and the resulting mixture was stirred at −78° C. for 1 h. Then ethyl formate (230 mg, 3.1 mmol) was added dropwise to the mixture at −78° C. and the resulting mixture was stirred at −78° C. for 30 min. The reaction was quenched by adjusting the pH of the mixture to 2 with 6 N HCl. Then the mixture was extracted with EtOAc (2×30 mL), washed with brine, dried and concentrated. The residue was used in the next step without further purification. MS-ESI (m/z): 224 [M+1×15]⁺.

tert-butyl (S,Z)-3-(1-cyano-2-((cyanomethyl)(4-phenoxyphenyl)amino)vinyl)pyrrolidine-1-carboxylate (9c)

To a mixture of tert-butyl (S)-3-((R)-1-cyano-2-oxoethyl) pyrrolidine-1-carboxylate (9b) (374 mg, 1.6 mmol) and 2-((4-phenoxyphenyl)amino)acetonitrile (1a) (352 mg, 1.6 mmol) in toluene (10 mL) was added p-TsOH (30 mg, 0.17 mmol). The mixture was stirred at reflux for 12 h. After cooling down to ambient temperature, the mixture was concentrated. The residue was purified by column chromatography on silica gel eluting with PE/EtOAc (10:1~2:1) to give the title compound tert-butyl (S,Z)-3-(1-cyano-2-((cyanomethyl)(4-phenoxyphenyl)amino)vinyl)pyrrolidine-1-carboxylate (9c). MS-ESI (m/z): 430 [M+1×15]⁺.

tert-butyl (S)-3-(4-amino-5-cyano-1-(4-phenoxyphenyl)-1H-pyrrol-3-yl)pyrrolidine-1-carboxylate (9d)

To a solution of (S,Z)-3-(1-cyano-2-((cyanomethyl)(4-phenoxyphenyl)amino)vinyl)pyrrolidine-1-carboxylate (9c) (230 mg, 0.56 mmol) in t-BuOH (90 mL) was added t-BuOK (87 mg, 0.78 mmol) at 25° C. Then the reaction mixture was warmed to 70° C., and stirred for 1 h. The mixture was then diluted with DCM (50 mL), washed sequentially with water (2×30 mL) and brine (50 mL), dried over $Na_2SO_4$, and evaporated to give title compound tert-butyl (S)-3-(4-amino-5-cyano-1-(4-phenoxyphenyl)-1H-pyrrol-3-yl)pyrrolidine-1-carboxylate (9d). MS-ESI (m/z): 445 [M+1]⁺.

tert-butyl (S)-3-(4-bromo-5-cyano-1-(4-phenoxyphenyl)-1H-pyrrol-3-yl)pyrrolidine-1-carboxylate (9e)

To a solution of tert-butyl (S)-3-(4-amino-5-cyano-1-(4-phenoxyphenyl)-1H-pyrrol-3-yl)pyrrolidine-1-carboxylate (9d) (216 mg, 0.48 mmol) in $HCBr_3$ (4.3 mL) was added dropwise tert-butyl nitrite (150 mg, 1.4 mmol) at 0° C. Then the reaction mixture was warmed to 70° C. and stirred for 1 h. The mixture was diluted with DCM (20 mL), washed sequentially with water (2×20 mL) and brine (20 mL), dried over $Na_2SO_4$ and evaporated. The residue was purified by column chromatography on silica gel eluting with PE/EtOAc (2:1) to give title compound tert-butyl (S)-3-(4-bromo-5-cyano-1-(4-phenoxyphenyl)-1H-pyrrol-3-yl)pyrrolidine-1-carboxylate (9e). MS-ESI (m/z): 508 [M+1]⁺.

butyl (S)-4-(1-(tert-butoxycarbonyl)pyrrolidin-3-yl)-2-cyano-1-(4-phenoxyphenyl)-1H-pyrrole-3-carboxylate (9f)

A mixture of tert-butyl (S)-3-(4-bromo-5-cyano-1-(4-phenoxyphenyl)-1H-pyrrol-3-yl)pyrrolidine-1-carboxylate (9e)) (57 mg, 0.11 mmol), TEA (34 mg, 0.33 mmol) and Pd(dppf)$_2$Cl$_2$ (25 mg, 0.04 mmol) in n-BuOH (2.5 mL) was stirred at 115° C. for 7 h at the atmosphere of CO. The mixture was cooled to r.t. and concentrated. The residue was purified by column chromatography on silica gel eluting with PE/EtOAc (8:1) to give the title compound butyl (S)-4-(1-(tert-butoxycarbonyl)pyrrolidin-3-yl)-2-cyano-1-(4-phenoxyphenyl)-1H-pyrrole-3-carboxylate (9f). MS-ESI (m/z): 530 [M+1]⁺.

tert-butyl (S)-3-(7-amino-4-oxo-1-(4-phenoxyphenyl)-4,5-dihydro-1H-pyrrolo[2,3-d]pyridazin-3-yl)pyrrolidine-1-carboxylate (9g)

A mixture of butyl (S)-4-(1-(tert-butoxycarbonyl)pyrrolidin-3-yl)-2-cyano-1-(4-phenoxyphenyl)-1H-pyrrole-3-carboxylate (9f) (39 mg, 0.074 mmol) and hydrazine hydrate (0.3 mL) in EtOH (0.5 mL) was stirred at 90° C. for 12 h. The mixture was diluted with water (50 mL), and extracted with DCM (2×50 mL). The organic phase was washed sequentially with water (20 mL) and brine (20 mL), dried and concentrated. The residue was purified by column chromatography on silica gel eluting with PE/EtOAc (2:1) to give the title compound tert-butyl (S)-3-(7-amino-4-oxo-1-(4-phenoxyphenyl)-4,5-dihydro-1H-pyrrolo[2,3-d]pyridazin-3-yl)pyrrolidine-1-carboxylate (9g). MS-ESI (m/z): 488 [M+1]⁺.

(S)-7-amino-1-(4-phenoxyphenyl)-3-(pyrrolidin-3-yl)-1,5-dihydro-4H-pyrrolo[2,3-d]pyridazin-4-one (9h)

A mixture of tert-butyl (S)-3-(7-amino-4-oxo-1-(4-phenoxyphenyl)-4,5-dihydro-1H-pyrrolo[2,3-d]pyridazin-3-yl)pyrrolidine-1-carboxylate (9f) (40 mg, 0.081 mmol) in HCl/EA (9%, 4.0 mL) was stirred at 25° C. for 1 h. The mixture was concentrated to give the title compound (S)-7-amino-1-(4-phenoxyphenyl)-3-(pyrrolidin-3-yl)-1,5-dihydro-4H-pyrrolo[2,3-d]pyridazin-4-one (9h). MS-ESI (m/z): 388 [M+1]⁺.

(S)-3-(1-acryloylpyrrolidin-3-yl)-7-amino-1-(4-phenoxyphenyl)-1,5-dihydro-4H-pyrrolo[2,3-d]pyridazin-4-one (9)

A mixture of 7-amino-1-(4-phenoxyphenyl)-3-(pyrrolidin-3-yl)-1,5-dihydro-4H-pyrrolo[2,3-d]pyridazin-4-one (9h) (15 mg, 0.035 mmol), acrylic acid (1.9 mg, 0.035 mmol), EDCI (13 mg, 0.068 mmol) and TEA (13 μL, 0.088 mmol) in DCM (1 mL) was stirred at r.t. for 12 h. The mixture was diluted with water (10 mL), and extracted with EA (2×10 mL). The organic phase was washed sequentially with water (10 mL) and brine (10 mL), dried and evaporated. The residue was purified by column chromatography on silica gel eluting with DCM/MeOH (15:1) to give title compound (S)-3-(1-acryloylpyrrolidin-3-yl)-7-amino-1-(4-phenoxyphenyl)-1,5-dihydro-4H-pyrrolo[2,3-d]pyridazin-4-one (9). MS-ESI (m/z): 442 [M+1]⁺.

Example 10

(R)-3-(1-acryloylpyrrolidin-3-yl)-7-amino-1-(4-phenoxyphenyl)-1,5-dihydro-4H-pyrrolo[2,3-d]pyridazin-4-one (10)

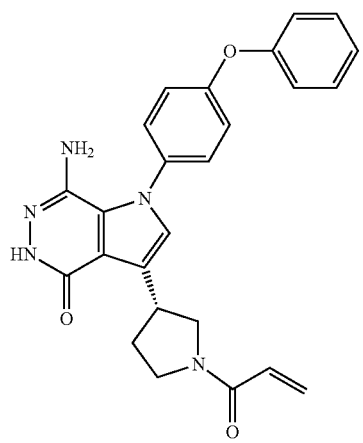

The title compound (R)-3-(1-acryloylpyrrolidin-3-yl)-7-amino-1-(4-phenoxyphenyl)-1,5-dihydro-4H-pyrrolo[2,3-d]pyridazin-4-one (10) was prepared according to the synthetic method of 9 by replacing tert-butyl (R)-3-(hydroxymethyl)pyrrolidine-1-carboxylate with tert-butyl (S)-3-(hydroxymethyl)pyrrolidine-1-carboxylate. MS-ESI (m/z): 442 [M+1]⁺.

Example 11

(S)-3-(1-acryloylpiperidin-3-yl)-7-amino-1-(4-phenoxyphenyl)-1,5-dihydro-4H-pyrrolo[2,3-d]pyridazin-4-one (11)

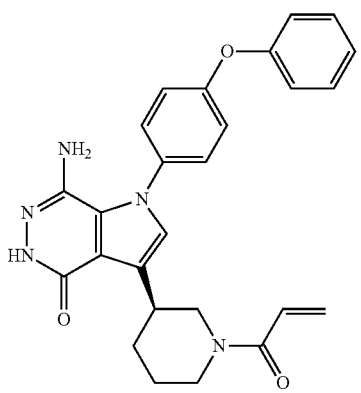

The title compound (S)-3-(1-acryloylpiperidin-3-yl)-7-amino-1-(4-phenoxyphenyl)-1,5-dihydro-4H-pyrrolo[2,3-d]pyridazin-4-one (11) was prepared according to the synthetic method of 9 by replacing tert-butyl (R)-3-(hydroxymethyl)pyrrolidine-1-carboxylate with tert-butyl (R)-3-(hydroxymethyl)piperidine-1-carboxylate. MS-ESI (m/z): 456 [M+1]⁺.

Example 12

(R)-3-(1-acryloylpiperidin-3-yl)-7-amino-1-(4-phenoxyphenyl)-1,5-dihydro-4H-pyrrolo[2,3-d]pyridazin-4-one (12)

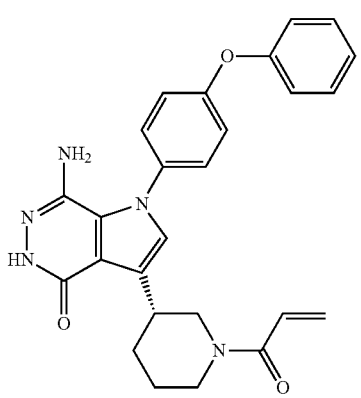

The title compound (R)-3-(1-acryloylpiperidin-3-yl)-7-amino-1-(4-phenoxyphenyl)-1,5-dihydro-4H-pyrrolo[2,3-d]pyridazin-4-one (12) was prepared according to the synthetic method of 11 by replacing tert-butyl (R)-3-(hydroxymethyl)piperidine-1-carboxylate with tert-butyl (S)-3-(hydroxymethyl)piperidine-1-carboxylate. MS-ESI (m/z): 456 [M+1]⁺.

Example 13

(R)-3-(1-acryloylpyrrolidin-3-yl)-7-amino-1-(4-phenoxyphenyl)-1,5-dihydro-4H-pyrazolo[3,4-d]pyridazin-4-one (13)

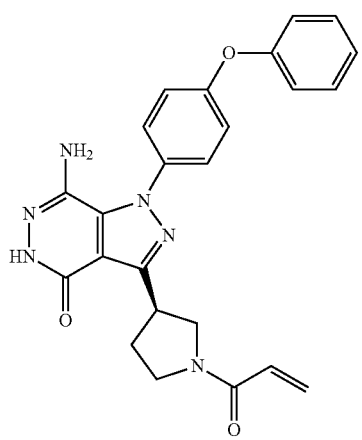

4-phenoxybenzenediazonium (13a)

To a mixture of 4-phenoxyaniline (1.0 g, 5.4 mmol) in 6 N HCl (40 mL) was added NaNO$_2$ (746 mg, 10.8 mmol) (in 2 mL H$_2$O). The mixture was stirred at −10° C. for 1 h to give title compound 4-phenoxybenzenediazonium (13a) as crude, which was used in the next step without further purification. MS-ESI (m/z): 197 [M]$^+$.

(R,Z)-tert-butyl 3-(cyano(2-(4-phenoxyphenyl)hydrazono)methyl)pyrrolidine-1-carboxylate (13b)

To a solution of tert-butyl (S)-3-((R)-1-cyano-2-oxoethyl)pyrrolidine-1-carboxylate (9b) (190 mg, 0.45 mmol) in EtOH (10 mL) was added 4-phenoxybenzenediazonium (13a) (100 mg, 0.54 mmol) (in 5 mL 6 N HCl) at 0° C. The pH was maintained at 6-7 by adding NaOAc in portions. The mixture was quenched by NH$_4$Cl (10 mL), and extracted with EA (2×50 mL). The organic phase was washed sequentially with water (50 mL) and brine (50 mL), dried and evaporated. The residue was purified by column chromatography on silica gel eluting with PE/EtOAc (10:1-5:1) to give the title compound (R)-tert-butyl 3-(4-amino-5-cyano-1-(4-phenoxyphenyl)-1H-pyrazol-3-yl)pyrrolidine-1-carboxylate(13b). MS-ESI (m/z): 407 [M+1]$^+$.

(R)-tert-butyl 3-(4-amino-5-cyano-1-(4-phenoxyphenyl)-1H-pyrazol-3-yl)pyrrolidine-1-carboxylate (13c)

To a solution of (R,Z)-tert-butyl 3-(cyano(2-(4-phenoxyphenyl)hydrazono)methyl)pyrrolidine-1-carboxylate (13b) (750 mg, 1.79 mmol) and 2-bromoacetonitrile (257 mg, 2.14 mmol) in t-BuOH (15 mL) was added t-BuONa (515 mg, 5.37 mmol). The mixture was stirred at r.t. overnight. The reaction was quenched by NH$_4$Cl (5 mL), and the mixture was extracted with EA (2×20 mL). The organic phase was washed sequentially with water (20 mL) and brine (20 mL), dried and evaporated to give the title compound (R)-tert-butyl 3-(4-amino-5-cyano-1-(4-phenoxyphenyl)-1H-pyrazol-3-yl)pyrrolidine-1-carboxylate (13c). MS-ESI (m/z): 446 [M+1]$^+$.

(R)-3-(1-acryloylpyrrolidin-3-yl)-7-amino-1-(4-phenoxyphenyl)-1H-pyrazolo[3,4-d]pyridazin-4(5H)-one (13)

The title compound (R)-3-(1-acryloylpyrrolidin-3-yl)-7-amino-1-(4-phenoxyphenyl)-1H-pyrazolo[3,4-d]pyridazin-4(5H)-one (13) was prepared according to the synthetic method of 9 by replacing tert-butyl (S)-3-(4-amino-5-cyano-1-(4-phenoxyphenyl)-1H-pyrrol-3-yl)pyrrolidine-1-carboxylate (9d) with (R)-tert-butyl 3-(4-amino-5-cyano-1-(4-phenoxyphenyl)-1H-pyrazol-3-yl)pyrrolidine-1-carboxylate (13c). MS-ESI (m/z): 443 [M+1]$^+$.

Example 14

(S)-3-(1-acryloylpyrrolidin-3-yl)-7-amino-1-(4-phenoxyphenyl)-1,5-dihydro-4H-pyrazolo[3,4-d]pyridazin-4-one (14)

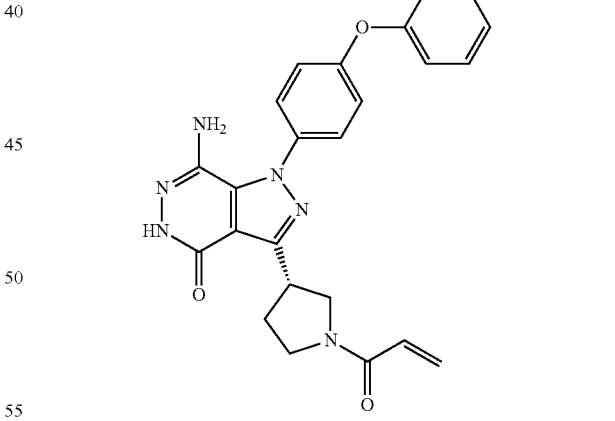

The title compound (S)-3-(1-acryloylpyrrolidin-3-yl)-7-amino-1-(4-phenoxyphenyl)-1,5-dihydro-4H-pyrazolo[3,4-d]pyridazin-4-one (14) was prepared according to the synthetic method of 13 by replacing tert-butyl (R)-3-(hydroxymethyl)pyrrolidine-1-carboxylate with tert-butyl (S)-3-(hydroxymethyl)pyrrolidine-1-carboxylate. MS-ESI (m/z): 443 [M+1]$^+$.

Example 15

(R)-3-(1-acryloylpiperidin-3-yl)-7-amino-1-(4-phenoxyphenyl)-1,5-dihydro-4H-pyrazolo[3,4-d]pyridazin-4-one (15)

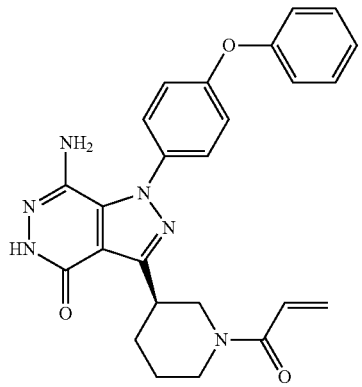

The title compound (R)-3-(1-acryloylpiperidin-3-yl)-7-amino-1-(4-phenoxyphenyl)-1,5-dihydro-4H-pyrazolo[3,4-d]pyridazin-4-one (15) was prepared according to the synthetic method of 13 by replacing tert-butyl (R)-3-(hydroxymethyl)pyrrolidine-1-carboxylate with tert-butyl (R)-3-(hydroxymethyl)piperidine-1-carboxylate. MS-ESI (m/z): 457 [M+1]+.

Example 16

(S)-3-(1-acryloylpiperidin-3-yl)-7-amino-1-(4-phenoxyphenyl)-1,5-dihydro-4H-pyrazolo[3,4-d]pyridazin-4-one (16)

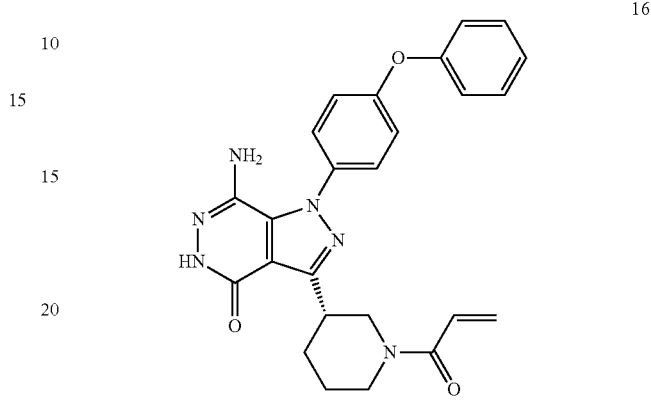

The title compound (S)-3-(1-acryloylpiperidin-3-yl)-7-amino-1-(4-phenoxyphenyl)-1,5-dihydro-4H-pyrazolo[3,4-d]pyridazin-4-one (16) was prepared according to the synthetic method of 15 by replacing tert-butyl (R)-3-(hydroxymethyl)piperidine-1-carboxylate with tert-butyl (S)-3-(hydroxymethyl)piperidine-1-carboxylate. MS-ESI (m/z): 457 [M+1]+.

Following essentially the same procedures described for Examples 9-16, Examples 17-117 listed in Table 1 were prepared from the appropriate starting materials which are commercially available or known in the literature. The structures and names of Examples 17-117 are given in Table 1.

TABLE 1

| EXAMPLE | STRUCTURE | NAME | DATA |
|---|---|---|---|
| 17 | 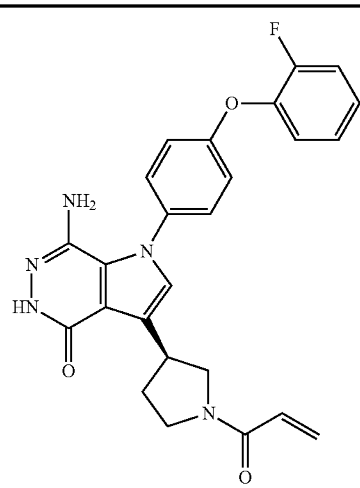 | (S)-3-(1-acryloylpyrrolidin-3-yl)-7-amino-1-(4-(2-fluorophenoxy)phenyl)-1,5-dihydro-4H-pyrrolo[2,3-d]pyridazin-4-one | MS-ESI (m/z): 460 [M + 1]+ |

TABLE 1-continued

| EXAMPLE | STRUCTURE | NAME | DATA |
| --- | --- | --- | --- |
| 18 | 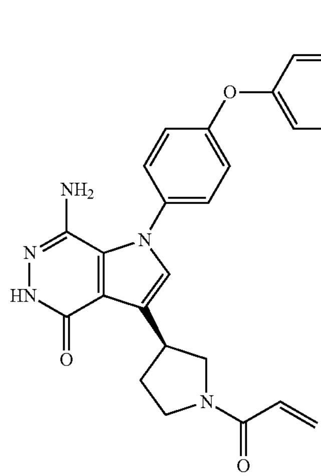 | (S)-3-(1-acryloylpyrrolidin-3-yl)-7-amino-1-(4-(3-fluorophenoxy)phenyl)-1,5-dihydro-4H-pyrrolo[2,3-d]pyridazin-4-one | MS-ESI (m/z): 460 [M + 1]$^+$ |
| 19 | 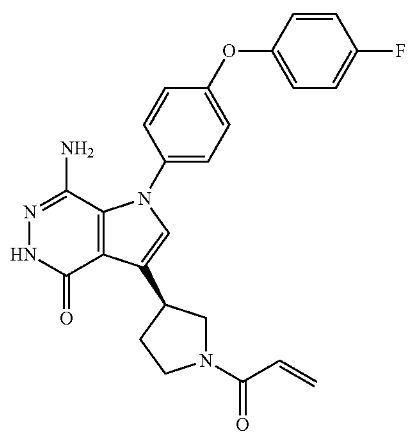 [SMILES: C=CC(=O)N1CC[C@@H](c2cn(-c3ccc(Oc4ccc(F)cc4)cc3)c3c(N)n[nH]c(=O)c23)C1] | (S)-3-(1-acryloylpyrrolidin-3-yl)-7-amino-1-(4-(4-fluorophenoxy)phenyl)-1,5-dihydro-4H-pyrrolo[2,3-d]pyridazin-4-one | MS-ESI (m/z): 460 [M + 1]$^+$ |
| 20 | 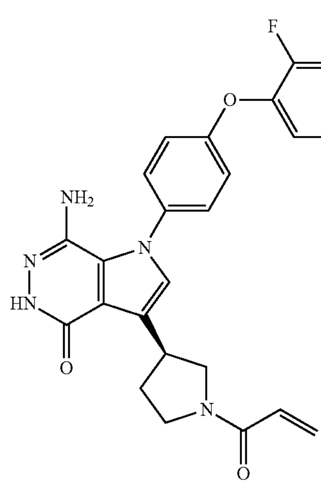 | (S)-3-(1-acryloylpyrrolidin-3-yl)-7-amino-1-(4-(2,3-difluorophenoxy)phenyl)-1,5-dihydro-4H-pyrrolo[2,3-d]pyridazin-4-one | MS-ESI (m/z): 478 [M + 1]$^+$ |

TABLE 1-continued

| EXAMPLE | STRUCTURE | NAME | DATA |
|---|---|---|---|
| 21 | 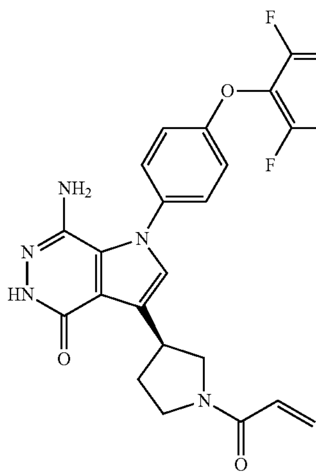 | (S)-1-acryloylpyrrolidin-3-yl)-7-amino-1-(4-(2,6-difluorophenoxy)phenyl)-1,5-dihydro-4H-pyrrolo[2,3-d]pyridazin-4-one | MS-ESI (m/z): 478 [M + 1]+ |
| 22 | 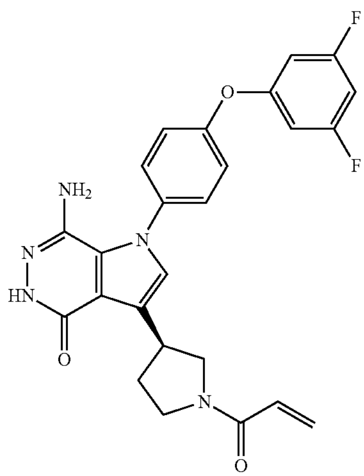 [SMILES: C=CC(=O)N1CC[C@@H](c2cn(-c3ccc(Oc4cc(F)cc(F)c4)cc3)c3c(N)n[nH]c(=O)c23)C1] | (S)-3-(1-acryloylpyrrolidin-3-yl)-7-amino-1-(4-(3,5-difluorophenoxy)phenyl)-1,5-dihydro-4H-pyrrolo[2,3-d]pyridazin-4-one | MS-ESI (m/z): 478 [M + 1]+ |
| 23 | 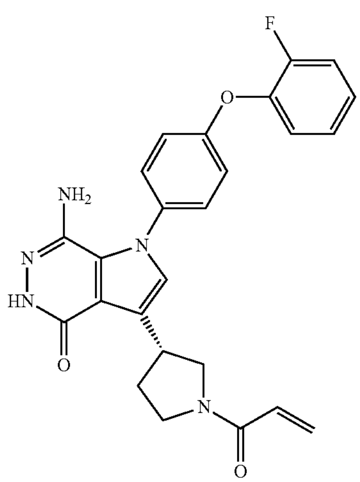 [SMILES: C=CC(=O)N1CC[C@H](c2cn(-c3ccc(Oc4ccccc4F)cc3)c3c(N)n[nH]c(=O)c23)C1] | (R)-3-(1-acryloylpyrrolidin-3-yl)-7-amino-1-(4-(2-fluorophenoxy)phenyl)-1,5-dihydro-4H-pyrrolo[2,3-d]pyridazin-4-one | MS-ESI (m/z): 460 [M + 1]+ |

TABLE 1-continued

| EXAMPLE | STRUCTURE | NAME | DATA |
|---|---|---|---|
| 24 | 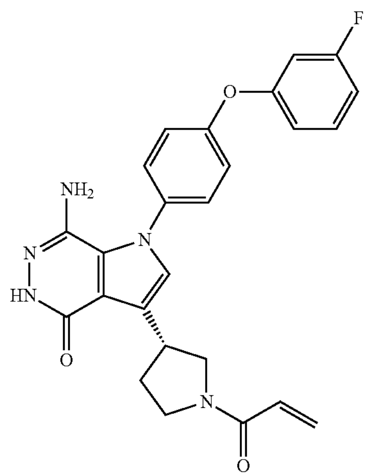 [SMILES: C=CC(=O)N1CC[C@H](c2cn(-c3ccc(Oc4cccc(F)c4)cc3)c3c(N)n[nH]c(=O)c23)C1] | (R)-3-(1-acryloylpyrrolidin-3-yl)-7-amino-1-(4-(3-fluorophenoxy)phenyl)-1,5-dihydro-4H-pyrrolo[2,3-d]pyridazin-4-one | MS-ESI (m/z): 460 [M + 1]+ |
| 25 | 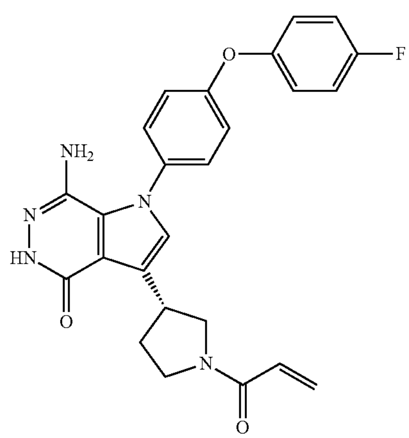 [SMILES: C=CC(=O)N1CC[C@H](c2cn(-c3ccc(Oc4ccc(F)cc4)cc3)c3c(N)n[nH]c(=O)c23)C1] | (R)-3-(1-acryloylpyrrolidin-3-yl)-7-amino-1-(4-(4-fluorophenoxy)phenyl)-1,5-dihydro-4H-pyrrolo[2,3-d]pyridazin-4-one | MS-ESI (m/z): 460 [M + 1]+ |
| 26 | 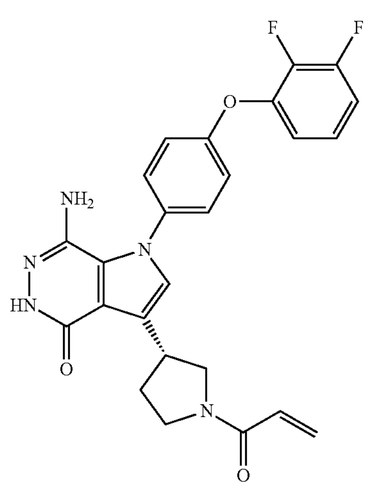 [SMILES: C=CC(=O)N1CC[C@H](c2cn(-c3ccc(Oc4cccc(F)c4F)cc3)c3c(N)n[nH]c(=O)c23)C1] | (R)-3-(1-acryloylpyrrolidin-3-yl)-7-amino-1-(4-(2,3-difluorophenoxy)phenyl)-1,5-dihydro-4H-pyrrolo[2,3-d]pyridazin-4-one | MS-ESI (m/z): 478 [M + 1]+ |

TABLE 1-continued

| EXAMPLE | STRUCTURE | NAME | DATA |
| --- | --- | --- | --- |
| 27 | 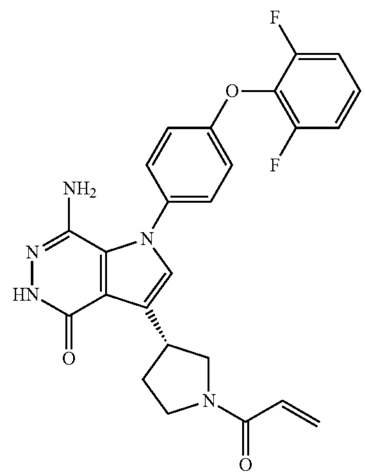 [SMILES: C=CC(=O)N1CC[C@H](c2cn(-c3ccc(Oc4c(F)cccc4F)cc3)c3c(N)n[nH]c(=O)c23)C1] | (R)-3-(1-acryloylpyrrolidin-3-yl)-7-amino-1-(4-(2,6-difluorophenoxy)phenyl)-1,5-dihydro-4H-pyrrolo[2,3-d]pyridazin-4-one | MS-ESI (m/z): 478 [M + 1]$^+$ |
| 28 | 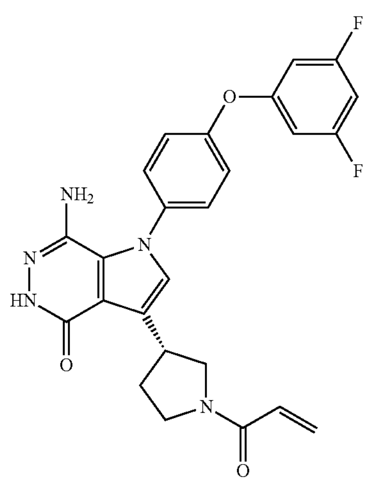 [SMILES: C=CC(=O)N1CC[C@H](c2cn(-c3ccc(Oc4cc(F)cc(F)c4)cc3)c3c(N)n[nH]c(=O)c23)C1] | (R)-3-(1-acryloylpyrrolidin-3-yl)-7-amino-1-(4-(3,5-difluorophenoxy)phenyl)-1,5-dihydro-4H-pyrrolo[2,3-d]pyridazin-4-one | MS-ESI (m/z): 478 [M + 1]$^+$ |
| 29 | 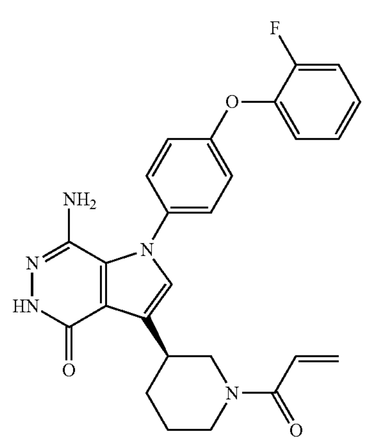 [SMILES: C=CC(=O)N1CCC[C@@H](c2cn(-c3ccc(Oc4ccccc4F)cc3)c3c(N)n[nH]c(=O)c23)C1] | (S)-3-(1-acryloylpiperidin-3-yl)-7-amino-1-(4-(2-fluorophenoxy)phenyl)-1,5-dihydro-4H-pyrrolo[2,3-d]pyridazin-4-one | MS-ESI (m/z): 474 [M + 1]$^+$ |

TABLE 1-continued

| EXAMPLE | STRUCTURE | NAME | DATA |
|---|---|---|---|
| 30 | 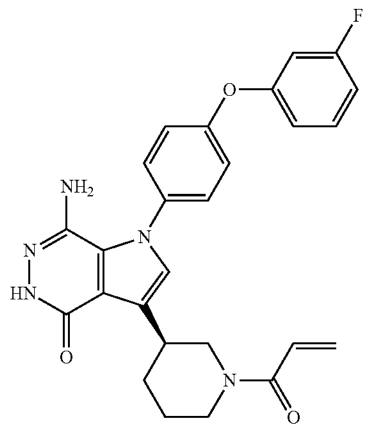 [SMILES: C=CC(=O)N1CCC[C@@H](c2cn(-c3ccc(Oc4cccc(F)c4)cc3)c3c(N)n[nH]c(=O)c23)C1] | (S)-3-(1-acryloylpiperidin-3-yl)-7-amino-1-(4-(3-fluorophenoxy)phenyl)-1,5-dihydro-4H-pyrrolo[2,3-d]pyridazin-4-one | MS-ESI (m/z): 474 [M + 1]+ |
| 31 | 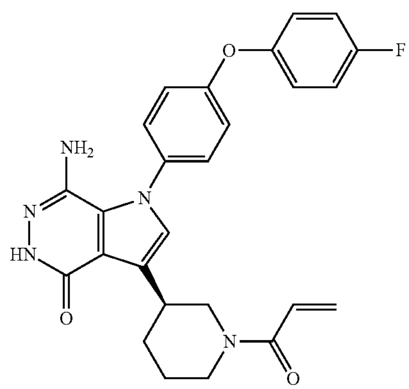 [SMILES: C=CC(=O)N1CCC[C@@H](c2cn(-c3ccc(Oc4ccc(F)cc4)cc3)c3c(N)n[nH]c(=O)c23)C1] | (S)-3-(1-acryloylpiperidin-3-yl)-7-amino-1-(4-(4-fluorophenoxy)phenyl)-1,5-dihydro-4H-pyrrolo[2,3-d]pyridazin-4-one | MS-ESI (m/z): 474 [M + 1]+ |
| 32 | 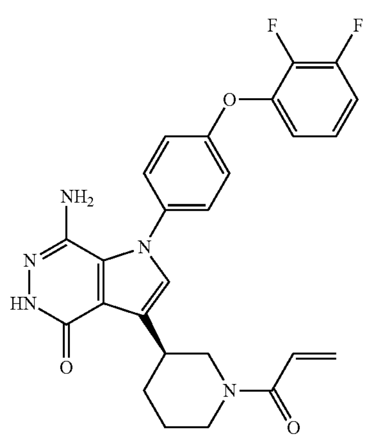 [SMILES: C=CC(=O)N1CCC[C@@H](c2cn(-c3ccc(Oc4cccc(F)c4F)cc3)c3c(N)n[nH]c(=O)c23)C1] | (S)-3-(1-acryloylpiperidin-3-yl)-7-amino-1-(4-(2,3-difluorophenoxy)phenyl)-1,5-dihydro-4H-pyrrolo[2,3-d]pyridazin-4-one | MS-ESI (m/z): [M + 1]+ |

TABLE 1-continued

| EXAMPLE | STRUCTURE | NAME | DATA |
|---|---|---|---|
| 33 | 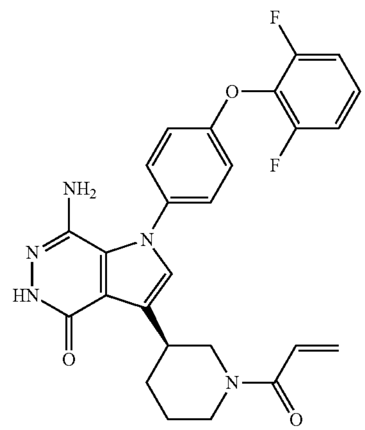 [SMILES: C=CC(=O)N1CCC[C@@H](c2cn(-c3ccc(Oc4c(F)cccc4F)cc3)c3c(N)n[nH]c(=O)c23)C1] | (S)-3-(1-acryloylpiperidin-3-yl)-7-amino-1-(4-(2,6-difluorophenoxy)phenyl)-1,5-dihydro-4H-pyrrolo[2,3-d]pyridazin-4-one | MS-ESI (m/z): 492 [M + 1]$^+$ |
| 34 | 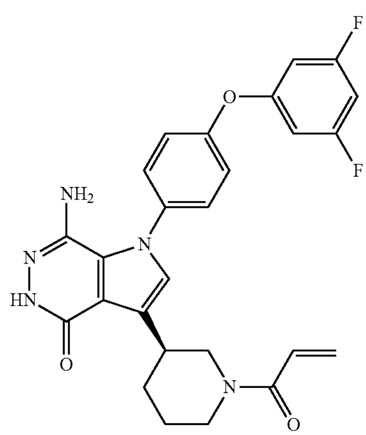 [SMILES: C=CC(=O)N1CCC[C@@H](c2cn(-c3ccc(Oc4cc(F)cc(F)c4)cc3)c3c(N)n[nH]c(=O)c23)C1] | (S)-3-(1-acryloylpiperidin-3-yl)-7-amino-1-(4-(3,5-difluorophenoxy)phenyl)-1,5-dihydro-4H-pyrrolo[2,3-d]pyridazin-4-one | MS-ESI (m/z): 492 [M + 1]$^+$ |
| 35 | 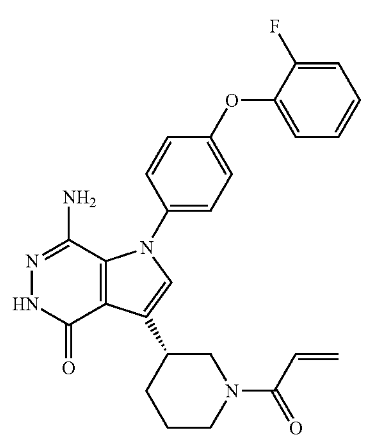 [SMILES: C=CC(=O)N1CCC[C@H](c2cn(-c3ccc(Oc4ccccc4F)cc3)c3c(N)n[nH]c(=O)c23)C1] | (R)-3-(1-acryloylpiperidin-3-yl)-7-amino-1-(4-(2-fluorophenoxy)phenyl)-1,5-dihydro-4H-pyrrolo[2,3-d]pyridazin-4-one | MS-ESI (m/z): 474 [M + 1]$^+$ |

TABLE 1-continued

| EXAMPLE | STRUCTURE | NAME | DATA |
|---------|-----------|------|------|
| 36 | 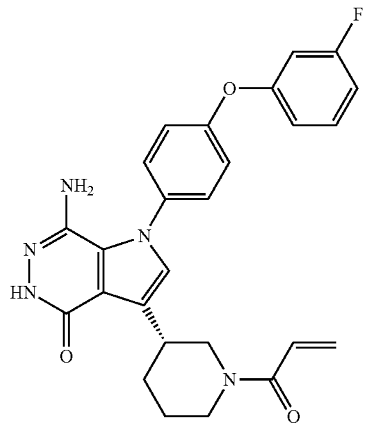 [SMILES: C=CC(=O)N1CCC[C@H](c2cn(-c3ccc(Oc4cccc(F)c4)cc3)c3c(N)n[nH]c(=O)c23)C1] | (R)-3-(1-acryloylpiperidin-3-yl)-7-amino-1-(4-(3-fluorophenoxy)phenyl)-1,5-dihydro-4H-pyrrolo[2,3-d]pyridazin-4-one | MS-ESI (m/z): 474 [M + 1]⁺ |
| 37 | 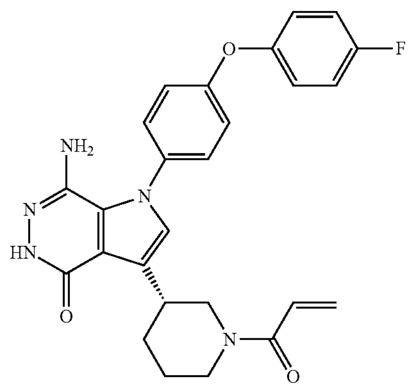 [SMILES: C=CC(=O)N1CCC[C@H](c2cn(-c3ccc(Oc4ccc(F)cc4)cc3)c3c(N)n[nH]c(=O)c23)C1] | (R)-3-(1-acryloylpiperidin-3-yl)-7-amino-1-(4-(4-fluorophenoxy)phenyl)-1,5-dihydro-4H-pyrrolo[2,3-d]pyridazin-4-one | MS-ESI (m/z): 474 [M + 1]⁺ |
| 38 | 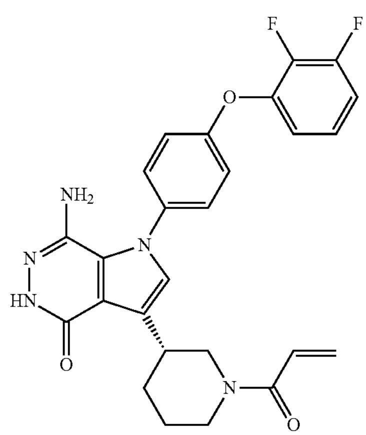 [SMILES: C=CC(=O)N1CCC[C@H](c2cn(-c3ccc(Oc4cccc(F)c4F)cc3)c3c(N)n[nH]c(=O)c23)C1] | (R)-3-(1-acryloylpiperidin-3-yl)-7-amino-1-(4-(2,3-difluorophenoxy)phenyl)-1,5-dihydro-4H-pyrrolo[2,3-d]pyridazin-4-one | MS-ESI (m/z): 492 [M + 1]⁺ |

TABLE 1-continued

| EXAMPLE | STRUCTURE | NAME | DATA |
|---|---|---|---|
| 39 | 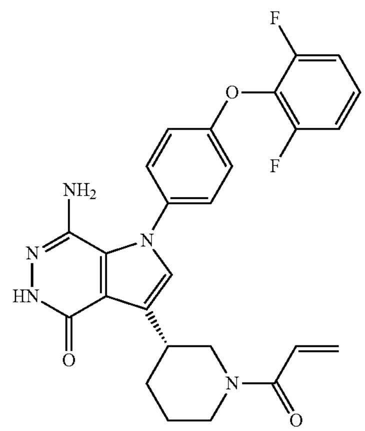 [SMILES: C=CC(=O)N1CCC[C@H](c2cn(-c3ccc(Oc4c(F)cccc4F)cc3)c3c(N)n[nH]c(=O)c23)C1] | (R)-3-(1-acryloylpiperidin-3-yl)-7-amino-1-(4-(2,6-difluorophenoxy)phenyl)-1,5-dihydro-4H-pyrrolo[2,3-d]pyridazin-4-one | MS-ESI (m/z): 492 [M + 1]+ |
| 40 | 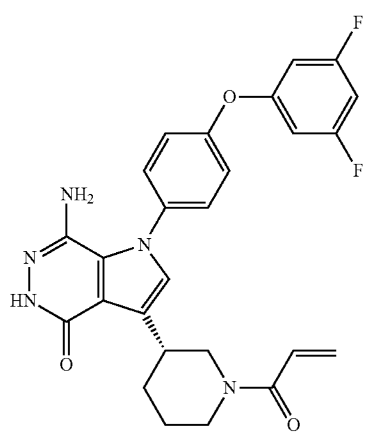 | (R)-3-(1-acryloylpiperidin-3-yl)-7-amino-1-(4-(3,5-difluorophenoxy)phenyl)-1,5-dihydro-4H-pyrrolo[2,3-d]pyridazin-4-one | MS-ESI (m/z): 492 [M + 1]+ |
| 41 | 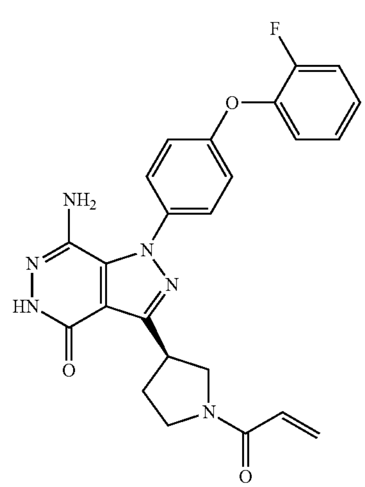 [SMILES: C=CC(=O)N1CC[C@@H](c2nn(-c3ccc(Oc4ccccc4F)cc3)c3c(N)n[nH]c(=O)c23)C1] | (R)-3-(1-acryloylpyrrolidin-3-yl)-7-amino-1-(4-(2-fluorophenoxy)phenyl)-1,5-dihydro-4H-pyrazolo[3,4-d]pyridazin-4-one | MS-ESI (m/z): 461 [M + 1]+ |

TABLE 1-continued

| EXAMPLE | STRUCTURE | NAME | DATA |
|---|---|---|---|
| 42 | 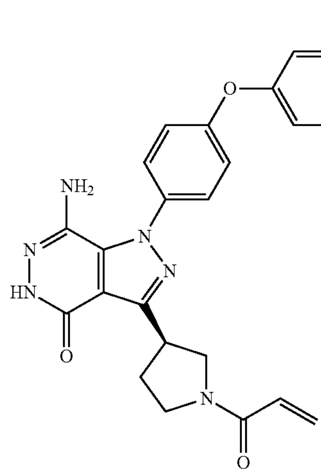 | (R)-3-(1-acryloylpyrrolidin-3-yl)-7-amino-1-(4-(3-fluorophenoxy)phenyl)-1,5-dihydro-4H-pyrazolo[3,4-d]pyridazin-4-one | MS-ESI (m/z): 461 [M + 1]⁺ |
| 43 | 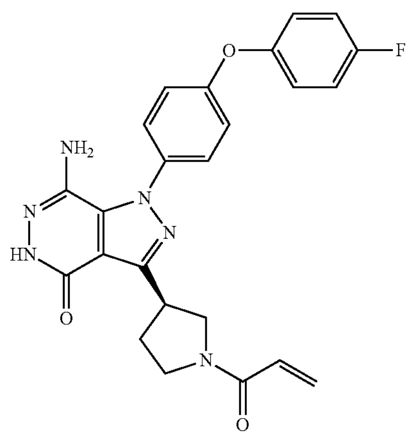 [SMILES: C=CC(=O)N1CC[C@@H](c2nn(-c3ccc(Oc4ccc(F)cc4)cc3)c3c(N)n[nH]c(=O)c23)C1] | (R)-3-(1-acryloylpyrrolidin-3-yl)-7-amino-1-(4-(4-fluorophenoxy)phenyl)-1,5-dihydro-4H-pyrazolo[3,4-d]pyridazin-4-one | MS-ESI (m/z): 461 [M + 1]⁺ |
| 44 | 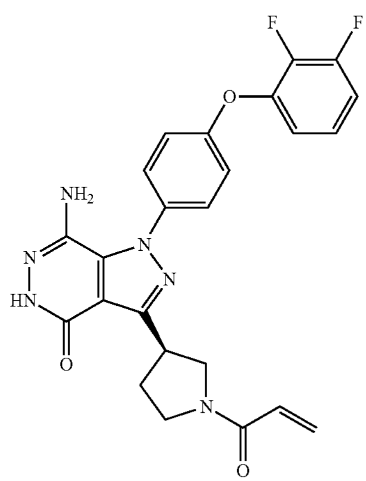 | (R)-3-(1-acryloylpyrrolidin-3-yl)-7-amino-1-(4-(2,3-difluorophenoxy)phenyl)-1,5-dihydro-4H-pyrazolo[3,4-d]pyridazin-4-one | MS-ESI (m/z): 479 [M + 1]⁺ |

TABLE 1-continued

| EXAMPLE | STRUCTURE | NAME | DATA |
| --- | --- | --- | --- |
| 45 | 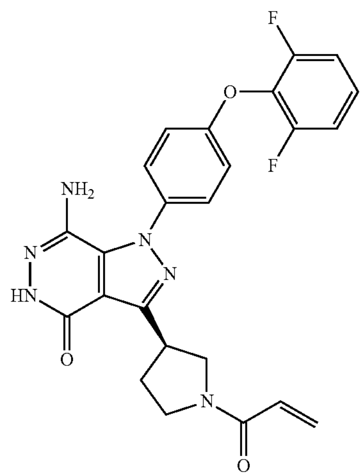 [SMILES: C=CC(=O)N1CC[C@@H](c2nn(-c3ccc(Oc4c(F)cccc4F)cc3)c3c(N)n[nH]c(=O)c23)C1] | (R)-3-(1-acryloylpyrrolidin-3-yl)-7-amino-1-(4-(2,6-difluorophenoxy)phenyl)-1,5-dihydro-4H-pyrazolo[3,4-d]pyridazin-4-one | MS-ESI (m/z): 479 [M + 1]+ |
| 46 | 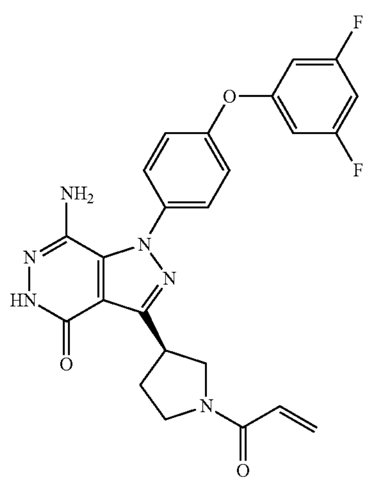 [SMILES: C=CC(=O)N1CC[C@@H](c2nn(-c3ccc(Oc4cc(F)cc(F)c4)cc3)c3c(N)n[nH]c(=O)c23)C1] | (R)-3-(1-acryloylpyrrolidin-3-yl)-7-amino-1-(4-(3,5-difluorophenoxy)phenyl)-1,5-dihydro-4H-pyrazolo[3,4-d]pyridazin-4-one | MS-ESI (m/z): 479 [M + 1]+ |
| 47 | 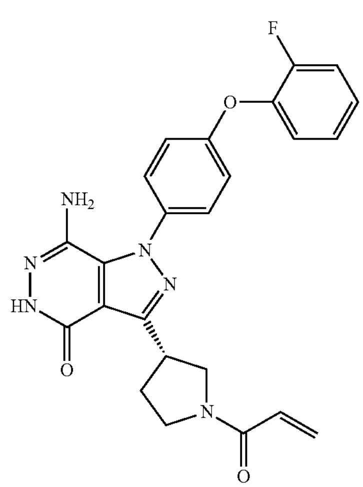 [SMILES: C=CC(=O)N1CC[C@H](c2nn(-c3ccc(Oc4ccccc4F)cc3)c3c(N)n[nH]c(=O)c23)C1] | (S)-3-(1-acryloylpyrrolidin-3-yl)-7-amino-1-(4-(2-fluorophenoxy)phenyl)-1,5-dihydro-4H-pyrazolo[3,4-d]pyridazin-4-one | MS-ESI (m/z): 461 [M + 1]+ |

TABLE 1-continued

| EXAMPLE | STRUCTURE | NAME | DATA |
| --- | --- | --- | --- |
| 48 | 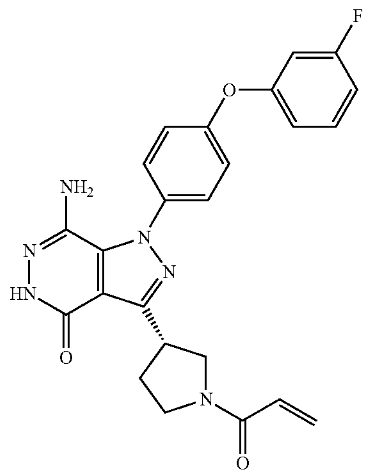 [SMILES: C=CC(=O)N1CC[C@H](c2nn(-c3ccc(Oc4cccc(F)c4)cc3)c3c(N)n[nH]c(=O)c23)C1] | (S)-3-(1-acryloylpyrrolidin-3-yl)-7-amino-1-(4-(3-fluorophenoxy)phenyl)-1,5-dihydro-4H-pyrazolo[3,4-d]pyridazin-4-one | MS-ESI (m/z): 461 [M + 1]$^+$ |
| 49 | 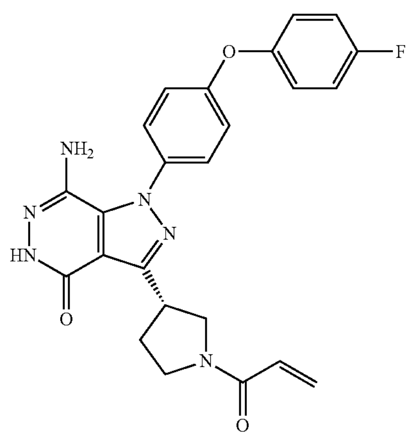 [SMILES: C=CC(=O)N1CC[C@H](c2nn(-c3ccc(Oc4ccc(F)cc4)cc3)c3c(N)n[nH]c(=O)c23)C1] | (S)-3-(1-acryloylpyrrolidin-3-yl)-7-amino-1-(4-(4-fluorophenoxy)phenyl)-1,5-dihydro-4H-pyrazolo[3,4-d]pyridazin-4-one | MS-ESI (m/z): 461 [M + 1]$^+$ |
| 50 | 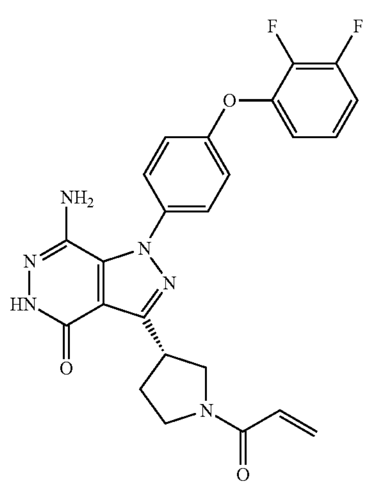 | (S)-3-(1-acryloylpyrrolidin-3-yl)-7-amino-1-(4-(2,3-difluorophenoxy)phenyl)-1,5-dihydro-4H-pyrazolo[3,4-d]pyridazin-4-one | MS-ESI (m/z): 479 [M + 1]$^+$ |

TABLE 1-continued

| EXAMPLE | STRUCTURE | NAME | DATA |
|---|---|---|---|
| 51 | 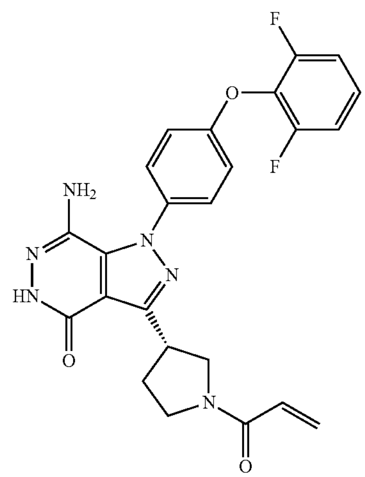 [SMILES: C=CC(=O)N1CC[C@H](c2nn(-c3ccc(Oc4c(F)cccc4F)cc3)c3c(N)n[nH]c(=O)c23)C1] | (S)-3-(1-acryloylpyrrolidin-3-yl)-7-amino-1-(4-(2,6-difluorophenoxy)phenyl)-1,5-dihydro-4H-pyrazolo[3,4-d]pyridazin-4-one | MS-ESI (m/z): 479 [M + 1]⁺ |
| 52 | 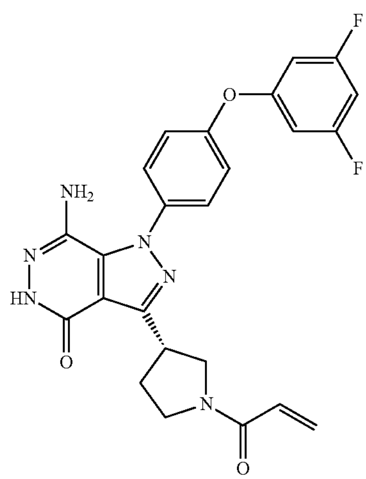 [SMILES: C=CC(=O)N1CC[C@H](c2nn(-c3ccc(Oc4cc(F)cc(F)c4)cc3)c3c(N)n[nH]c(=O)c23)C1] | (S)-3-(1-acryloylpyrrolidin-3-yl)-7-amino-1-(4-(3,5-difluorophenoxy)phenyl)-1,5-dihydro-4H-pyrazolo[3,4-d]pyridazin-4-one | MS-ESI (m/z): 479 [M + 1]⁺ |
| 53 | 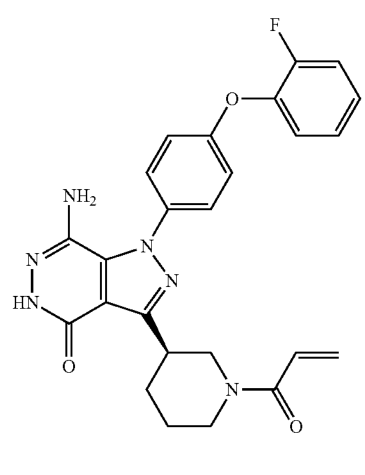 [SMILES: C=CC(=O)N1CCC[C@@H](c2nn(-c3ccc(Oc4ccccc4F)cc3)c3c(N)n[nH]c(=O)c23)C1] | (R)-3-(1-acryloylpiperidin-3-yl)-7-amino-1-(4-(2-fluorophenoxy)phenyl)-1,5-dihydro-4H-pyrazolo[3,4-d]pyridazin-4-one | MS-ESI (m/z): 475 [M + 1]⁺ |

TABLE 1-continued

| EXAMPLE | STRUCTURE | NAME | DATA |
| --- | --- | --- | --- |
| 54 | 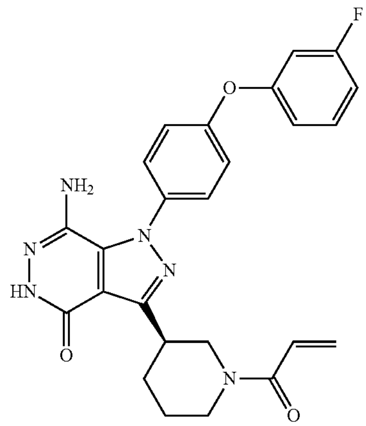 [SMILES: C=CC(=O)N1CCC[C@@H](c2nn(-c3ccc(Oc4cccc(F)c4)cc3)c3c(N)n[nH]c(=O)c23)C1] | (R)-3-(1-acryloylpiperidin-3-yl)-7-amino-1-(4-(3-fluorophenoxy)phenyl)-1,5-dihydro-4H-pyrazolo[3,4-d]pyridazin-4-one | MS-ESI (m/z): 475 [M + 1]$^+$ |
| 55 | 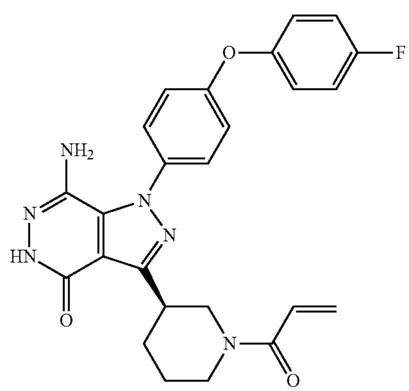 [SMILES: C=CC(=O)N1CCC[C@@H](c2nn(-c3ccc(Oc4ccc(F)cc4)cc3)c3c(N)n[nH]c(=O)c23)C1] | (R)-3-(1-acryloylpiperidin-3-yl)-7-amino-1-(4-(4-fluorophenoxy)phenyl)-1,5-dihydro-4H-pyrazolo[3,4-d]pyridazin-4-one | MS-ESI (m/z): 475 [M + 1]$^+$ |
| 56 | 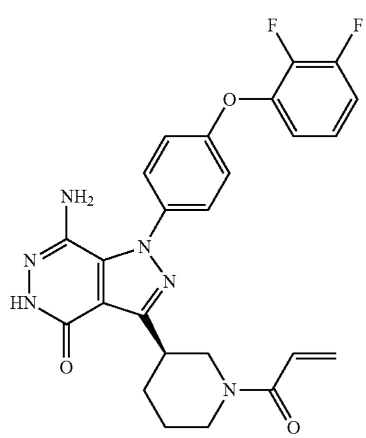 [SMILES: C=CC(=O)N1CCC[C@@H](c2nn(-c3ccc(Oc4cccc(F)c4F)cc3)c3c(N)n[nH]c(=O)c23)C1] | (R)-3-(1-acryloylpiperidin-3-yl)-7-amino-1-(4-(2,3-difluorophenoxy)phenyl)-1,5-dihydro-4H-pyrazolo[3,4-d]pyridazin-4-one | MS-ESI (m/z): 493 [M + 1]$^+$ |

TABLE 1-continued
| EXAMPLE | STRUCTURE | NAME | DATA |
|---|---|---|---|
| 57 | 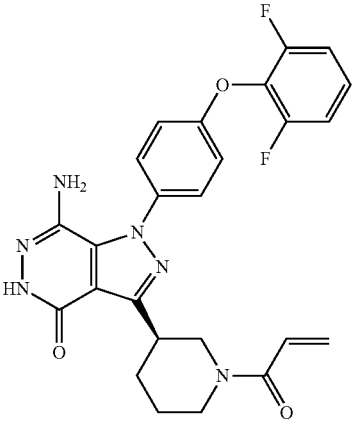 [SMILES: C=CC(=O)N1CCC[C@@H](c2nn(-c3ccc(Oc4c(F)cccc4F)cc3)c3c(N)n[nH]c(=O)c23)C1] | (R)-3-(1-acryloylpiperidin-3-yl)-7-amino-1-(4-(2,6-difluorophenoxy)phenyl)-1,5-dihydro-4H-pyrazolo[3,4-d]pyridazin-4-one | MS-ESI (m/z): 493 [M + 1]+ |
| 58 | 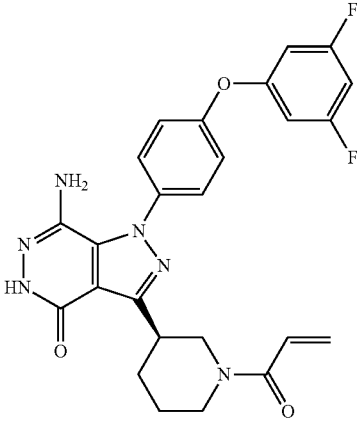 [SMILES: C=CC(=O)N1CCC[C@@H](c2nn(-c3ccc(Oc4cc(F)cc(F)c4)cc3)c3c(N)n[nH]c(=O)c23)C1] | (R)-3-(1-acryloylpiperidin-3-yl)-7-amino-1-(4-(3,5-difluorophenoxy)phenyl)-1,5-dihydro-4H-pyrazolo[3,4-d]pyridazin-4-one | MS-ESI (m/z): 493 [M + 1]+ |
| 59 | 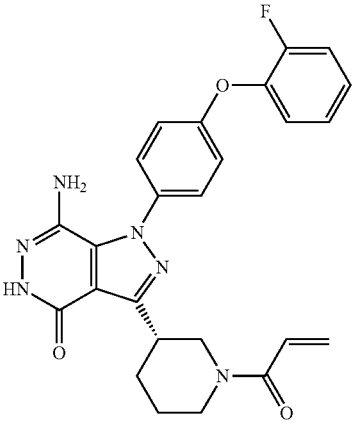 [SMILES: C=CC(=O)N1CCC[C@H](c2nn(-c3ccc(Oc4ccccc4F)cc3)c3c(N)n[nH]c(=O)c23)C1] | (S)-3-(1-acryloylpiperidin-3-yl)-7-amino-1-(4-(2-fluorophenoxy)phenyl)-1,5-dihydro-4H-pyrazolo[3,4-d]pyridazin-4-one | MS-ESI (m/z): 475 [M + 1]+ |

TABLE 1-continued

| EXAMPLE | STRUCTURE | NAME | DATA |
|---------|-----------|------|------|
| 60 | 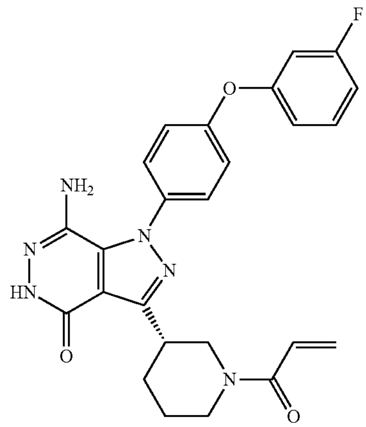 [SMILES: C=CC(=O)N1CCC[C@H](c2nn(-c3ccc(Oc4cccc(F)c4)cc3)c3c(N)n[nH]c(=O)c23)C1] | (S)-3-(1-acryloylpiperidin-3-yl)-7-amino-1-(4-(3-fluorophenoxy)phenyl)-1,5-dihydro-4H-pyrazolo[3,4-d]pyridazin-4-one | MS-ESI (m/z): 475 [M + 1]$^+$ |
| 61 | 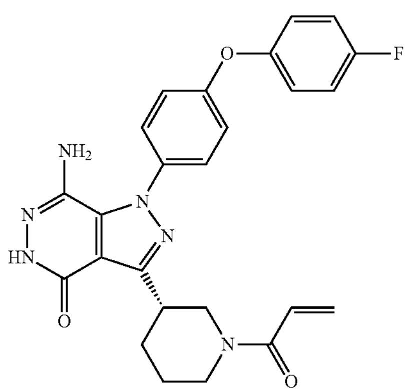 [SMILES: C=CC(=O)N1CCC[C@H](c2nn(-c3ccc(Oc4ccc(F)cc4)cc3)c3c(N)n[nH]c(=O)c23)C1] | (S)-3-(1-acryloylpiperidin-3-yl)-7-amino-1-(4-(4-fluorophenoxy)phenyl)-1,5-dihydro-4H-pyrazolo[3,4-d]pyridazin-4-one | MS-ESI (m/z): 475 [M + 1]$^+$ |
| 62 | 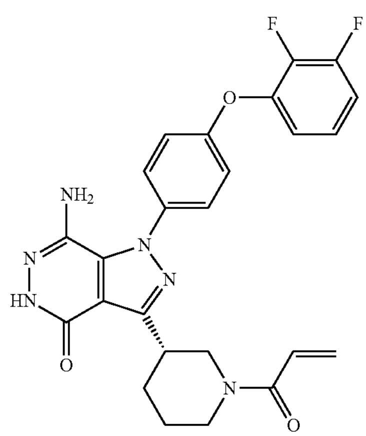 [SMILES: C=CC(=O)N1CCC[C@H](c2nn(-c3ccc(Oc4cccc(F)c4F)cc3)c3c(N)n[nH]c(=O)c23)C1] | (S)-3-(1-acryloylpiperidin-3-yl)-7-amino-1-(4-(2,3-difluorophenoxy)phenyl)-1,5-dihydro-4H-pyrazolo[3,4-d]pyridazin-4-one | MS-ESI (m/z): 493 [M + 1]$^+$ |

TABLE 1-continued

| EXAMPLE | STRUCTURE | NAME | DATA |
|---|---|---|---|
| 63 | 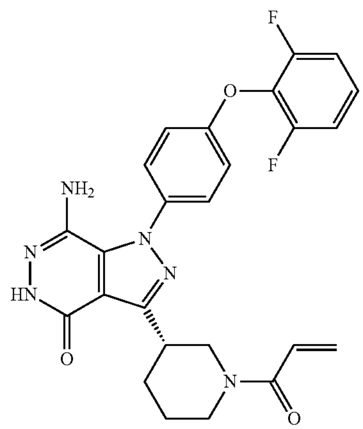 [SMILES: C=CC(=O)N1CCC[C@H](c2nn(-c3ccc(Oc4c(F)cccc4F)cc3)c3c(N)n[nH]c(=O)c23)C1] | (S)-3-(1-acryloylpiperidin-3-yl)-7-amino-1-(4-(2,6-difluorophenoxy)phenyl)-1,5-dihydro-4H-pyrazolo[3,4-d]pyridazin-4-one | MS-ESI (m/z): 493 [M + 1]+ |
| 64 | 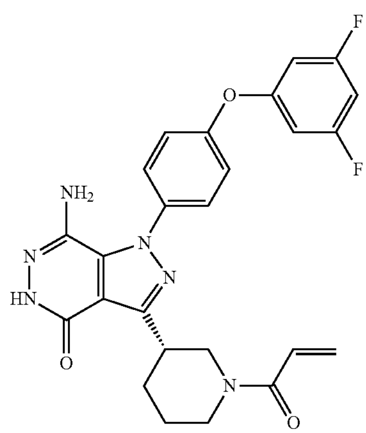 [SMILES: C=CC(=O)N1CCC[C@H](c2nn(-c3ccc(Oc4cc(F)cc(F)c4)cc3)c3c(N)n[nH]c(=O)c23)C1] | (S)-3-(1-acryloylpiperidin-3-yl)-7-amino-1-(4-(3,5-difluorophenoxy)phenyl)-1,5-dihydro-4H-pyrazolo[3,4-d]pyridazin-4-one | MS-ESI (m/z): 493 [M + 1]+ |
| 65 | 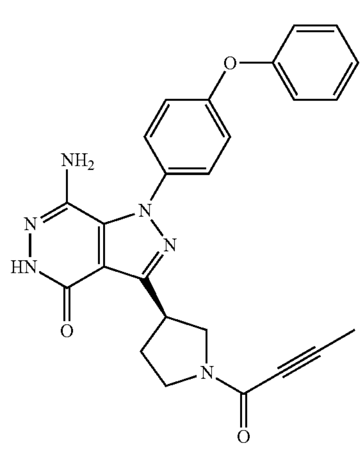 [SMILES: CC#CC(=O)N1CC[C@@H](c2nn(-c3ccc(Oc4ccccc4)cc3)c3c(N)n[nH]c(=O)c23)C1] | (R)-7-amino-3-(1-(but-2-ynoyl)pyrrolidin-3-yl)-1-(4-phenoxyphenyl)-1,5-dihydro-4H-pyrazolo[3,4-d]pyridazin-4-one | MS-ESI (m/z): 455 [M + 1]+ |

TABLE 1-continued

| EXAMPLE | STRUCTURE | NAME | DATA |
| --- | --- | --- | --- |
| 66 | 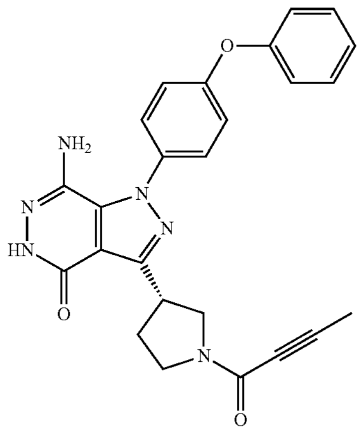 [SMILES: CC#CC(=O)N1CC[C@H](c2nn(-c3ccc(Oc4ccccc4)cc3)c3c(N)n[nH]c(=O)c23)C1] | (S)-7-amino-3-(1-(but-2-ynoyl)pyrrolidin-3-yl)-1-(4-phenoxyphenyl)-1,5-dihydro-4H-pyrazolo[3,4-d]pyridazin-4-one | MS-ESI (m/z): 455 [M + 1]$^+$ |
| 67 | 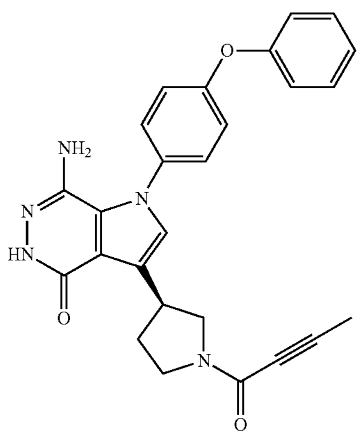 [SMILES: CC#CC(=O)N1CC[C@@H](c2cn(-c3ccc(Oc4ccccc4)cc3)c3c(N)n[nH]c(=O)c23)C1] | (S)-7-amino-3-(1-(but-2-ynoyl)pyrrolidin-3-yl)-1-(4-phenoxyphenyl)-1,5-dihydro-4H-pyrrolo[2,3-d]pyridazin-4-one | MS-ESI (m/z): 454 [M + 1]$^+$ |
| 68 | 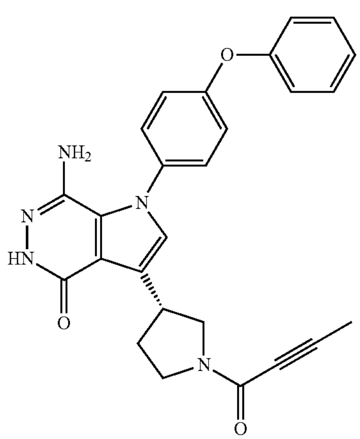 | (R)-7-amino-3-(1-(but-2-ynoyl)pyrrolidin-3-yl)-1-(4-phenoxyphenyl)-1,5-dihydro-4H-pyrrolo[2,3-d]pyridazin-4-one | MS-ESI (m/z): 454 [M + 1]$^+$ |

TABLE 1-continued

| EXAMPLE | STRUCTURE | NAME | DATA |
|---|---|---|---|
| 69 | 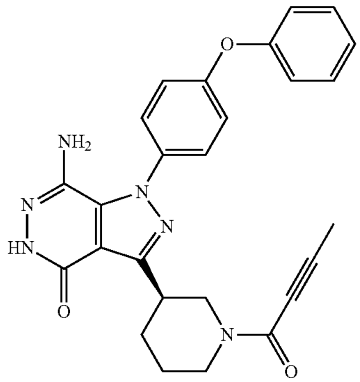 [SMILES: CC#CC(=O)N1CCC[C@@H](c2nn(-c3ccc(Oc4ccccc4)cc3)c3c(N)n[nH]c(=O)c23)C1] | (R)-7-amino-3-(1-(but-2-ynoyl)piperidin-3-yl)-1-(4-phenoxyphenyl)-1,5-dihydro-4H-pyrazolo[3,4-d]pyridazin-4-one | MS-ESI (m/z): 469 [M + 1]+ |
| 70 | 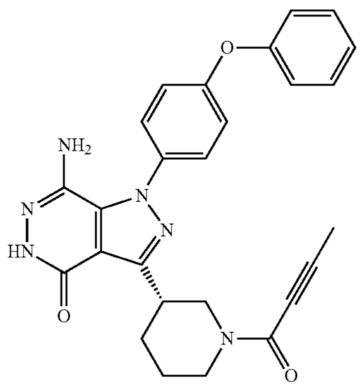 [SMILES: CC#CC(=O)N1CCC[C@H](c2nn(-c3ccc(Oc4ccccc4)cc3)c3c(N)n[nH]c(=O)c23)C1] | (S)-7-amino-3-(1-(but-2-ynoyl)piperidin-3-yl)-1-(4-phenoxyphenyl)-1,5-dihydro-4H-pyrazolo[3,4-d]pyridazin-4-one | MS-ESI (m/z): 469 [M + 1]+ |
| 71 | 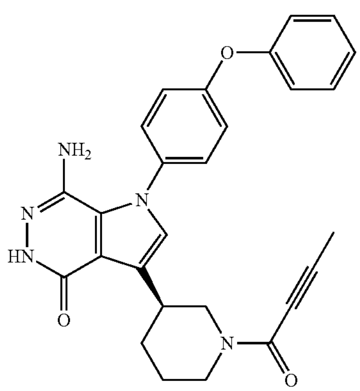 [SMILES: CC#CC(=O)N1CCC[C@@H](c2cn(-c3ccc(Oc4ccccc4)cc3)c3c(N)n[nH]c(=O)c23)C1] | (S)-7-amino-3-(1-(but-2-ynoyl)piperidin-3-yl)-1-(4-phenoxyphenyl)-1,5-dihydro-4H-pyrrolo[2,3-d]pyridazin-4-one | MS-ESI (m/z): 468 [M + 1]+ |
| 72 | 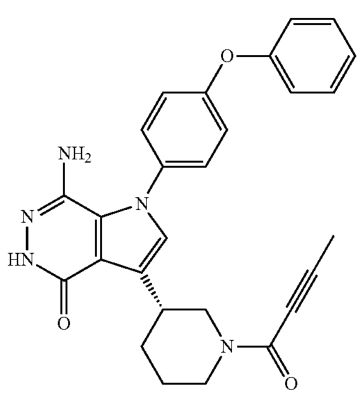 [SMILES: CC#CC(=O)N1CCC[C@H](c2cn(-c3ccc(Oc4ccccc4)cc3)c3c(N)n[nH]c(=O)c23)C1] | (R)-7-amino-3-(1-(but-2-ynoyl)piperidin-3-yl)-1-(4-phenoxyphenyl)-1,5-dihydro-4H-pyrrolo[2,3-d]pyridazin-4-one | MS-ESI (m/z): 468 [M + 1]+ |

TABLE 1-continued

| EXAMPLE | STRUCTURE | NAME | DATA |
|---|---|---|---|
| 73 | 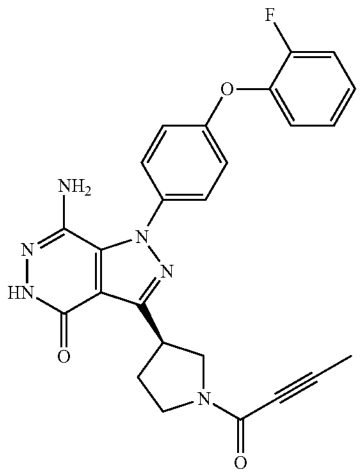 [SMILES: CC#CC(=O)N1CC[C@@H](c2nn(-c3ccc(Oc4ccccc4F)cc3)c3c(N)n[nH]c(=O)c23)C1] | (R)-7-amino-3-(1-(but-2-ynoyl)pyrrolidin-3-yl)-1-(4-(2-fluorophenoxy)phenyl)-1,5-dihydro-4H-pyrazolo[3,4-d]pyridazin-4-one | MS-ESI (m/z): 473 [M + 1]⁺ |
| 74 | 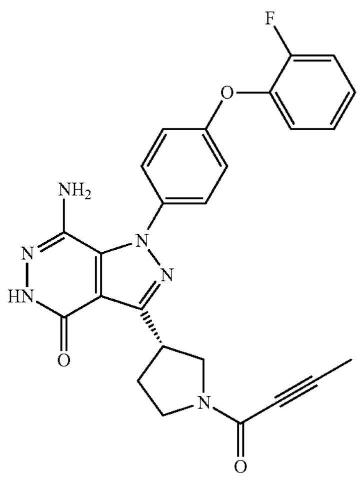 [SMILES: CC#CC(=O)N1CC[C@H](c2nn(-c3ccc(Oc4ccccc4F)cc3)c3c(N)n[nH]c(=O)c23)C1] | (S)-7-amino-3-(1-(but-2-ynoyl)pyrrolidin-3-yl)-1-(4-(2-fluorophenoxy)phenyl)-1,5-dihydro-4H-pyrazolo[3,4-d]pyridazin-4-one | MS-ESI (m/z): 473 [M + 1]⁺ |
| 75 | 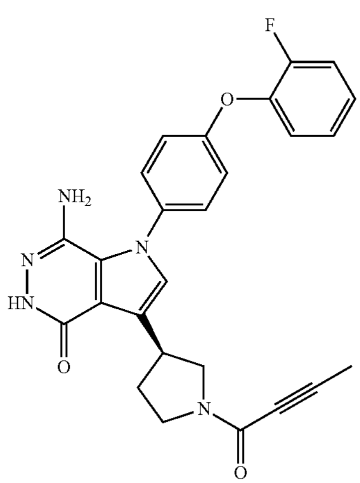 [SMILES: CC#CC(=O)N1CC[C@@H](c2cn(-c3ccc(Oc4ccccc4F)cc3)c3c(N)n[nH]c(=O)c23)C1] | (S)-7-amino-3-(1-(but-2-ynoyl)pyrrolidin-3-yl)-1-(4-(2-fluorophenoxy)phenyl)-1,5-dihydro-4H-pyrrolo[2,3-d]pyridazin-4-one | MS-ESI (m/z): 472 [M + 1]⁺ |

TABLE 1-continued

| EXAMPLE | NAME | DATA |
|---|---|---|
| 76 | (R)-7-amino-3-(1-(but-2-ynoyl)pyrrolidin-3-yl)-1-(4-(2-fluorophenoxy)phenyl)-1,5-dihydro-4H-pyrrolo[2,3-d]pyridazin-4-one | MS-ESI (m/z): 472 [M + 1]+ |
| 77 | (R)-7-amino-3-(1-(but-2-ynoyl)piperidin-3-yl)-1-(4-(2-fluorophenoxy)phenyl)-1,5-dihydro-4H-pyrazolo[3,4-d]pyridazin-4-one | MS-ESI (m/z): 487 [M + 1]+ |
| 78 | (S)-7-amino-3-(1-(but-2-ynoyl)piperidin-3-yl)-1-(4-(2-fluorophenoxy)phenyl)-1,5-dihydro-4H-pyrazolo[3,4-d]pyridazin-4-one | MS-ESI (m/z): 487 [M + 1]+ |

TABLE 1-continued

| EXAMPLE | STRUCTURE | NAME | DATA |
|---|---|---|---|
| 79 | 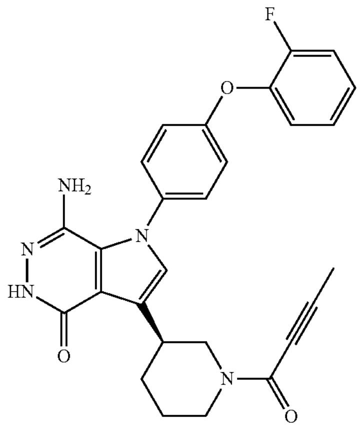 [SMILES: CC#CC(=O)N1CCC[C@@H](c2nn(-c3ccc(Oc4ccccc4F)cc3)c3c(N)n[nH]c(=O)c23)C1] | (S)-7-amino-3-(1-(but-2-ynoyl)piperidin-3-yl)-1-(4-(2-fluorophenoxy)phenyl)-1,5-dihydro-4H-pyrrolo[2,3-d]pyridazin-4-one | MS-ESI (m/z): 486 [M + 1]⁺ |
| 80 | 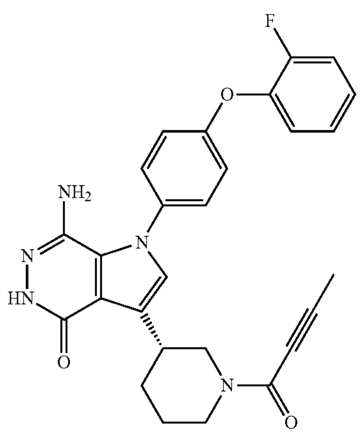 [SMILES: CC#CC(=O)N1CCC[C@H](c2cn(-c3ccc(Oc4ccccc4F)cc3)c3c(N)n[nH]c(=O)c23)C1] | (R)-7-amino-3-(1-(but-2-ynoyl)piperidin-3-yl)-1-(4-(2-fluorophenoxy)phenyl)-1,5-dihydro-4H-pyrrolo[2,3-d]pyridazin-4-one | MS-ESI (m/z): 486 [M + 1]⁺ |
| 81 | 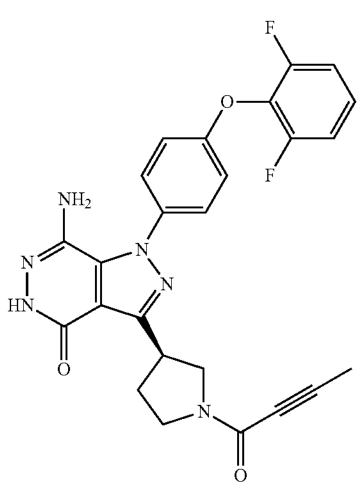 [SMILES: CC#CC(=O)N1CC[C@@H](c2nn(-c3ccc(Oc4c(F)cccc4F)cc3)c3c(N)n[nH]c(=O)c23)C1] | (R)-7-amino-3-(1-(but-2-ynoyl)pyrrolidin-3-yl)-1-(4-(2,6-difluorophenoxy)phenyl)-1,5-dihydro-4H-pyrazolo[3,4-d]pyridazin-4-one | MS-ESI (m/z): 491 [M + 1]⁺ |

TABLE 1-continued

| EXAMPLE | STRUCTURE | NAME | DATA |
|---|---|---|---|
| 82 | 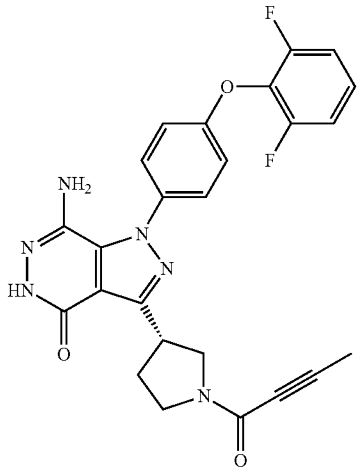 [SMILES: CC#CC(=O)N1CC[C@H](c2nn(-c3ccc(Oc4c(F)cccc4F)cc3)c3c(N)n[nH]c(=O)c23)C1] | (S)-7-amino-3-(1-(but-2-ynoyl)pyrrolidin-3-yl)-1-(4-(2,6-difluorophenoxy)phenyl)-1,5-dihydro-4H-pyrazolo[3,4-d]pyridazin-4-one | MS-ESI (m/z): 491 [M + 1]+ |
| 83 | 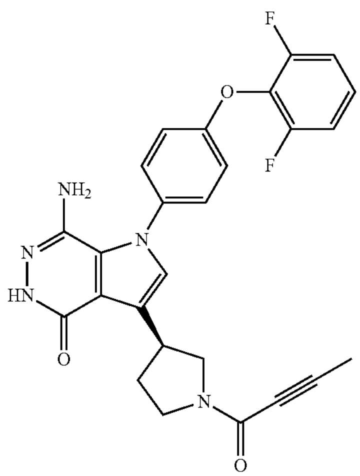 [SMILES: CC#CC(=O)N1CC[C@@H](c2cn(-c3ccc(Oc4c(F)cccc4F)cc3)c3c(N)n[nH]c(=O)c23)C1] | (S)-7-amino-3-(1-(but-2-ynoyl)pyrrolidin-3-yl)-1-(4-(2,6-difluorophenoxy)phenyl)-1,5-dihydro-4H-pyrrolo[2,3-d]pyridazin-4-one | MS-ESI (m/z): 490 [M + 1]+ |
| 84 | 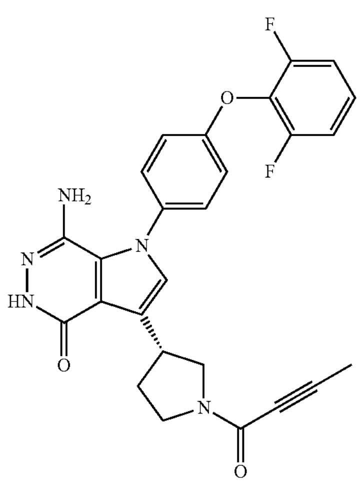 [SMILES: CC#CC(=O)N1CC[C@H](c2cn(-c3ccc(Oc4c(F)cccc4F)cc3)c3c(N)n[nH]c(=O)c23)C1] | (R)-7-amino-3-(1-(but-2-ynoyl)pyrrolidin-3-yl)-1-(4-(2,6-difluorophenoxy)phenyl)-1,5-dihydro-4H-pyrrolo[2,3-d]pyridazin-4-one | MS-ESI (m/z): 490 [M + 1]+ |

TABLE 1-continued

| EXAMPLE | STRUCTURE | NAME | DATA |
|---|---|---|---|
| 85 | 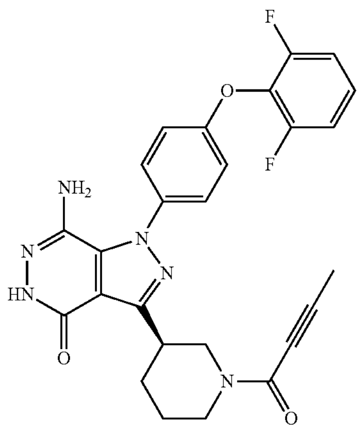 [SMILES: CC#CC(=O)N1CCC[C@@H](c2nn(-c3ccc(Oc4c(F)cccc4F)cc3)c3c(N)n[nH]c(=O)c23)C1] | (R)-7-amino-3-(1-(but-2-ynoyl)piperidin-3-yl)-1-(4-(2,6-difluorophenoxy)phenyl)-1,5-dihydro-4H-pyrazolo[3,4-d]pyridazin-4-one | MS-ESI (m/z): 505 [M + 1]+ |
| 86 | 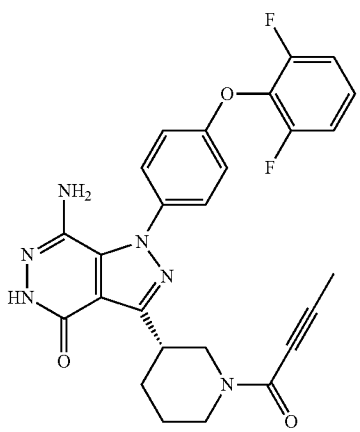 [SMILES: CC#CC(=O)N1CCC[C@H](c2nn(-c3ccc(Oc4c(F)cccc4F)cc3)c3c(N)n[nH]c(=O)c23)C1] | (S)-7-amino-3-(1-(but-2-ynoyl)piperidin-3-yl)-1-(4-(2,6-difluorophenoxy)phenyl)-1,5-dihydro-4H-pyrazolo[3,4-d]pyridazin-4-one | MS-ESI (m/z): 505 [M + 1]+ |
| 87 | 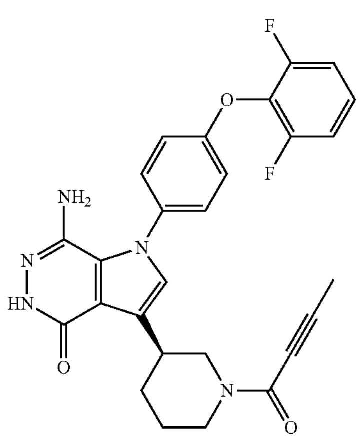 [SMILES: CC#CC(=O)N1CCC[C@@H](c2cn(-c3ccc(Oc4c(F)cccc4F)cc3)c3c(N)n[nH]c(=O)c23)C1] | (S)-7-amino-3-(1-(but-2-ynoyl)piperidin-3-yl)-1-(4-(2,6-difluorophenoxy)phenyl)-1,5-dihydro-4H-pyrrolo[2,3-d]pyridazin-4-one | MS-ESI (m/z): 504 [M + 1]+ |

TABLE 1-continued

| EXAMPLE | NAME | DATA |
|---------|------|------|
| 88 | (R)-7-amino-3-(1-(but-2-ynoyl)piperidin-3-yl)-1-(4-(2,6-difluorophenoxy)phenyl)-1,5-dihydro-4H-pyrrolo[2,3-d]pyridazin-4-one | MS-ESI (m/z): 504 [M + 1]+ |
| 89 | (R)-4-(7-amino-3-(1-(but-2-ynoyl)pyrrolidin-3-yl)-4-oxo-4,5-dihydro-1H-pyrazolo[3,4-d]pyridazin-1-yl)-N-(pyridin-2-yl)benzamide | MS-ESI (m/z): 483 [M + 1]+ |
| 90 | (R)-4-(3-(1-acryloylpyrrolidin-3-yl)-7-amino-4-oxo-4,5-dihydro-1H-pyrazolo[3,4-d]pyridazin-1-yl)-N-(pyridin-2-yl)benzamide | MS-ESI (m/z): 471 [M + 1]+ |

TABLE 1-continued

| EXAMPLE | STRUCTURE | NAME | DATA |
| --- | --- | --- | --- |
| 91 | 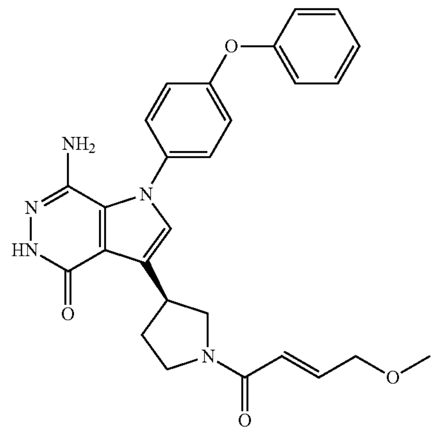 [SMILES: COC/C=C/C(=O)N1CC[C@@H](c2cn(-c3ccc(Oc4ccccc4)cc3)c3c(N)n[nH]c(=O)c23)C1] | (S,E)-7-amino-3-(1-(4-methoxybut-2-enoyl)pyrrolidin-3-yl)-1-(4-phenoxyphenyl)-1,5-dihydro-4H-pyrrolo[2,3-d]pyridazin-4-one | MS-ESI (m/z): 486 [M + 1]+ |
| 92 | 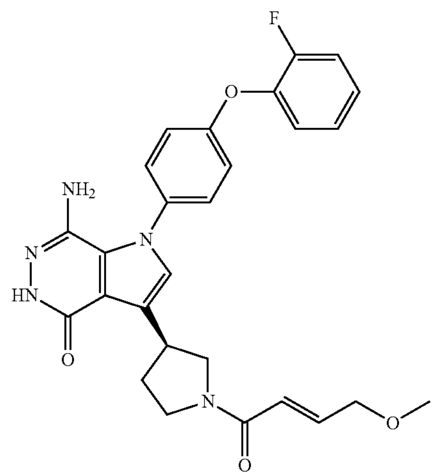 [SMILES: COC/C=C/C(=O)N1CC[C@@H](c2cn(-c3ccc(Oc4ccccc4F)cc3)c3c(N)n[nH]c(=O)c23)C1] | (S,E)-amino-1-(4-(2-fluorophenoxy)phenyl)-3-(1-(4-methoxybut-2-enoyl)pyrrolidin-3-yl)-1,5-dihydro-4H-pyrrolo[2,3-d]pyridazin-4-one | MS-ESI (m/z): 504 [M + 1]+ |
| 93 | 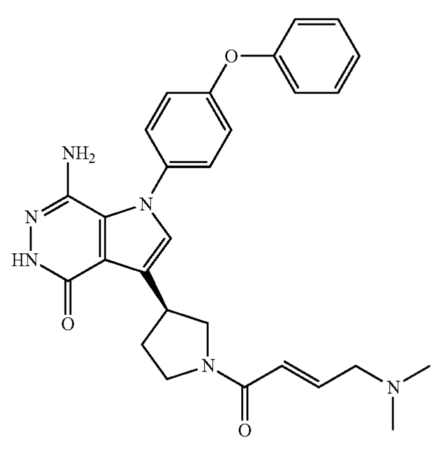 [SMILES: CN(C)C/C=C/C(=O)N1CC[C@@H](c2cn(-c3ccc(Oc4ccccc4)cc3)c3c(N)n[nH]c(=O)c23)C1] | (S,E)-7-amino-3-(1-(4-(dimethylamino)but-2-enoyl)pyrrolidin-3-yl)-1-(4-phenoxyphenyl)-1,5-dihydro-4H-pyrrolo[2,3-d]pyridazin-4-one | MS-ESI (m/z): 499 [M + 1]+ |

TABLE 1-continued

| EXAMPLE | STRUCTURE | NAME | DATA |
|---|---|---|---|
| 94 | 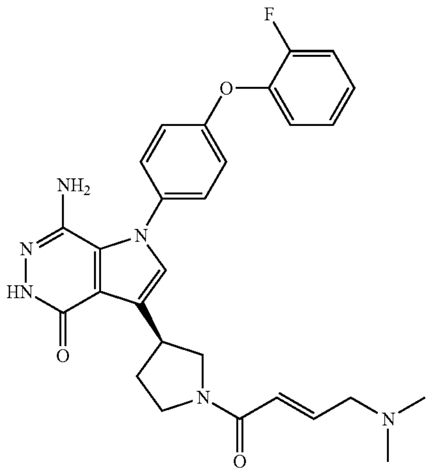 [SMILES: CN(C)C/C=C/C(=O)N1CC[C@@H](c2cn(-c3ccc(Oc4ccccc4F)cc3)c3c(N)n[nH]c(=O)c23)C1] | (S,E)-7-amino-3-(1-(4-(dimethylamino)but-2-enoyl)pyrrolidin-3-yl)-1-(4-(2-fluorophenoxy)phenyl)-1,5-dihydro-4H-pyrrolo[2,3-d]pyridazin-4-one | MS-ESI (m/z): 517 [M + 1]+ |
| 95 | 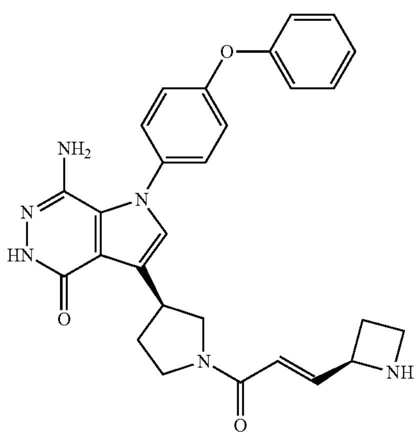 [SMILES: Nc1n[nH]c(=O)c2c([C@@H]3CCN(C(=O)/C=C/[C@H]4CCN4)C3)cn(-c3ccc(Oc4ccccc4)cc3)c12] | 7-amino-3-((S)-1-((E)-3-((R)-azetidin-2-yl)acryloyl)pyrrolidin-3-yl)-1-(4-phenoxyphenyl)-1,5-dihydro-4H-pyrrolo[2,3-d]pyridazin-4-one | MS-ESI (m/z): 497 [M + 1]+ |
| 96 | 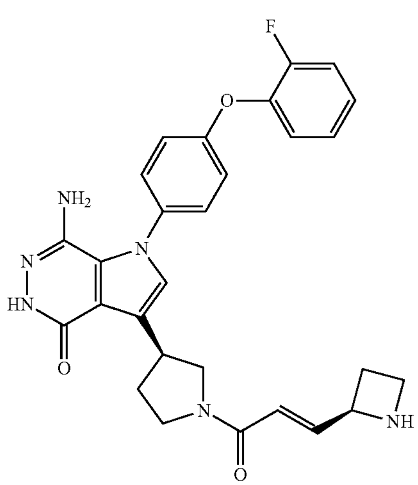 | 7-amino-3-((S)-1-((E)-3-((R)-azetidin-2-yl)acryloyl)pyrrolidin-3-yl)-1-(4-(2-fluorophenoxy)phenyl)-1,5-dihydro-4H-pyrrolo[2,3-d]pyridazin-4-one | MS-ESI (m/z): 515 [M + 1]+ |

TABLE 1-continued

| EXAMPLE | STRUCTURE | NAME | DATA |
|---|---|---|---|
| 97 | 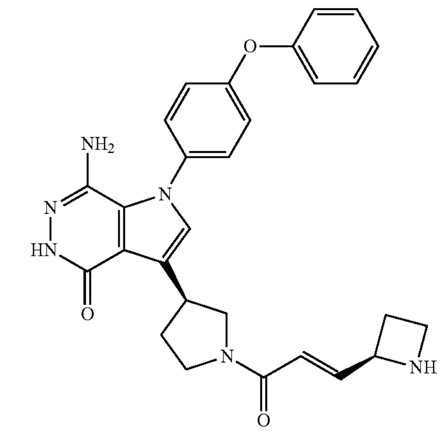 [SMILES: Nc1n[nH]c(=O)c2c([C@@H]3CCN(C(=O)/C=C/[C@H]4CCN4)C3)cn(-c3ccc(Oc4ccccc4)cc3)c12] | 7-amino-3-((S)-1-((E)-3-((R)-azetidin-2-yl)acryloyl)pyrrolidin-3-yl)-1-(4-phenoxyphenyl)-1,5-dihydro-4H-pyrrolo[2,3-d]pyridazin-4-one | MS-ESI (m/z): 497 [M + 1]+ |
| 98 | 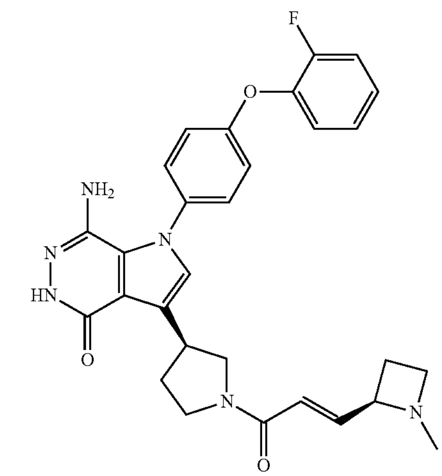 [SMILES: CN1CC[C@@H]1/C=C/C(=O)N1CC[C@@H](c2cn(-c3ccc(Oc4ccccc4F)cc3)c3c(N)n[nH]c(=O)c23)C1] | 7-amino-1-(4-(2-fluorophenoxy)phenyl)-3-((S)-1-((E)-3-((R)-1-methylazetidin-2-yl)acryloyl)pyrrolidin-3-yl)-1,5-dihydro-4H-pyrrolo[2,3-d]pyridazin-4-one | MS-ESI (m/z): 529 [M + 1]+ |
| 99 | 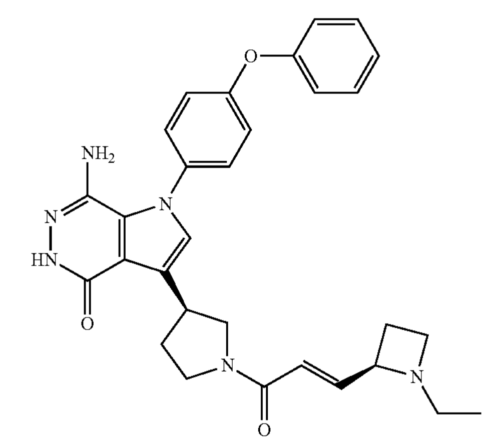 [SMILES: CCN1CC[C@@H]1/C=C/C(=O)N1CC[C@@H](c2cn(-c3ccc(Oc4ccccc4)cc3)c3c(N)n[nH]c(=O)c23)C1] | 7-amino-3-((S)-1-((E)-3-((R)-1-ethylazetidin-2-yl)acryloyl)pyrrolidin-3-yl)-1-(4-phenoxyphenyl)-1,5-dihydro-4H-pyrrolo[2,3-d]pyridazin-4-one | MS-ESI (m/z): 525 [M + 1]+ |

TABLE 1-continued

| EXAMPLE | STRUCTURE | NAME | DATA |
|---|---|---|---|
| 100 | 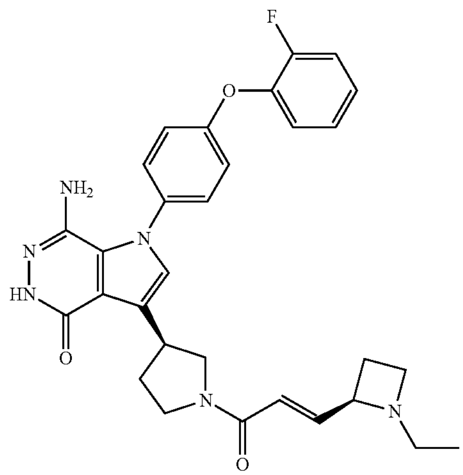 [SMILES: CCN1CC[C@@H]1/C=C/C(=O)N1CC[C@@H](c2cn(-c3ccc(Oc4ccccc4F)cc3)c3c(N)n[nH]c(=O)c23)C1] | 7-amino-3-((S)-1-((E)-3-((R)-1-ethylazetidin-2-yl)acryloyl)pyrrolidin-3-yl)-1-(4-(2-fluorophenoxy)phenyl)-1,5-dihydro-4H-pyrrolo[2,3-d]pyridazin-4-one | MS-ESI (m/z): 543 [M + 1]+ |
| 101 | 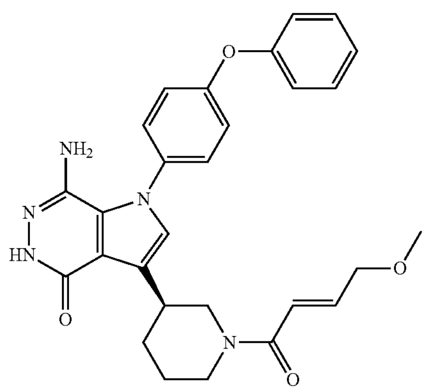 [SMILES: COC/C=C/C(=O)N1CCC[C@@H](c2cn(-c3ccc(Oc4ccccc4)cc3)c3c(N)n[nH]c(=O)c23)C1] | (S,E)-7-amino-3-(1-(4-methoxybut-2-enoyl)piperidin-3-yl)-1-(4-phenoxyphenyl)-1,5-dihydro-4H-pyrrolo[2,3-d]pyridazin-4-one | MS-ESI (m/z): 500 [M + 1]+ |
| 102 | 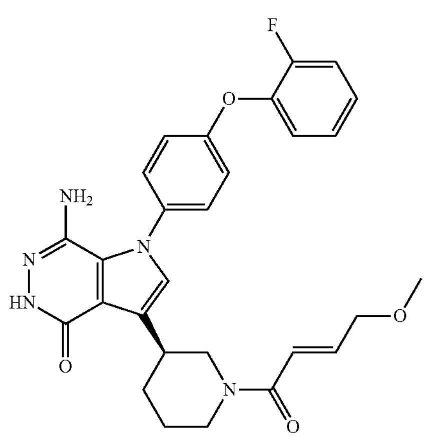 [SMILES: COC/C=C/C(=O)N1CCC[C@@H](c2cn(-c3ccc(Oc4ccccc4F)cc3)c3c(N)n[nH]c(=O)c23)C1] | (S,E)-7-amino-1-(4-(2-fluorophenoxy)phenyl)-3-(1-(4-methoxybut-2-enoyl)piperidin-3-yl)-1,5-dihydro-4H-pyrrolo[2,3-d]pyridazin-4-one | MS-ESI (m/z): 518 [M + 1]+ |

TABLE 1-continued

| EXAMPLE | STRUCTURE | NAME | DATA |
| --- | --- | --- | --- |
| 103 | 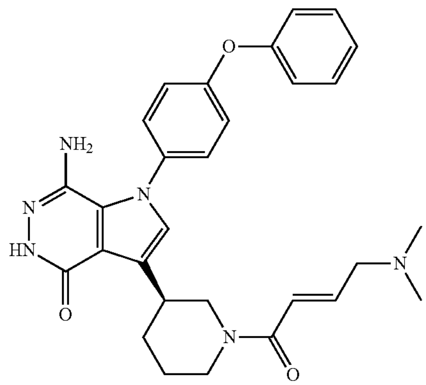 [SMILES: CN(C)C/C=C/C(=O)N1CCC[C@@H](c2cn(-c3ccc(Oc4ccccc4)cc3)c3c(N)n[nH]c(=O)c23)C1] | (S,E)-7-amino-3-(1-(4-(dimethylamino)but-2-enoyl)piperidin-3-yl)-1-(4-phenoxyphenyl)-1,5-dihydro-4H-pyrrolo[2,3-d]pyridazin-4-one | MS-ESI (m/z): 513 [M + 1]+ |
| 104 | 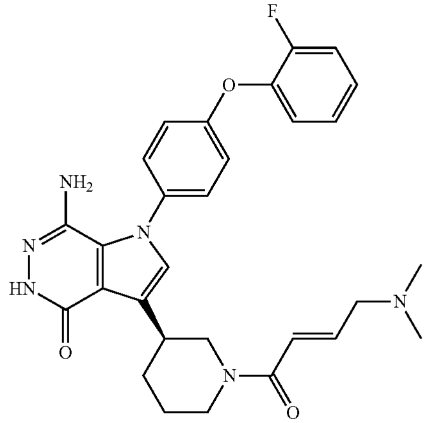 [SMILES: CN(C)C/C=C/C(=O)N1CCC[C@@H](c2cn(-c3ccc(Oc4ccccc4F)cc3)c3c(N)n[nH]c(=O)c23)C1] | (S,E)-7-amino-3-(1-(4-(dimethylamino)but-2-enoyl)piperidin-3-yl)-1-(4-(2-fluorophenoxy)phenyl)-1,5-dihydro-4H-pyrrolo[2,3-d]pyridazin-4-one | MS-ESI (m/z): 531 [M + 1]+ |
| 105 | 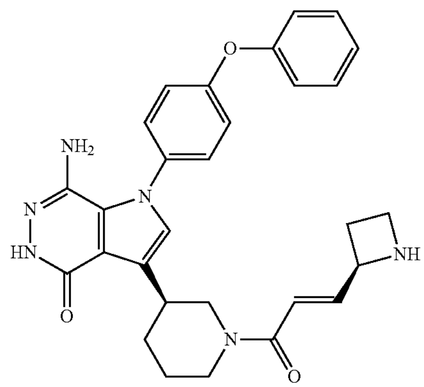 [SMILES: Nc1n[nH]c(=O)c2c([C@@H]3CCCN(C(=O)/C=C/[C@H]4CCN4)C3)cn(-c3ccc(Oc4ccccc4)cc3)c12] | 7-amino-3-((S)-1-((E)-3-((R)-azetidin-2-yl)acryloyl)piperidin-3-yl)-1-(4-phenoxyphenyl)-1,5-dihydro-4H-pyrrolo[2,3-d]pyridazin-4-one | MS-ESI (m/z): 511 [M + 1]+ |
| 106 | 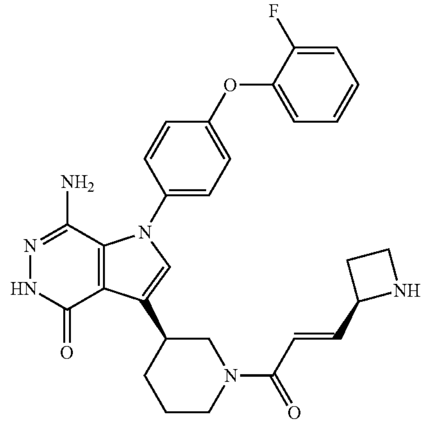 [SMILES: Nc1n[nH]c(=O)c2c([C@@H]3CCCN(C(=O)/C=C/[C@H]4CCN4)C3)cn(-c3ccc(Oc4ccccc4F)cc3)c12] | 7-amino-3-((S)-1-((E)-3-((R)-azetidin-2-yl)acryloyl)piperidin-3-yl)-1-(4-(2-fluorophenoxy)phenyl)-1,5-dihydro-4H-pyrrolo[2,3-d]pyridazin-4-one | MS-ESI (m/z): 529 [M + 1]+ |

TABLE 1-continued

| EXAMPLE | STRUCTURE | NAME | DATA |
|---|---|---|---|
| 107 | 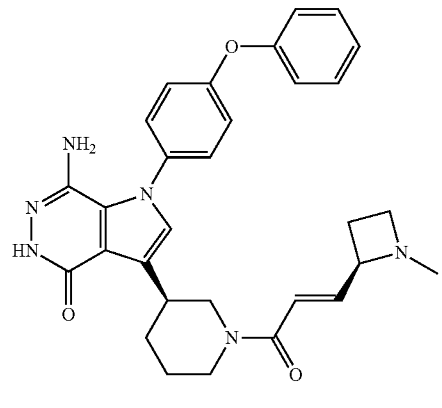 [SMILES: CN1CC[C@@H]1/C=C/C(=O)N1CCC[C@@H](c2cn(-c3ccc(Oc4ccccc4)cc3)c3c(N)n[nH]c(=O)c23)C1] | 7-amino-3-((S)-1-((E)-3-((R)-1-methylazetidin-2-yl)acryloyl)piperidin-3-yl)-1-(4-phenoxyphenyl)-1,5-dihydro-4H-pyrrolo[2,3-d]pyridazin-4-one | MS-ESI (m/z): 525 [M + 1]⁺ |
| 108 | 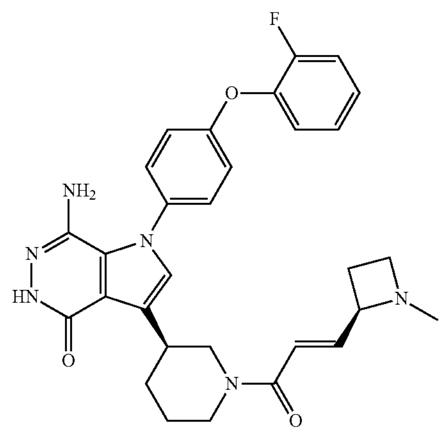 [SMILES: CN1CC[C@@H]1/C=C/C(=O)N1CCC[C@@H](c2cn(-c3ccc(Oc4ccccc4F)cc3)c3c(N)n[nH]c(=O)c23)C1] | 7-amino-1-(4-(2-fluorophenoxy)phenyl)-3-((S)-1-((E)-3-((R)-1-methylazetidin-2-yl)acryloyl) piperidin-3-yl)-1,5-dihydro-4H-pyrrolo[2,3-d] pyridazin-4-one | MS-ESI (m/z): 543 [M + 1]⁺ |
| 109 | 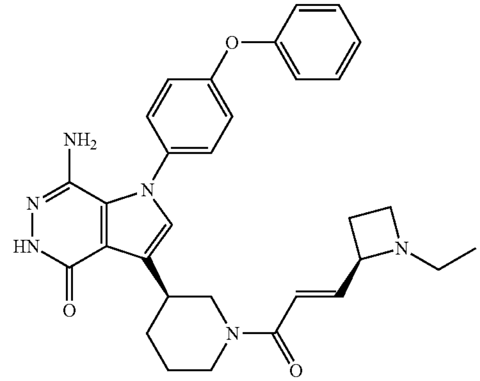 [SMILES: CCN1CC[C@@H]1/C=C/C(=O)N1CCC[C@@H](c2cn(-c3ccc(Oc4ccccc4)cc3)c3c(N)n[nH]c(=O)c23)C1] | 7-amino-3-((S)-1-((E)-3-((R)-1-ethylazetidin-2-yl)acryloyl)piperidin-3-yl)-1-(4-phenoxyphenyl)-1,5-dihydro-4H-pyrrolo[2,3-d]pyridazin-4-one | MS-ESI (m/z): 539 [M + 1]⁺ |

TABLE 1-continued

| EXAMPLE | STRUCTURE | NAME | DATA |
| --- | --- | --- | --- |
| 110 | 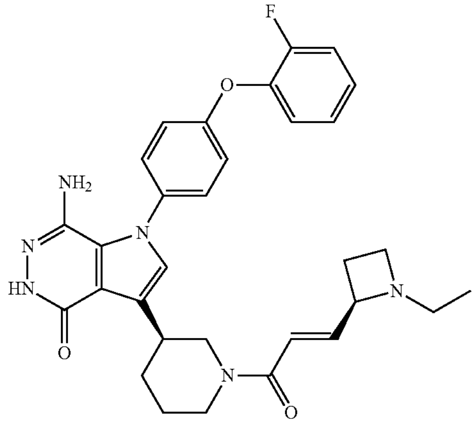 [SMILES: CCN1CC[C@@H]1/C=C/C(=O)N1CCC[C@@H](c2cn(-c3ccc(Oc4ccccc4F)cc3)c3c(N)n[nH]c(=O)c23)C1] | 7-amino-3-((S)-1-((E)-3-((R)-1-ethylazetidin-2-yl)acryloyl)piperidin-3-yl)-1-(4-(2-fluorophenoxy)phenyl)-1,5-dihydro-4H-pyrrolo[2,3-d]pyridazin-4-one | MS-ESI (m/z): 557 [M + 1]+ |
| 111 | 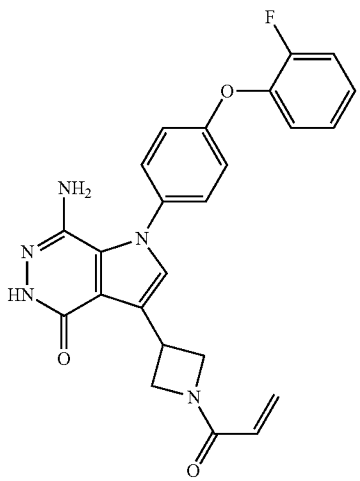 [SMILES: C=CC(=O)N1CC(c2cn(-c3ccc(Oc4ccccc4F)cc3)c3c(N)n[nH]c(=O)c23)C1] | 3-(1-acryloylazetidin-3-yl)-7-amino-1-(4-(2-fluorophenoxy)phenyl)-1,5-dihydro-4H-pyrrolo[2,3-d]pyridazin-4-one | MS-ESI (m/z): 446 [M + 1]+ |
| 112 | 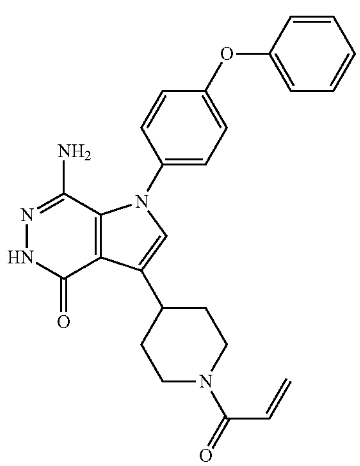 [SMILES: C=CC(=O)N1CCC(c2cn(-c3ccc(Oc4ccccc4)cc3)c3c(N)n[nH]c(=O)c23)CC1] | 3-(1-acryloylpiperidin-4-yl)-7-amino-1-(4-phenoxyphenyl)-1,5-dihydro-4H-pyrrolo[2,3-d]pyridazin-4-one | MS-ESI (m/z): 456 [M + 1]+ |

TABLE 1-continued

| EXAMPLE | STRUCTURE | NAME | DATA |
| --- | --- | --- | --- |
| 113 | 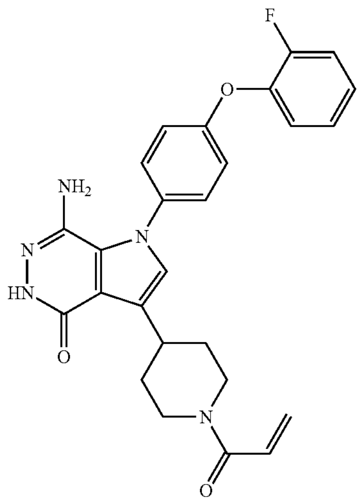 [SMILES: C=CC(=O)N1CCC(c2cn(-c3ccc(Oc4ccccc4F)cc3)c3c(N)n[nH]c(=O)c23)CC1] | 3-(1-acryloylpiperidin-4-yl)-7-amino-1-(4-(2-fluorophenoxy)phenyl)-1,5-dihydro-4H-pyrrolo[2,3-d]pyridazin-4-one | MS-ESI (m/z): 474 [M + 1]+ |
| 114 | 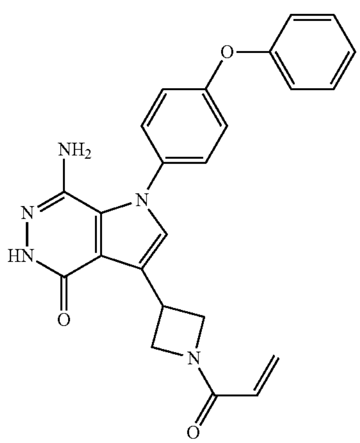 [SMILES: C=CC(=O)N1CC(c2cn(-c3ccc(Oc4ccccc4)cc3)c3c(N)n[nH]c(=O)c23)C1] | 3-(1-acryloylazetidin-3-yl)-7-amino-1-(4-phenoxyphenyl)-1,5-dihydro-4H-pyrrolo[2,3-d]pyridazin-4-one | MS-ESI (m/z): 428 [M + 1]+ |
| 115 | 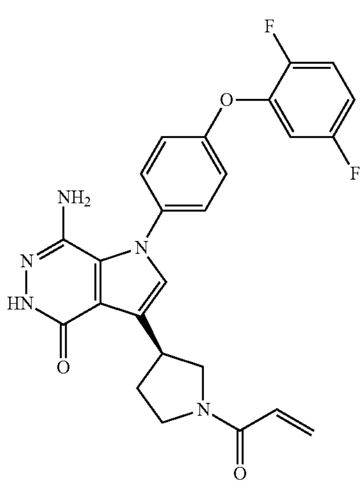 [SMILES: C=CC(=O)N1CC[C@@H](c2cn(-c3ccc(Oc4cc(F)ccc4F)cc3)c3c(N)n[nH]c(=O)c23)C1] | (S)-3-(1-acryloylpyrrolidin-3-yl)-7-amino-1-(4-(2,5-difluorophenoxy)phenyl)-1,5-dihydro-4H-pyrrolo[2,3-d]pyridazin-4-one | MS-ESI (m/z): 478 [M + 1]+ |

TABLE 1-continued

| EXAMPLE | STRUCTURE | NAME | DATA |
|---|---|---|---|
| 116 | 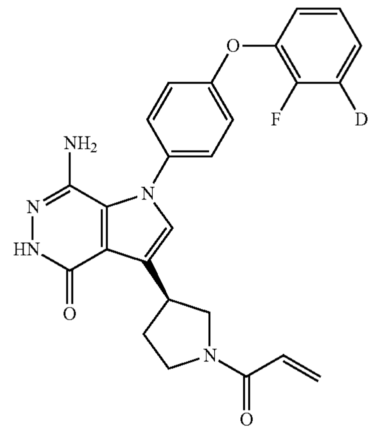 [SMILES: [2H]c1cccc(Oc2ccc(-n3cc([C@@H]4CCN(C(=O)C=C)C4)c4c(=O)[nH]nc(N)c43)cc2)c1F] | (S)-3-(1-acryloylpyrrolidin-3-yl)-7-amino-1-(4-(2-fluorophenoxy-3-d)phenyl)-1,5-dihydro-4H-pyrrolo[2,3-d]pyridazin-4-one | MS-ESI (m/z): 461 [M + 1]+ |
| 117 | 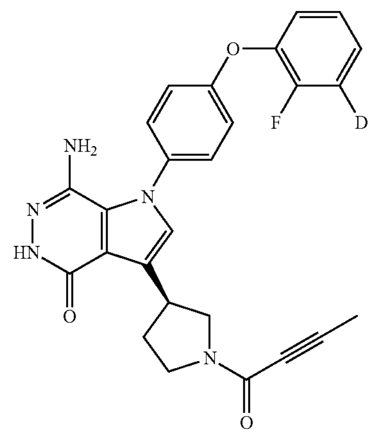 [SMILES: [2H]c1cccc(Oc2ccc(-n3cc([C@@H]4CCN(C(=O)C#CC)C4)c4c(=O)[nH]nc(N)c43)cc2)c1F] | (S)-7-amino-3-(1-(but-2-ynoyl)pyrrolidin-3-yl)-1-(4-(2-fluorophenoxy-3-d)phenyl)-1,5-dihydro-4H-pyrrolo[2,3-d]pyridazin-4-one | MS-ESI (m/z): 473 [M + 1]+ |

Cell Proliferation Assays

MTS testing kit was purchased from Promega. The DMEM, Fetal bovine serum and Penicillin-Streptomycin were purchased from Gibco. Dimethyl sulfoxide (DMSO) was purchased from Sigma.

To investigate whether a compound is able to inhibit the activity of BTK in cells, a mechanism-based assay using DOHH2 (DSMZ catalog#: ACC47) and Mino (ATCC® Number CRL-3000™) cells was developed. In this assay, inhibition of BTK was detected by the inhibition of DOHH2 and Mino cell proliferations. DOHH2 or Mino cells were cultured in culture flasks to 40-80% confluence in RPMI-1640 plus 10% fetal bovine serum. Cells were collected and plated onto 96-well plates at desired cell density (DOHH2: 5000 cells/well; Mino: 10000 cells/well). Plates were incubated overnight at 37° C., with 5% $CO_2$ to adhere. Compounds were added to the plates, and the final compound concentrations were 10000, 3333, 1111, 270, 124, 41, 14, 4.6 and 1.5 nM. Plates were placed at 37° C., with 5% $CO_2$ for 120 h (DOHH2) or 72 h (Mino). 20 μl MTS/100 μl medium mixture solution were added to each well and the plates were incubated for exactly 2 hours. The reaction was stopped by adding 25 μl 10% SDS per well. Absorbance at 490 nm and 650 nm (reference wavelength) were measured and $IC_{50}$ was calculated using GraphPad Prism 5.0.

Select compounds prepared as described above were assayed according to the biological procedures described herein. The results are given in the table 2.

TABLE 2

| Example | DOHH2 $IC_{50}$ (nM) | Example | DOHH2 $IC_{50}$ (nM) | Example | DOHH2 $IC_{50}$ (nM) | Example | DOHH2 $IC_{50}$ (nM) |
|---|---|---|---|---|---|---|---|
| 1 | 36 | 26 | 260 | 57 | 76 | 85 | 435 |
| 2 | 244 | 29 | 46 | 58 | 224 | 87 | 265 |
| 3 | 147 | 30 | 129 | 59 | 248 | 88 | 432 |
| 4 | 250 | 27 | 47 | 62 | 147 | 90 | 580 |
| 5 | 25 | 31 | 167 | 63 | 189 | 91 | 640 |
| 1 | 36 | 26 | 260 | 57 | 76 | 85 | 435 |
| 2 | 244 | 29 | 46 | 58 | 224 | 87 | 265 |
| 3 | 147 | 30 | 129 | 59 | 248 | 88 | 432 |
| 6 | 179 | 32 | 58 | 65 | 505 | 92 | 649 |
| 7 | 182 | 33 | 221 | 66 | 242 | 93 | 239 |
| 8 | 304 | 34 | 42 | 67 | 205 | 94 | 247 |
| 9 | 32 | 35 | 33 | 68 | 146 | 97 | 701 |
| 10 | 20 | 36 | 585 | 69 | 863 | 101 | 208 |
| 11 | 40 | 38 | 175 | 71 | 228 | 102 | 319 |
| 12 | 74 | 39 | 31 | 72 | 260 | 103 | 97 |
| 13 | 107 | 40 | 375 | 73 | 440 | 104 | 151 |
| 14 | 50 | 41 | 146 | 74 | 393 | 107 | 737 |
| 15 | 40 | 44 | 113 | 75 | 383 | 110 | 123 |
| 16 | 37 | 46 | 59 | 76 | 124 | 111 | 261 |
| 17 | 21 | 47 | 60 | 77 | 666 | 112 | 78 |
| 18 | 181 | 50 | 678 | 79 | 164 | 113 | 161 |
| 21 | 100 | 51 | 215 | 80 | 450 | 114 | 473 |
| 22 | 86 | 52 | 321 | 82 | 687 | / | / |
| 23 | 42 | 53 | 196 | 83 | 456 | / | / |
| 24 | 373 | 56 | 42 | 84 | 369 | / | / |

What is claimed is:
1. A compound of formula (II)

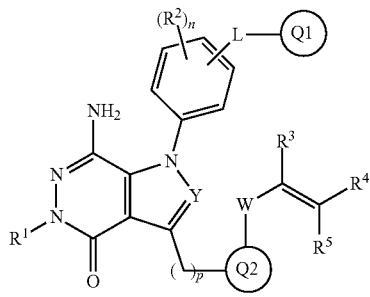

or a pharmaceutically acceptable salt thereof, wherein:

Ring Q1 is selected from aryl and heteroaryl, wherein aryl and heteroaryl are each unsubstituted or substituted with at least one substituent, independently selected from $R^X$;

Ring Q2 is selected from $C_{3-10}$ cycloalkyl, heterocyclyl, aryl and heteroaryl, wherein cycloalkyl, heterocyclyl, aryl and heteroaryl are each unsubstituted or substituted with at least one substituent, independently selected from $R^X$;

L is selected from a bond, —$(CR^{C1}R^{D1})_t$—, —C(O)—, —O—, —$(CR^{C1}R^{D1})_tO$—, —$O(CR^{C1}R^{D1})_t$—, —S—, —S(O)$_r$—, —$(CR^{C1}R^{D1})_tS$—, —$S(CR^{C1}R^{D1})_t$—, —$N(R^{A1})$—, —$N(R^{A1})C(O)$—, —$C(O)N(R^{A1})$—, —$N(R^{A1})C(O)O$—, —$OC(O)N(R^{A1})$—, —$N(R^{A1})C(O)N(R^{B1})$—, —$N(R^{A1})S(O)_2$—, —$S(O)_2N(R^{A1})$— and —$N(R^{A1})S(O)_2N(R^{B1})$—;

W is selected from —C(O)—, —OC(O)—, —$NR^{A1}C(O)$—, —C(=S)—, —S(O)$_r$—, —OS(O)$_r$—, and —$N(R^{A1})S(O)_r$—;

Y is $CR^6$;

$R^1$ is selected from hydrogen, $C_{1-10}$ alkyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, wherein alkyl, cycloalkyl, heterocyclyl, aryl and heteroaryl are each unsubstituted or substituted with at least one substituent, such as one, two, three or four substituents, independently selected from $R^X$;

each $R^2$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, NO$_2$, —$NR^{A2}R^{B2}$, —$OR^{A2}$, —$C(O)R^{A2}$, —$C(=NR^{E2})R$, —$C(=N$—$OR^{B2})R^{A2}$, —$C(O)OR^{A2}$, —$OC(O)R^{A2}$, —$C(O)NR^{A2}R^{B2}$, —$NR^{A2}C(O)R^{B2}$, —$C(=NR^{E2})NR^{A2}R^{B2}$, —$NR^{A2}C(=NR^{E2})R^{B2}$, —$OC(O)NR^{A2}R^{B2}$, —$NR^{A2}C(O)OR^{B2}$, —$NR^{A2}C(O)NR^{A2}R^{B2}$, —$NR^{A2}C(S)NR^{A2}R^{B2}$, —$NR^{A2}C(=NR^{E2})NR^{A2}R^{B2}$, —$S(O)_rR^{A2}$, —$S(O)(=NR^{E2})R^{B2}$, —N=S(O)$R^{A2}R^{B2}$, —$S(O)_2OR^{A2}$, —$OS(O)_2R^{A2}$, —$NR^{A2}S(O)_rR^{B2}$, —$NR^{A2}S(O)(=NR^{E2})R^{B2}$, —$S(O)_rNR^{A2}R^{B2}$, —$S(O)(=NR^{E2})NR^{A2}R^{B2}$, —$NR^{A2}S(O)_2NR^{A2}R^{B2}$, —$NR^{A2}S(O)(=NR^{E2})NR^{A2}R^{B2}$, —$P(O)R^{A2}R^{B2}$ and —$P(O)(OR^{A2})(OR^{B2})$, wherein alkyl, alkenyl, alkynyl, cycloalkyl, heterocyclyl, aryl and heteroaryl are each unsubstituted or substituted with at least one substituent, independently selected from $R^X$;

$R^3$ is selected from hydrogen, halogen, $C_{1-10}$ alkyl, $C_{3-10}$ cycloalkyl, $C_{3-10}$ cycloalkyl-$C_{1-4}$ alkyl, heterocyclyl and heterocyclyl-$C_{1-4}$ alkyl, wherein alkyl, cycloalkyl and heterocyclyl are each unsubstituted or substituted with at least one substituent, independently selected from $R^X$;

$R^4$ is selected from hydrogen, halogen, $C_{1-10}$ alkyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, cycloalkyl, heterocyclyl, aryl and heteroaryl are each unsubstituted or substituted with at least one substituent, independently selected from $R^X$;

$R^4$ is selected from hydrogen, halogen, methoxymethyl, dimethylaminomethyl, $C_{1-10}$ alkyl, $C_{3-10}$ cycloalkyl, $C_{3-10}$ cycloalkyl-$C_{1-4}$ alkyl, heterocyclyl and heterocyclyl-$C_{1-4}$ alkyl, wherein alkyl, cycloalkyl and heterocyclyl, are each unsubstituted or substituted with at least one substituent, independently selected from $R^X$;

or $R^3$ and $R^4$ taken together form a bond;

$R^6$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, NO$_2$, —$NR^{A3}R^{B3}$, —$OR^{A3}$, —$C(O)R^{A3}$, —$C(=NR^{E3})R^{A3}$, —$C(=N$—$OR^{B3})R^{A3}$, —$C(O)OR^{A3}$, —$OC(O)R^{A3}$, —$C(O)NR^{A3}R^{B3}$, —$NR^{A3}C(O)R^{B3}$, —$C(=NR^{E3})NR^{A3}R^{B3}$, —$NR^{A3}C(=NR^{E3})R^{B3}$, —$OC(O)NR^{A3}R^{B3}$, —$NR^{A3}C(O)OR^{B3}$, —$NR^{A3}C(O)NR^{A3}R^{B3}$, —$NR^{A3}C(S)NR^{A3}R^{B3}$, —$NR^{A3}C(=NR^{E3})NR^{A3}R^{B3}$, —$S(O)_rR^{A3}$, —$S(O)(=NR^{E3})R^{B3}$, —N=S(O)$R^{A3}R^{B3}$, —$S(O)_2OR^{A3}$, —$OS(O)_2R^{A3}$, —$NR^{A3}S(O)_rR^{B3}$, —$NR^{A3}S(O)(=NR^{E3})R^{B3}$, —$S(O)_rNR^{A3}R^{B3}$, —$S(O)(=NR^{E3})NR^{A3}R^{B3}$, —$NR^{A3}S(O)_2NR^{A3}R^{B3}$, —$NR^{A3}S(O)(=NR^{E3})NR^{A3}R^{B3}$, —$P(O)R^{A3}R^{B3}$ and —$P(O)(OR^{A3})(OR^{B3})$, wherein alkyl, alkenyl, alkynyl, cycloalkyl, heterocyclyl, aryl and heteroaryl are each unsubstituted or substituted with at least one substituent, independently selected from $R^X$;

each $R^{A1}$, $R^{A2}$, $R^{A3}$, $R^{B1}$, $R^{B2}$ and $R^{B3}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^X$;

or each "$R^{A1}$ and $R^{B1}$", "$R^{A2}$ and $R^{B2}$" or "$R^{A3}$ and $R^{B3}$" together with the atom(s) to which they are attached form a heterocyclic ring of 4 to 12 members containing 0, 1, or 2 additional heteroatoms independently selected from oxygen, sulfur and nitrogen, and optionally substituted with 1 2 or 3 $R^X$ groups;

each $R^{C1}$ and $R^{D1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^X$;

or $R^{C1}$ and $R^{D1}$ together with the carbon atom(s) to which they are attached form a ring of 3 to 12 members containing 0, 1 or 2 heteroatoms independently selected from oxygen, sulfur and nitrogen, and optionally substituted with 1 2 or 3 $R^X$ groups;

each $R^{E2}$ and $R^{E3}$ are independently selected from hydrogen, $C_{1-10}$ alkyl, —CN, —NO$_2$, —OR$^{a1}$, —SR$^{a1}$, —S(O)$_r$R$^{a1}$, —C(O)R$^{a1}$, —C(O)OR$^{a1}$, —C(O)NR$^{a1}$R$^{b1}$ and —S(O)$_r$NR$^{a1}$R$^{b1}$;

each $R^X$ is independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, —CN, —NO$_2$, —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$C(O)R$^{a1}$, —(CR$^{c1}$R$^{d1}$)$_t$C(=NR$^{e1}$)R$^{a1}$, —(CR$^{c1}$R$^{d1}$)$_t$C(=N—OR$^{b1}$)R$^{a1}$, —(CR$^{c1}$R$^{d1}$)$_t$C(O)OR$^{b1}$, —(CR$^{c1}$R$^{d1}$)$_t$OC(O)R$^{b1}$, —(CR$^{c1}$R$^{d1}$)$_t$C(O)NR$^{a1}$R$^{b1}$, —(CR$^{c1}$R$^{d1}$)$_t$NR$^{a1}$C(O)R$^{b1}$, —(CR$^{c1}$R$^{d1}$)$_t$C(=NR$^{e1}$)NR$^{a1}$R$^{b1}$, —(CR$^{c1}$R$^{d1}$)$_t$NR$^{a1}$C(=NR$^{e1}$)R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)OR$^{b1}$, —(CR$^{c1}$R$^{d1}$)$_t$NR$^{a1}$C(O)NR$^{a1}$R$^{b1}$, —(CR$^{c1}$R$^{d1}$)$_t$NR$^{a1}$C(S)NR$^{a1}$R$^{b1}$, —(CR$^{c1}$R$^{d1}$)$_t$NR$^{a1}$C(=NR$^{e1}$)NR$^{a1}$R$^{b1}$, —(CR$^{c1}$R$^{d1}$)$_t$S(O)$_r$R$^{b1}$, —(CR$^{c1}$R$^{d1}$)$_t$S(O)(=NR$^{e1}$)R$^{b1}$, —(CR$^{c1}$R$^{d1}$)$_t$N=S(O)R$^{a1}$R$^{b1}$, —(CR$^{c1}$R$^{d1}$)$_t$S(O)$_2$OR$^{b1}$, —(CR$^{c1}$R$^{d1}$)$_t$OS(O)$_2$R$^{b1}$, —(CR$^{c1}$R$^{d1}$)$_t$NR$^{a1}$S(O)$_r$R$^{b1}$, —(CR$^{c1}$R$^{d1}$)$_t$NR$^{a1}$S(O)(=NR$^{e1}$)R$^{b1}$, —(CR$^{c1}$R$^{d1}$)$_t$S(O)$_r$NR$^{a1}$R$^{b1}$, —(CR$^{c1}$R$^{d1}$)$_t$S(O)(=NR$^{e1}$)NR$^{a1}$R$^{b1}$, —(CR$^{c1}$R$^{d1}$)$_t$NR$^{a1}$S(O)$_2$NR$^{a1}$R$^{b1}$, —(CR$^{c1}$R$^{d1}$)$_t$NR$^{a1}$S(O)(=NR$^{e1}$)NR$^{a1}$R$^{b1}$, —(CR$^{c1}$R$^{d1}$)$_t$P(O)R$^{a1}$R$^{b1}$ and —(CR$^{c1}$R$^{d1}$)$_t$P(O)(OR$^{a1}$)(OR$^{b1}$), wherein alkyl, alkenyl, alkynyl, cycloalkyl, heterocyclyl, aryl and heteroaryl are each unsubstituted or substituted with at least one substituent, independently selected from R$^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from R$^Y$;

or $R^{a1}$ and $R^{b1}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1, 2 or 3 R$^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from R$^Y$;

or $R^{c1}$ and $R^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 R$^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, CN, NO$_2$, —OR$^{a2}$, —SR$^{a2}$, —S(O)$_r$R$^{a2}$, —C(O)R$^{a2}$, —C(O)OR$^{a2}$, —S(O)$_r$NR$^{a2}$R$^{b2}$ and —C(O)NR$^{a2}$R$^{b2}$;

each $R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, NO$_2$, —(CR$^{c2}$R$^{d2}$)$_t$NR$^{a2}$R$^{b2}$, —(CR$^{c2}$R$^{d2}$)$_t$OR$^{b2}$, —(CR$^{c2}$R$^{d2}$)$_t$C(O)R$^{a2}$, —(CR$^{c2}$R$^{d2}$)$_t$C(=NR$^{e2}$)R$^{a2}$, —(CR$^{c2}$R$^{d2}$)$_t$C(=N—OR$^{b2}$)R$^{a2}$, —(CR$^{c2}$R$^{d2}$)$_t$C(O)OR$^{b2}$, —(CR$^{c2}$R$^{d2}$)$_t$OC(O)R$^{b2}$, —(CR$^{c2}$R$^{d2}$)$_t$C(O)NR$^{a2}$R$^{b2}$, —(CR$^{c2}$R$^{d2}$)$_t$NR$^{a2}$C(O)R$^{b2}$, —(CR$^{c2}$R$^{d2}$)$_t$C(=NR$^{e2}$)NR$^{a2}$R$^{b2}$, —(CR$^{c2}$R$^{d2}$)$_t$NR$^{a2}$C(=NR$^{e2}$)R$^{b2}$, —(CR$^{c2}$R$^{d2}$)$_t$OC(O)NR$^{a2}$R$^{b2}$, —(CR$^{c2}$R$^{d2}$)$_t$NR$^{a2}$C(O)OR$^{b2}$, —(CR$^{c2}$R$^{d2}$)$_t$NR$^{a2}$C(O)NR$^{a2}$R$^{b2}$, —(CR$^{c2}$R$^{d2}$)$_t$NR$^{a2}$C(S)NR$^{a2}$R$^{b2}$, —(CR$^{c2}$R$^{d2}$)$_t$NR$^{a2}$C(=NR$^{e2}$)NR$^{a2}$R$^{b2}$, —(CR$^{c2}$R$^{d2}$)$_t$S(O)$_r$R$^{b2}$, —(CR$^{c2}$R$^{d2}$)$_t$S(O)(=NR$^{e2}$)R$^{b2}$, —(CR$^{c2}$R$^{d2}$)$_t$N=S(O)R$^{a2}$R$^{b2}$, —(CR$^{c2}$R$^{d2}$)$_t$S(O)$_2$OR$^{b2}$, —(CR$^{c2}$R$^{d2}$)$_t$OS(O)$_2$R$^{b2}$, —(CR$^{c2}$R$^{d2}$)$_t$NR$^{a2}$S(O)$_r$R$^{b2}$, —(CR$^{c2}$R$^{d2}$)$_t$NR$^{a2}$S(O)(=NR$^{e2}$)R$^{b2}$, —(CR$^{c2}$R$^{d2}$)$_t$S(O)$_r$NR$^{a2}$R$^{b2}$, —(CR$^{c2}$R$^{d2}$)$_t$S(O)(=NR$^{e2}$)NR$^{a2}$R$^{b2}$, —(CR$^{c2}$R$^{d2}$)$_t$NR$^{a2}$S(O)$_2$NR$^{a2}$R$^{b2}$, —(CR$^{c2}$R$^{d2}$)$_t$NR$^{a2}$S(O)(=NR$^{e2}$)NR$^{a2}$R$^{b2}$, —(CR$^{c2}$R$^{d2}$)$_t$P(O)R$^{a2}$R$^{b2}$ and —(CR$^{c2}$R$^{d2}$)$_t$P(O)(OR$^{a2}$)(OR$^{b2}$), wherein alkyl, alkenyl, alkynyl, cycloalkyl, heterocyclyl, aryl and heteroaryl are each unsubstituted or substituted with at least one substituent, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, independently selected from halogen, —CN, $C_{1-10}$ alkyl, $C_{2-10}$ alkenyl, $C_{2-10}$ alkynyl, $C_{3-10}$ cycloalkyl, —OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1 or 2 substituents, independently selected from halogen, —CN, $C_{1-10}$ alkyl, $C_{2-10}$ alkenyl, $C_{2-10}$ alkynyl, $C_{3-10}$ cycloalkyl, —OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, independently selected from halogen, —CN, $C_{1-10}$ alkyl, $C_{2-10}$ alkenyl, $C_{2-10}$ alkynyl, $C_{3-10}$ cycloalkyl, —OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1 or 2 heteroatoms independently selected from oxygen, sulfur and nitrogen, and optionally substituted with 1 or 2 substituents, independently selected from halogen, —CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)O$C_{1-4}$ alkyl, —C(O)O$C_{3-10}$ cycloalkyl, —C(O)N($C_{1-4}$ alkyl)$_2$, —C(O)N($C_{3-10}$ cycloalkyl)$_2$, —S(O)$_2C_{1-4}$ alkyl, —S(O)$_2C_{3-10}$ cycloalkyl, —S(O)$_2$N($C_{1-4}$ alkyl)$_2$ and —S(O)$_2$N($C_{3-10}$ cycloalkyl)$_2$;

n is selected from 0, 1, 2, 3 and 4;
p is selected from 0, 1 and 2;
each r is independently selected from 1 and 2; and
each t is independently selected from 1, 2, 3 and 4.

2. A compound of claim 1 or a pharmaceutically acceptable salt thereof, wherein Y is CH.

3. A compound of claim 1 or a pharmaceutically acceptable salt thereof, wherein L is selected from —O— and —C(O)NH—.

4. A compound of claim 1 or a pharmaceutically acceptable salt thereof, wherein Ring Q1 is selected from phenyl and pyridinyl, wherein phenyl and pyridinyl are independently unsubstituted or substituted with at least one substituent independently selected from $R^X$.

5. A compound of claim 1 or a pharmaceutically acceptable salt thereof, wherein the substructure

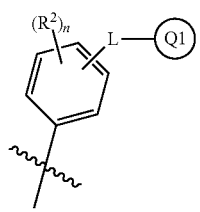

in Formula (II) is

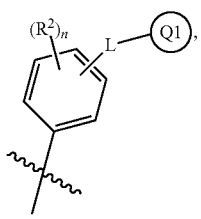

wherein the ⁓ symbol indicates the point of attachment to the rest of the molecule.

6. A compound of claim 1 or a pharmaceutically acceptable salt thereof, wherein $R^1$ is hydrogen.

7. A compound of claim 1 or a pharmaceutically acceptable salt thereof, wherein $R^2$ is hydrogen.

8. A compound of claim 1 or a pharmaceutically acceptable salt thereof, wherein p is 0.

9. A compound of claim 1 or a pharmaceutically acceptable salt thereof, wherein Ring Q2 is selected from azetidinyl, pyrrolidinyl and piperidinyl, wherein azetidinyl, pyrrolidinyl and piperidinyl are each independently unsubstituted or substituted with at least one substituent independently selected from $R^X$.

10. A compound of claim 9 or a pharmaceutically acceptable salt thereof, wherein W is —C(O)— and the attachment of W to Q2 is through N.

11. A compound of claim 1 or a pharmaceutically acceptable salt thereof, wherein $R^3$ and $R^5$ are hydrogen.

12. A compound of claim 1 or a pharmaceutically acceptable salt thereof, wherein $R^4$ is selected from hydrogen, methoxymethyl, dimethylaminomethyl and azetidinyl, wherein azetidinyl is unsubstituted or substituted with at least one substituent independently selected from $R^X$.

13. A compound of claim 12 or a pharmaceutically acceptable salt thereof, wherein $R^X$ is selected from methyl and ethyl.

14. A compound of claim 1 or a pharmaceutically acceptable salt thereof, wherein $R^3$ and $R^4$ taken together form a bond, and $R^5$ is $C_{1-10}$ alkyl.

15. A compound of claim 14 or a pharmaceutically acceptable salt thereof, wherein $R^5$ is methyl.

16. A compound selected from
3-(1-acryloylpyrrolidin-3-yl)-7-amino-1-(4-phenoxyphenyl)-1,5-dihydro-4H-pyrrolo[2,3-d]pyridazin-4-one,
7-amino-3-(1-(but-2-ynoyl)pyrrolidin-3-yl)-1-(4-phenoxyphenyl)-1,5-dihydro-4H-pyrrolo[2,3-d]pyridazin-4-one,
3-(1-acryloylpyrrolidin-3-yl)-7-amino-1-(4-(2,6-difluorophenoxy)phenyl)-1,5-dihydro-4H-pyrrolo[2,3-d]pyridazin-4-one,
7-amino-3-(1-(but-2-ynoyl)pyrrolidin-3-yl)-1-(4-(2,6-difluorophenoxy)phenyl)-1,5-dihydro-4H-pyrrolo[2,3-d]pyridazin-4-one,
(S)-3-(1-acryloylpyrrolidin-3-yl)-7-amino-1-(4-phenoxyphenyl)-1,5-dihydro-4H-pyrazolo[2,3-d]pyridazin-4-one,
(R)-3-(1-acryloylpyrrolidin-3-yl)-7-amino-1-(4-phenoxyphenyl)-1,5-dihydro-4H-pyrazolo[2,3-d]pyridazin-4-one,
(S)-3-(1-acryloylpyrrolidin-3-yl)-7-amino-1-(4-phenoxyphenyl)-1,5-dihydro-4H-pyrazolo[2,3-d]pyridazin-4-one,
(R)-3-(1-acryloylpyrrolidin-3-yl)-7-amino-1-(4-phenoxyphenyl)-1,5-dihydro-4H-pyrazolo[2,3-d]pyridazin-4-one,
(S)-3-(1-acryloylpyrrolidin-3-yl)-7-amino-1-(4-(2-fluorophenoxy)phenyl)-1,5-dihydro-4H-pyrrolo[2,3-d]pyridazin-4-one,
(S)-3-(1-acryloylpyrrolidin-3-yl)-7-amino-1-(4(3-fluorophenoxy)phenyl)-1,5-dihydro-4H-pyrrolo[2,3-d]pyridazin-4-one,
(S)-3-(1-acryloylpyrrolidin-3-yl)-7-amino-1-(4(4-fluorophenoxy)phenyl)-1,5-dihydro-4H-pyrrolo[2,3-d]pyridazin-4-one,
(S)-3-(1-acryloylpyrroldin-3-yl)-7-amino-1-(4-(4(2,3-difluorophenoxy)phenyl)-1,5-dihydro-4H-pyrrolo[2,3-d]pyridazin-4-one,
(S)-3-(1-acryloylpyrrolidin-3-yl)-7-amino-1-(4-(2,6-difluorophenoxy)phenyl)-1,5-dihydro-4H-pyrazolo[2,3-d]pyridazin-4-one, (S)-3-(1-acryloylpyrrolidin-3-yl)-7-amino-1-(4-(3,5-difluorophenoxy)phenyl)-1,5-dihydro-4H-pyrazolo[2,3-d]pyridazin-4-one,
(R)-3-(1-acryloylpyrrolidin-3-yl)-7-amino-1-(4-(2-fluorophenoxy)phenyl)-1,5-dihydro-4H-pyrazolo[3,4-d]pyridazin-4-one,
(R)-3-(1-acryloylpyrrolidin-3-yl)-7-amino-1-(4-(3-fluorophenoxy)phenyl)-1,5-dihydro-4H-pyrazolo[3,4-d]pyridazin-4-one,
(R)-3-(1-acryloylpyrrolidin-3-yl)-7-amino-1-(4-(4-fluorophenoxy)phenyl)-1,5-dihydro-4H-pyrrolo[2,3-d]pyridazin-4-one,
(R)-3-(1-acryloylpyrrolidin-3-yl)-7-amino-1-(4-(2,3-difluorophenoxy)phenyl)-1,5-dihydro-4H-pyrrolo[2,3-d]pyridazin-4-one,
(R)-3-(1-acryloylpyrrolidin-3-yl)-7-amino-1-(4-(2,6-difluorophenoxy)phenyl)-1,5-dihydro-4H-pyrrolo[2,3-d]pyridazin-4-one,
(R)-3-(1-acryloylpyrrolidin-3-yl)-7-amino-1-(4-(3,5-difluorophenoxy)phenyl)-1,5-dihydro-4H-pyrrolo[2,3-d]pyridazin-4-one,
(S)-3-(1-acryloylpyrrolidin-3-yl)-7-amino-1-(4-(2-fluorophenoxy)phenyl)-1,5-dihydro-4H-pyrrolo[2,3-d]pyridazin-4-one,
(S)-3-(1-acryloylpyrrolidin-3-yl)-7-amino-1-(4-(3-fluorophenoxy)phenyl)-1,5-dihydro-4H-pyrrolo[2,3-d]pyridazin-4-one,
(S)-3-(1-acryloylpyrrolidin-3-yl)-7-amino-1-(4-(4-fluorophenoxy)phenyl)-1,5-dihydro-4H-pyrrolo[2,3-d]pyridazin-4-one,
(S)-3-(1-acryloylpyrrolidin-3-yl)-7-amino-1-(4-(2,3-difluorophenoxy)phenyl)-1,5-dihydro-4H-pyrrolo[2,3-d]pyridazin-4-one,
(S)-3-(1-acryloylpyrrolidin-3-yl)-7-amino-1-(4-(2,6-difluorophenoxy)phenyl)-1,5-dihydro-4H-pyrrolo[2,3-d]pyridazin-4-one,
(S)-3-(1-acryloylpyrrolidin-3-yl)-7-amino-1-(4-(3,5-difluorophenoxy)phenyl)-1,5-dihydro-4H-pyrrolo[2,3-d]pyridazin-4-one,
(R)-3-(1-acryloylpyrrolidin-3-yl)-7-amino-1-(4-(2-fluorophenoxy)phenyl)-1,5-dihydro-4H-pyrrolo[2,3-d]pyridazin-4-one,
(R)-3-(1-acryloylpyrrolidin-3-yl)-7-amino-1-(4-(3-fluorophenoxy)phenyl)-1,5-dihydro-4H-pyrrolo[2,3-d]pyridazin-4-one,
(R)-3-(1-acryloylpiperidin-3-yl)-7-amino-1-(4-(4-fluorophenoxy)phenyl)-1,5-dihydro-4H-pyrrolo[2,3-d]pyridazin-4-one,
(R)-3-(1-acryloylpiperidin-3-yl)-7-amino-1-(4-(2,3-difluorophenoxy)phenyl)-1,5-dihydro-4H-pyrrolo[2,3-d]pyridazin-4-one,
(R)-3-(1-acryloylpiperidin-3-yl)-7-amino-1-(4-(2,6-difluorophenoxy)phenyl)-1,5-dihydro-4H-pyrrolo[2,3-d]pyridazin-4-one,
(R)-3-(1-acryloylpiperidin-3-yl)-7-amino-1-(4-(3,5-difluorophenoxy)phenyl)-1,5-dihydro-4H-pyrrolo[2,3-d]pyridazin-4-one,
(S)-7-amino-3-(1-(but-2-ynoyl)pyrrolidin-3-yl)-1-(4-phenoxyphenyl)-1,5-dihydro-4H-pyrrolo[2,3-d]pyridazin-4-one,
(R)-7-amino-3-(1-(but-2-ynoyl)pyrrolidin-3-yl)-1-(4-phenoxyphenyl)-1,5-dihydro-4H-pyrrolo[2,3-d]pyridazin-4-one,
(S)-7-amino-3-(1-(but-2-ynoyl)pyrrolidin-3-yl)-1-(4-phenoxyphenyl)-1,5-dihydro-4H-pyrrolo[2,3-d]pyridazin-4-one,
(R)-7-amino-3-(1-(but-2-ynoyl)pyrrolidin-3-yl)-1-(4-phenoxyphenyl)-1,5-dihydro-4H-pyrrolo[2,3-d]pyridazin-4-one,
(S)-7-amino-3-(1-(but-2-ynoyl)pyrrolidin-3-yl)-1-(4-fluorophenoxy)phenyl)-1,5-dihydro-4H-pyrrolo[2,3-d]pyridazin-4-one,
(R)-7-amino-3-(1-(but-2-ynoyl)pyrrolidin-3-yl)-1-(4-(2-fluorophenoxy)phenyl)-1,5-dihydro-4H-pyrrolo[2,3-d]pyridazin-4-one,
(S)-7-amino-3-(1-(but-2-ynoyl)piperidin-3-yl)-1-(4-(2-fluorophenoxy)phenyl)-1,5-dihydro-4H-pyrrolo[2,3-d]pyridazin-4-one,
(R)-7-amino-3-(1-(but-2-ynoyl)piperidin-3-yl)-1-(4-(2-fluorophenoxy)phenyl)-1,5-dihydro-4H-pyrrolo[2,3-d]pyridazin-4-one,
(S)-7-amino-3-(1-(but-2-ynoyl)piperidin-3-yl)-1-(4-(2,6-difluorophenoxy)phenyl)-1,5-dihydro-4H-pyrazolo[3,4-d]pyridazin-4-one,
(R)-7-amino-3-(1-(but-2-ynoyl)piperidin-3-yl)-1-(4-(2,6-difluorophenoxy)phenyl)-1,5-dihydro-4H-pyrazolo[3,4-d]pyridazin-4-one,
(S))-7-amino-3-(1-(but-2-ynoyl)piperidin-3-yl)-1-(4-(2,6-difluorophenoxy)phenyl)-1,5-dihydro-4H-pyrazolo[3,4-d]pyridazin-4-one,
(R)-7-amino-3-(1-(but-2-ynoyl)piperidin-3-yl)-1-(4-(2,6-difluorophenoxy)phenyl)-1,5-dihydro-4H-pyrazolo[3,4-d]pyridazin-4-one,
(R)-7-amino-3-(1-(but-2-ynoyl)piperidin-3-yl)-1-(4-(2,6-difluorophenoxy)phenyl)-1,5-dihydro-4H-pyrazolo[3,4-d]pyridazin-4-one,
(R)-7-amino-3-(1-(but-2-ynoyl)piperidin-3-yl)-1-(4-(3,5-difluorophenoxy)phenyl)-1,5-dihydro-4 H-pyrazolo[3,4-d]pyridazin-4-one,
(S,E)-7-amino-3-(1-(4-methoxybut-2-enoyl)pyrrolidin-3-yl)-1-(4-phenoxyphenyl)-1,5-dihydro-4H-pyrazolo[3,4-d]pyridazin-4-one,
(S,E)7-amino-1-(4-(3-fluorophenoxy)phenyl)-3-(1(4-methoxybut-2enoyl)pyrrolidin-3-yl)-1,5dihydro-4H-pyrazolo[2,3-d]pyridazin-4-one,
(S,E)-7-amino-3-(1-(4-(dimethylamino)but-2-enoyl)pyrrolidin-3-yl)-1-(4-phenenoxyphenyl)-1,5dihydro-4H-pyrazolo[2,3-d]pyridazin-4-one,
(S,E)-7-amino-3-(1-(4-(dimethylamino)but-2-enoyl)pyrrolidin-3-yl)-1-(4-(2-fluorophenoxy)phenyl)-1,5-dihydro-4H-pyrazolo[2,3-d]pyridazin-4-one,
7-amino-3-((S)-1-((E)-3-((R)-azetidin-2-yl)acryloyl)pyrrolidin-3-yl)-1-(4-phenoxyphenyl)-1,5-dihydro-4H-pyrazolo[2,3-d]pyridazin-4-one,
7-amino-3-((S)-1-((E)-3-((R)-azetidin-2-yl)acryloyl)pyrrolidin-3-yl)-1-(4(2-fluorophenoxy)phenyl)-1,5-dihydro-4H-pyrazolo[2,3-d]pyridazin-4-one,
7-amino-3-((S)-1-((E)-3-((R)-azetidin-2-yl)acryloyl)pyrrolidin-3-yl)-1-(4-phenoxyphenyl)-1,5-dihydro-4H-pyrazolo[2,3-d]pyridazin-4-one,
7-amino-1-(4-(2-fluorophenoxy)phenyl)-3-((S)-1-((E)-3-((R)-1-methylazetidin-2-yl)acryloyl)pyrrolidin-3-yl)-1,5-dihydro-4H-pyrrolo[2,3-d]pyridazin-4-one,
7-amino-3-((S)-1-((E)-3-((R)-1-ethylazetidin-2-yl)acryloyl)pyrrolidin-3-yl)-1-(4-phenoxyphenyl)-1,5-dihydro-4H-pyrrolo[2,3-d]pyridazin-4-one,
7-amino-3-((S)-1-((E)-3-((R)-1-ethyl azetidin-2-yl)acryloyl)pyrrolidin-3-yl)-1-(4-(2-fluorophenoxy)phenyl)-1,5-dihydro-4H-pyrrolo[2,3-d]pyridazin-4-one,
(S,E)-7-amino-3-(1-(4-methoxybut-2-enoyl)piperidin-3-yl)-1-(4-phenoxyphenyl)-1,5-dihydro-4H-pyrrolo[2,3-d]pyridazin-4-one, (S,E)-7-amino-1-(4-(2-fluorophenoxy)phenyl)-3-(1-(4-methoxybut-2-enoyl)piperidin-3-yl)-1,5-dihydro-4H-pyrrolo[2,3-d]pyridazin-4-one, (S,E)-7-amino-3-(1-(4-(dimethylamino)but-2-enoyl)piperidin-3-yl)-1-(4-phenoxyphenyl)-1,5-dihydro-4H-pyrrolo[2,3-d]pyridazin-4-one, (S,E)-7-amino-3-(1-(4-(dimethylamino)but-2-enoyl)piperidin-3-yl)-1-(4-(2-fluorophenoxy)phenyl)-1,5-dihydro-4H-pyrrolo[2,3-d]pyridazin-4-one, 7-amino-3-((S)-1-((E)-3-((R)-azetidin-2-yl)acryloyl)piperidin-3-yl)-1-(4-phenoxyphenyl)-1,5-dihydro-4H-pyrrolo[2,3-d]pyridazin-4-one, 7-amino-3-((S)-1-((E)-3-((R)-azetidin-2-yl)acryloyl)piperidin-3-yl)-1-(4-(2-fluorophenoxy)phenyl)-1,5-dihydro-4H-pyrrolo[2,3-d]pyridazin-4-one, 7-amino-3-((S)-1-((E)-3-((R)-1-methylazetidin-2-yl)acryloyl)piperidin-3-yl)-1-(4-phenoxyphenyl)-1,5-dihydro-4H-pyrrolo[2,3-d]pyridazin-4-one, 7-amino-1-(4-(2-fluorophenoxy)phenyl)-3-((S)-1-((E)-3-((R)-1-methylazetidin-2-yl)acryloyl)piperidin-3-yl)-1,5-dihydro-4H-pyrrolo[2,3-d]pyridazin-4-one, 7-amino-3-((S)-1-((E)-3-((R)-1-ethylazetidin-2-yl)acryloyl)piperidin-3-yl)-1-(4-phenoxyphenyl)-1,5-dihydro-4H-pyrrolo[2,3-d]pyridazin-4-one, 7-amino-3-((S)-1-((E)-3-((R)-1-ethyl azetidin-2-yl)acryloyl)piperidin-3-yl)-1-(4-(2-fluorophenoxy)phenyl)-1,5-dihydro-4H-pyrrolo[2,3-d]pyridazin-4-one, 3-(1-acryloylazetidin-3-yl)-7-amino-1-(4-(2-fluorophenoxy)phenyl)-1,5-dihydro-4H-pyrrolo[2,3-d]pyridazin-4-one, 3-(1-acryloylpiperidin-4-yl)-7-amino-1-(4-phenoxyphenyl)-1,5-dihydro-4H-pyrrolo[2,3-d]pyridazin-4-one, 3-(1-acryloylpiperidin-4-yl)-7-amino-1-(4-(2-fluorophenoxy)phenyl)-1,5-dihydro-4H-pyrrolo[2,3-d]pyridazin-4-one, 3-(1-acryloylazetidin-3-yl)-7-amino-1-(4-phenoxyphenyl)-1,5-dihydro-4H-pyrrolo[2,3-d]pyridazin-4-one, (S)-3-(1-acryloylpyrrolidin-3-yl)-7-amino-1-(4-(2,5-difluorophenoxy)phenyl)-1,5-dihydro-4H-pyrrolo[2,3-d]pyridazin-4-one, (S)-3-(1-acryloylpyrrolidin-3-yl)-7-amino-1-(4-(2-fluorophenoxy-3-d)phenyl)-1,5-dihydro-4H-pyrrolo[2,3-d]pyridazin-4-one, (S)-7-amino-3-(1-(but-2-ynoyl)pyrrolidin-3-yl)-1-(4-(2-fluorophenoxy-3-d)phenyl)-1,5-dihydro-4H-pyrrolo[2,3-d]pyridazin-4-one, and pharmaceutically acceptable salts thereof.

17. A pharmaceutical composition, comprising a compound of claim 1, or a pharmaceutically acceptable salt thereof, and at least one pharmaceutically acceptable carrier.

18. A pharmaceutical composition, comprising a compound of claim 16, or a pharmaceutically acceptable salt thereof, and at least one pharmaceutically acceptable carrier.

\* \* \* \* \*